US010434164B2

(12) United States Patent
Gale, Jr. et al.

(10) Patent No.: US 10,434,164 B2
(45) Date of Patent: Oct. 8, 2019

(54) METHODS AND COMPOSITIONS FOR ACTIVATION OF INNATE IMMUNE RESPONSES THROUGH RIG-I LIKE RECEPTOR SIGNALING

(71) Applicant: University of Washington through its Center for Commercialization, Seattle, WA (US)

(72) Inventors: Michael J. Gale, Jr., Seattle, WA (US); Gretja Schnell, Seattle, WA (US); Yueh-Ming Loo, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 15/711,934

(22) Filed: Sep. 21, 2017

(65) Prior Publication Data

US 2018/0104325 A1    Apr. 19, 2018

Related U.S. Application Data

(62) Division of application No. 14/327,439, filed on Jul. 9, 2014, now Pat. No. 9,775,894.

(60) Provisional application No. 61/844,022, filed on Jul. 9, 2013.

(51) Int. Cl.
| | | |
|---|---|---|
| *A61K 39/39* | (2006.01) | |
| *A61K 39/12* | (2006.01) | |
| *C12N 15/117* | (2010.01) | |
| *C07H 21/04* | (2006.01) | |
| *A61K 31/00* | (2006.01) | |
| *A61K 45/06* | (2006.01) | |
| *A61K 39/00* | (2006.01) | |

(52) U.S. Cl.
CPC .............. *A61K 39/12* (2013.01); *A61K 31/00* (2013.01); *A61K 39/39* (2013.01); *A61K 45/06* (2013.01); *C07H 21/04* (2013.01); *C12N 15/117* (2013.01); *A61K 2039/555* (2013.01); *A61K 2039/55561* (2013.01); *A61K 2039/57* (2013.01); *C12N 2310/17* (2013.01); *C12N 2770/24134* (2013.01); *C12N 2770/24232* (2013.01); *C12N 2770/24234* (2013.01); *C12N 2770/24271* (2013.01); *Y02A 50/386* (2018.01); *Y02A 50/388* (2018.01); *Y02A 50/39* (2018.01); *Y02A 50/394* (2018.01); *Y02A 50/466* (2018.01)

(58) Field of Classification Search
None
See application file for complete search history.

(56) References Cited

U.S. PATENT DOCUMENTS

| | | | |
|---|---|---|---|
| 8,258,275 | B2 | 9/2012 | Sallberg |
| 8,981,073 | B2 | 3/2015 | Mori |
| 2006/0128617 | A1 | 6/2006 | Kohara |
| 2009/0324584 | A1 | 12/2009 | Hoerr et al. |
| 2012/0021043 | A1 | 1/2012 | Kramps |

FOREIGN PATENT DOCUMENTS

| | | | |
|---|---|---|---|
| EP | 2071030 | A2 | 6/2009 |
| JP | 2009538603 | A | 11/2009 |
| JP | 2010029212 | A | 2/2010 |
| WO | 0075337 | A1 | 12/2000 |
| WO | 0075338 | A2 | 12/2000 |
| WO | 0075352 | A2 | 12/2000 |
| WO | 0183736 | A2 | 11/2001 |
| WO | 02052015 | A2 | 7/2002 |
| WO | 2004078974 | A1 | 9/2004 |
| WO | 2006110762 | A2 | 10/2006 |
| WO | 2007013882 | A2 | 2/2007 |
| WO | 2007140506 | A1 | 12/2007 |
| WO | 2008080091 | A2 | 7/2008 |
| WO | 2009022236 | A2 | 2/2009 |
| WO | 2009/095226 | A2 | 8/2009 |
| WO | 2009130588 | A2 | 10/2009 |
| WO | 2010037403 | A1 | 4/2010 |
| WO | 2011038737 | A1 | 4/2011 |
| WO | 2011039639 | A2 | 4/2011 |
| WO | 2011040535 | A | 4/2011 |
| WO | 2012046836 | A1 | 4/2012 |

OTHER PUBLICATIONS

John Walgren, Infection Ecology and Epidemiology, 2011, 1:6004, 7 pages. (Year: 2011).*
Alter, M.J., "Epidemiology of Hepatitis C Virus Infection," World Journal of Gastroenterology 13(17):2436-2441, May 2007.
Blight, K.J., "Highly Permissive Cell Lines for Subgenomic and Genomic Hepatitis C Virus RNA Replication," Journal of Virology 76(24):13001-13014, Dec. 2002.
Cui, S., et al., "The C-Terminal Regulatory Domain Is the RNA 5'-Triphosphate Sensor of RIG-I," Molecular Cell 29(2):169-179, Feb. 2008.

(Continued)

*Primary Examiner* — Stacy B Chen
(74) *Attorney, Agent, or Firm* — Christensen O'Connor Johnson Kindness PLLC

(57) ABSTRACT

Compositions and methods are provided that enable activation of innate immune responses through RIG-I like receptor signaling. The compositions and methods incorporate synthetic nucleic acid pathogen associated molecular patterns (PAMPs) that comprise elements initially characterized in, and derived from, the hepatitis C virus genome.

20 Claims, 27 Drawing Sheets

Specification includes a Sequence Listing.

(56) References Cited

OTHER PUBLICATIONS

Fischer, M., and Ehlers, M., "Toll-Like Receptors in Autoimmunity," Annals of the New York Academy of Sciences 1143:21-34, Nov. 2008.

Foy, E., et al., "Regulation of Interferon Regulatory Factor-3 by the Hepatitis C Virus Serine Protease," Science 300(5622):1145-1148, May 2003.

Fredericksen B.L., et al., "The Host Response to West Nile Virus Infection Limits Viral Spread Through the Activation of the Interferon Regulatory Factor 3 Pathway," Journal of Virology 78(14):7737-7747, Jul. 2004.

Friebe, P., and R. Bartenschlager, "Genetic Analysis of Sequences in the 3' Nontranslated Region of Hepatitis C Virus That Are Important for RNA Replication," Journal of Virology 76(11):5326-5338, Jun. 2002.

Friebe, P., et al. "Kissing-Loop Interaction in the 3' End of the Hepatitis C Virus Genome Essential for RNA Replication," Journal of Virology 79(1):380 392, Jan. 2005.

Gack, M., et al. "TRIM25 Ring-Finger E3 Ubiquitin Ligase Is Essential for RIG-I-Mediated Antiviral Activity," Nature 146(7138):916-920, Apr. 2007.

Gale, Jr., M. and Foy, E.M., "Evasion of Intracellular Host Defence by Hepatitis C Virus," Nature 436(7053):939-945, Aug. 2005.

Gale, Jr., M., "Effector Genes of Interferon Action Against Hepatitis C Virus," Hepatology 37(5):975-978, May 2003.

Horner, S.M., and Gale, Jr., M., "Intracellular Innate Immune Cascades and Interferon Defenses That Control Hepatitis C Virus," Journal of Interferon & Cytokine Research 29(9):489-498, Sep. 2009.

Horner, S.M., et al. "Mitochondrial-Associated Endoplasmic Reticulum Membranes (MAM) Form Innate Immune Synapses and Are Targeted by Hepatitis C Virus," Proceedings of the National Academy of Sciences USA 108(35):14590-14595, Aug. 2011.

Hornung, V., et al., "5'-Triphosphate RNA Is the Ligand for RIG-I," Science 314(5801):994-997, Nov. 2006.

Jiang, F., et al., "Structural Basis of RNA Recognition and Activation by Innate Immune Receptor RIG-I," Nature 479(7373):423-427, Sep. 2011. (Author Manuscript provided, PMCID: PMC3430514, available in PMC Aug. 29, 2012, 15 pages.).

Kageyama, M., et al. "55 Amino Acid Linker Between Helicase and Carboxyl Terminal Domains of RIG-I Functions as a Critical Repression Domain and Determines Inter-Domain Conformation," Biochemical and Biophysical Research communications 415(1):75-81, Nov. 2011.

Kato, H., et al. "Differential Roles of MDA5 and RIG-I Helicases in the Recognition of RNA Viruses," Nature 441(7089):101-105, May 2006.

Kawai, T., et al., "IPS-1, an Adaptor Triggering RIG-I- and Mda5-Mediated Type I Interferon Induction," Nature Immunology 6(10):981-988, Oct. 2005.

Kawasaki, T., et al., "Recognition of Nucleic Acids by Pattern-Recognition Receptors and Its Relevance in Autoimmunity," Immunological Reviews 243(1):61-73, Sep. 2011.

Keller, B.C., et al., "Resistance to Alpha/Beta Interferon Is a Determinant of West Nile Virus Replication Fitness and Virulence," Journal of Virology, 80(19):9424-9434, Oct. 2006.

Kowalinski, E., et al., "Structural Basis for the Activation of Innate Immune Pattern-Recognition Receptor RIG-I by Viral RNA," Cell 147(2):423-435, Oct. 2011.

Krieg, A.M., and Vollmer, J., "Toll-Like Receptors 7,8 and 9: Linking Innate Immunity to Autoimmunity," Immunological Reviews 220(1):251-269, Dec. 2007.

Loo, Y.M., and Gale, Jr., M. "Immune Signaling by RIG-I-Like Receptors," Immunity 34(5):680-692, May 2011.

Loo, Y.M., et al. "Viral and Therapeutic Control of IFN-Beta Promoter Stimulator 1 During Hepatitis C Virus Infection," Proceedings of the National Academy of Sciences USA 103(15):6001-6006, Apr. 2006.

Loo, Y.-M., et al., "Distinct RIG-I and MDA5 Signaling by RNA Viruses in Innate Immunity," Journal of Virology 82(1):335-345, Jan. 2008.

Lu, C. et al. "Crystal Structure of RIG-I C-Terminal Domain Bound to Blunt-Ended Double-Strand RNA Without 5' Triphosphate," Nucleic Acids Research 39(4):1565-1575, Mar. 2011.

Lu, C., et al., "The Structural Basis of 5' Triphosphate Double-Stranded RNA Recognition by RIG-I C-Terminal Domain," Structure 18(8):1032-1043, Aug. 2010.

Luo, D., et al., "Structural Insights Into RNA Recognition by RIG-I," Cell 147(2):409-422, Oct. 2011.

Marques, J.T., et al., "A Structural Basis for Discriminating Between Self and Nonself Double-Stranded RNAs in Mammalian Cells," Nature Biotechnology 24(5):559-565, May 2006.

Meylan, E., et al., "Cardif Is an Adaptor Protein in the RIG-I Antiviral Pathway and Is Targeted by Hepatitis C Virus," Nature 437(7062):1167-1172, Oct. 2005.

Milligan, J.F., et al., "Oligoribonucleotide Synthesis Using T7 RNA Polymerase and Synthetic DNA Templates," Nucleic Acids Research 15(21):8783-8798, Nov. 1987.

Myong, S., et al., "Cytosolic Viral Sensor RIG-I is a 5'-Triphosphate-Dependent Translocase on Double-Stranded RNA," Science 323(5917):1070-1074, Feb. 2009.

Pawlotsky, J.M., "Hepatitis C Virus Genetic Variability: Pathogenic and Clinical Implications," Clinics in Liver Disease 7(1):45-66, Feb. 2003.

Pawlotsky, J.M., "Hepatitis C Virus Resistance to Antiviral Therapy," Hepatology 32(5):889-896, Nov. 2000.

Pawlotsky, J.M., et al. "Interferon Resistance of Hepatitis C Virus Genotype 1b: Relationship to Nonstructural 5A Gene Quasispecies Mutations," Journal of Virology 72(4):2795-2805, Apr. 1998.

Pichlmair, A., et al., "RIG-I-Mediated Antiviral Responses to Single-Stranded RNA Bearing 5'-Phosphates," Science 314(5801):997-1001, Nov. 2006.

Saito, T., et al., "Innate Immunity Induced by Composition-Dependent RIG-I Recognition of Hepatitis C Virus RNA," Nature 454(7203):523-527, Jul. 2008. (Author Manuscript provided, PMCID: PMC 2856441, available in PMC Apr. 19, 2010, 10 pages.).

Saito, T., et al., "Regulation of Innate Antiviral Defenses Through a Shared Repressor Domain in RIG-I and LGP2," Proceedings of the National Academy of Sciences 104(2):582-587, Jan. 2007.

Schlee, M., et al., "Recognition of 5' Triphosphate by RIG-I Helicase Requires Short Blunt Double-Stranded RNA as Contained in Panhandle of Negative-Strand Virus," Immunity 31(1):25-34, Jul. 2009.

Schmidt, A., et al. "5'-Triphosphate RNA Requires Base-Paired Structures to Activate Antiviral Signaling via RIG-I," Proceedings of the National Academy of Sciences USA 106(29):12067-12072, Jul. 2009.

Schnell, G., et al., "Uridine Composition of the Poly-U/UC Tract of HCV RNA Defines Non-Self Recognition by RIG-I," PLoS Pathogens 8(8):e1002839, Aug. 2012, 13 pages.

Seth, R.B., et al., "Identification and Characterization of MAVS, a Mitochondrial Antiviral Signaling Protein That Activates NF-kappaB and IRF 3," Cell 122(5):669-682, Sep. 2005.

Shepard, C.W., et al., "Global Epidemiology of Hepatitis C Virus Infection," The Lancet Infectious Diseases 5(9):558-567, Sep. 2005.

Stepinski, J., et al., "Synthesis and Properties of mRNAs Containing the Novel "Anti-Reverse" Cap Analogs 7-methy (39-O-methyl)GpppG and 7-methyl(39-deoxy)GpppG," RNA 7(10):1486-1495, Oct. 2001.

Sumpter, R., Jr., et al., "Regulating Intracellular Antiviral Defense and Permissiveness to Hepatitis C Virus RNA Replication Through a Cellular RNA Helicase, RIG-I," Journal of Virology 79(5)2689-2699, Mar. 2005.

Suthar, M.S., et al., "Infectious Clones of Novel Lineage 1 and Lineage 2 West Nile Virus Strains WNV-TX02 and WNV-Madagascar," Journal of Virology 86(14):7704-7709, Jul. 2012.

Suthar, M.S., et al., "IPS-1 Is Essential for the Control of West Nile Virus Infection and Immunity," PLoS Pathogens 6(2):e1000757, Feb. 2010, 15 pages.

(56) References Cited

OTHER PUBLICATIONS

Takahasi, K., et al., "Nonself RNA-Sensing Mechanism of RIG-I Helicase and Activation of Antiviral Immune Responses," Molecular Cell 29(4):428-440, Feb. 2008.
Third-Party Letter mailed Oct. 28, 2016, to Thomas S. Nowak, regarding U.S. Appl. No. 14/327,439, filed Jul. 9, 2014, 8 pages; Applicant makes no assertion as to the accuracy of any statement made in this letter.
Uzri, D., and L. Gehrke, "Nucleotide Sequences and Modifications That Determine RIG-I/RNA Binding and Signaling Activities," Journal of Virology 83(9):4174-4184, May 2009.
Wakita, T., et al., "Production of Infectious Hepatitis C Virus in Tissue Culture From a Cloned Viral Genome," Nature Medicine 11(7):791-796, Jul. 2005.
Wang, Y., et al., "Structural and Functional Insights Into 5'-ppp RNA Pattern Recognition by the Innate Immune Receptor RIG-I," Nature Structural & Molecular Biology 17(7):781-787, Jul. 2010.
Wasley, A. and Alter, M.J., "Epidemiology of Hepatitis C: Geographic Differences and Temporal Trends," Seminars in Liver Disease 20(1):1-16, 2000.
Xu, L-G, et al., "VISA Is an Adapter Protein Required for Virus-Triggered IFN Beta Signaling," Molecular Cell 19(6):727-740, Sep. 2005.
Yi, M., and Lemon, S.M., "3' Nontranslated RNA Signals Required for Replication of Hepatitis C Virus RNA," Journal of Virology 77(6):3557-3568, Mar. 2003.
Yoneyama, M., et al., "The RNA Helicase RIG-I Has an Essential Function in Double-Stranded RNA-Induced Innate Antiviral Responses," Nature Immunology 5(7):730-737, Jul. 2004.
Yoneyama, M., et al., "Shared and Unique Functions of the DExD/H-Box Helicases RIG-I, MDA5, and LGP2 in Antiviral Innate Immunity," Journal of Immunology 175(5):2851-2858, Sep. 2005.
You, S., and C.M. Rice, "3' RNA Elements in Hepatitis C Virus Replication: Kissing Partners and Long Poly(U)," Journal of Virology 82(1):184-195, Jan. 2008.
Zhong, J., et al., "Robust Hepatitis C Virus Infection In Vitro," Proceedings of the National Academy of Sciences USA 102(26):9294-9299, Jun. 2005.
Gen Bank Accession No. AB080299.1, submitted 2002.
Kishine et al., Biochemical and Biophysical Research Communications, 2002, 293(3):993-999.

\* cited by examiner

| RNA Construct | EC$_{10}$ | EC$_{50}$ | EC$_{90}$ | Signaling |
|---|---|---|---|---|
| X-region | N/A | N/A | N/A | None |
| X-region-U34 | 1.42 | 7.26 | >30 | Med. |
| Con1 pU/UC | 1.13 | 3.45 | 10.18 | High |
| JFH1 pU/UC | 0.83 | 3.17 | 11.59 | High |
| Δcore | 3.04 | 7.31 | 17.10 | None/Low |
| U8core | 2.74 | 6.73 | 16.06 | None/Low |
| U17core | 0.94 | 4.29 | 18.71 | Med. |
| poly-U 62 | N/A | N/A | N/A | Low |
| poly-U 62-C | 0.65 | 2.28 | 7.73 | High |
| pU/UC C67U | <4 | <4 | >10 | High |
| pU/UC 3'C26 | <4 | <4 | >10 | Med. |
| pU/UC C26 | <4 | <4 | >10 | High |
| poly-U 107 | <4 | >4, <6 | >10 | High |
| pU/UC 62 | <4 | <4 | >10 | Med. |
| 5'C | <4 | <4 | >10 | Med. |
| 3'C | <4 | >4, <6 | >10 | Low |
| U/C1 | <4 | <4 | >8, <10 | Med. |
| U/C2 | <4 | <4 | >6, <8 | Med. |
| U/C3 | <4 | <4 | >8, <10 | Med. |
| U/C4 | <4 | <4 | >4, <6 | Med. |
| U/C5 | <4 | >6, <8 | >10 | Low |
| U/C6 | <4 | >4, <6 | >10 | Low |
| U/C7 | <4 | >10 | >10 | Low |
| U/C8 | <4 | >8, <10 | >10 | Low |

*FIG. 2C*

METHODS AND COMPOSITIONS FOR ACTIVATION OF INNATE IMMUNE RESPONSES THROUGH RIG-I LIKE RECEPTOR SIGNALING

CROSS-REFERENCES TO RELATED APPLICATIONS

This application is a division of U.S. patent application Ser. No. 14/327,439, filed Jul. 9, 2014 (now U.S. Pat. No. 9,775,894), which claims the benefit of U.S. Provisional Application No. 61/844,022, filed Jul. 9, 2013, both of which applications are incorporated herein by reference in their entirety.

STATEMENT OF GOVERNMENT LICENSE RIGHTS

This invention was made with Government support under Grants AI100384, DA024563, AI088778, and AI060389 awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 64256_ST25.txt. The text file is 26 KB; was created on Sep. 21, 2017; and is being submitted via EFS-Web with the filing of the specification.

BACKGROUND

The innate immune system is often the first line of defense against colonization and/or proliferation by invading pathogens, such as viruses and bacteria. The innate immune system comprises cells and circulating components that, upon detection of a non-self entity (such as a pathogen) within the body, can act non-specifically to counter the invasion. Various effects of the innate response can include the recruitment of phagocytic cells to sites of infections through production of chemokines and the promotion of inflammation. Additionally, the innate response can include the activation of serum complement factors to damage pathogen membranes. Moreover, the innate response can include the production of cytokines, such as interferons, to induce antiviral states of uninfected cells. For example, the rapid production of alpha/beta interferon (IFN $\alpha/\beta$) leads to the induced expression of hundreds of interferon-stimulated genes (SGs) whose products direct anti-pathogen and immunomodulatory actions that can counter-act infections. While the mechanisms of the innate system are generally non-specific and short-lived, the innate immune system also cross-activates elements of the adaptive immune system, which can respond to specific foreign antigens through the antigen-specific interactions of antibodies and TCR receptors. For example, macrophages that encounter foreign pathogens can produce various cytokines that contribute to the activation of various components of the adaptive immune system.

Appropriate innate immune responses only occur upon detection of non-host pathogens and limit the severity of the response to avoid undue damage to healthy host tissue (e.g., avoid septic shock). Non-host pathogens can be detected by the discrimination between host (self) and non-self antigens. Various classes of pathogens, such as viruses and bacteria, contain pathogen-associated molecular patterns (PAMPs) in structural or genetic components that are not exhibited by host organisms. Most mammalian cells have receptors that recognize PAMPS called pattern recognition receptors (PRRs), which, when bound to the appropriate PAMPs will signal the presence of non-host organisms. However, considering the general, non-specific response of the innate immune systems, accurate and appropriate activation of the innate response to pathogen patterns instead of host patterns is essential to avoid causing damage to host tissues. Furthermore, the appropriate degree of innate response is also critical because innate responses are not antigen specific and damage to host tissue can result from overstimulation. Such damage can be more costly to the host organism than the infection itself. In extreme cases, hosts can experience septic shock when the innate immune system is overstimulated.

Identifying PAMPs that induce innate immune response can be useful to serve as anti-microbial therapeutics, such as adjuvants in combating or preventing infections, and to enhance the efficacy of more traditional vaccine therapeutics. Accordingly, there is a need to identify pathogen-associated molecular patterns (PAMPs) that can stimulate an appropriate and effective innate immune response to a pathogen but that can avoid costly damage to tissues of the host organism. The compositions and methods of the present disclosure address this and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a synthetic nucleic acid pathogen-associated molecular pattern (PAMP). In one embodiment, the synthetic nucleic acid PAMP comprises a 5'-arm region, a poly-uracil core, and a 3'-arm region.

In one embodiment, the 5'-arm region comprises a terminal triphosphate. In one embodiment, the 5'-arm region further comprises one or more nucleic acid residues disposed between the terminal triphosphate and the poly-uracil core.

In one embodiment, the poly-uracil core comprises at least 8 contiguous uracil residues. In one embodiment, the poly-uracil core consists of between 8 and 30 uracil residues.

In one embodiment, the 3' arm region comprises at least 8 nucleic acid residues. In one embodiment, the 5' most nucleic acid residue of the 3' arm region is not a uracil and the 3' arm region is at least 30% uracil residues. In one embodiment, the 5'-most nucleic acid residue of the 3'-arm region is a cytosine residue or a guanine residue. In one embodiment, the 3'-arm region is at least 40%, 50%, 60%, 70%, 80%, or 90% uracil residues. In one embodiment, the 3'-arm region comprises at least 7 contiguous uracil residues.

In one embodiment, the terminal triphosphate, the one or more nucleic acid residues of the 5'-arm region, and the poly-uracil core do not naturally occur together in a Hepatitis C virus.

In one embodiment, the synthetic nucleic acid PAMP is capable of inducing retinoic acid-inducible gene I (RIG-I)-like receptor (RLR) activation. In one embodiment, the RLR is RIG-I.

In another aspect, the disclosure provides a pharmaceutical composition. In one embodiment, the pharmaceutical composition comprises the synthetic nucleic acid PAMP described herein and an acceptable carrier. In one embodiment, the pharmaceutical composition further comprises a viral antigen, a bacterial antigen, a protozoal antigen, a fungal antigen, and/or a helminth antigen, or an attenuated, inactivated, or killed virus, bacterium, protozoan, fungus, and/or helminth. In one embodiment, the pharmaceutical composition further comprises an anti-viral therapeutic, an anti-bacterial therapeutic, an anti-protozoal therapeutic, an anti-fungal therapeutic, an anti-helminth therapeutic, and/or an adjuvant.

In another aspect, the disclosure provides a method of inducing retinoic acid-inducible gene I (RIG-I)-like receptor (RLR) signaling in a cell. In one embodiment, the method comprises administering to the cell an effective amount of the synthetic nucleic acid PAMP described herein.

In another aspect, the disclosure provides a method of treating a condition in a subject treatable by inducing RLR signaling. In one embodiment, the method comprises administering to the subject an effective amount of the pharmaceutical composition described herein.

In another aspect, the disclosure provides a method of inducing an innate immune response in a subject. In one embodiment, the method comprises administering to the subject an effective amount of the pharmaceutical composition described herein.

In another aspect, the disclosure provides a method of treating a viral, bacterial, protozoal, fungal, and/or helminth infection in a subject. In one embodiment, the method comprises administering to the subject an effective amount of the pharmaceutical composition described herein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

(FIG. 1A) Induction of the IFN-β-promoter in Huh7 cells transfected with equal moles of tRNA, full-length JFH1, JFH1 pU/UC, or Con1 pU/UC RNA. IFN-β-promoter luciferase activity is shown as mean IFN-β fold index (compared to cells with No RNA, ±s.d. for three replicates). Huh7 cells were transfected with the various RNA constructs and 16 hours later cells were harvested for dual luciferase activity. Asterisks indicate a significant difference compared to No RNA control as determined by a one-way ANOVA adjusted with Bonferroni's multiple comparison test ($*P<0.05$, $P<0.01$, $*P<0.001$). (FIG. 1B) Induction of the IFN-β-promoter in Huh7 or Huh7.5 cells transfected with 350 ng of the indicated RNA constructs (described in more detail in Example 1). IFN-β-promoter luciferase activity is shown as the mean IFN-β fold index±s.d. for three replicates, and data was normalized to the No RNA control. Cells were harvested for dual luciferase activity 16 hours post-RNA transfection. Asterisks indicate a significant difference compared to No RNA control as determined by a one-way ANOVA adjusted with Bonferroni's multiple comparison test ($*P<0.05$, $**P<0.001$). (FIG. 1C) The abundance of phospho-IRF-3 (Ser396), total IRF-3, RIG-I, ISG56, and tubulin were measured by immunoblot. Huh7 cells were transfected with the indicated RNA constructs and cells were harvested for protein analysis 16 hours later. RIG-I and ISG56 are IFN-β-stimulated genes. The ratio of phospho-IRF-3/total IRF-3 was calculated by measuring the relative immunoblot band intensities using ImageJ software (NIH). Data shown in all panels are representative of three independent experiments.

FIGS. 2A-2C illustrate the differential binding between poly-U/UC RNA constructs and purified RIG-I protein in vitro. (FIG. 2A) EMSA gel-shift assays: RNA (10 pmol) was incubated with increasing concentrations of purified recombinant RIG-I protein (0-30 pmol), then complexes were separated on native agarose gels and RNA was visualized using SYBR Gold nucleic acid stain. Unshifted RNA, U; shifted RNA/protein complex, S; supershifted RNA/protein complex, ss. (FIG. 2B) RIG-I/RNA binding curves were generated from the gel-shift analyses and plotted for the X-region, X-region-U34, Con1 pU/UC, JFH1 pU/UC, Δcore, U8core, U17core, and poly-U 62-C RNAs. Due to poor band formation of the poly-U 62 RNA on the non-denaturing gel used in our EMSA, a gel-shift analysis of this particular RNA could not be conducted. (FIG. 2C) Table comparing the effective pmol concentration of RIG-I required to shift 10% ($EC_{10}$), 50% ($EC_{50}$), or 90% ($EC_{90}$) of each RNA construct. RIG-I signaling for each RNA construct was determined in FIG. 1B, and the magnitude of the signaling activity is listed in the table as either None/Low (IFN-β fold index=0-3), Low (IFN-β fold index=3-30), Med. (IFN-β fold index=30-100), or High (IFN-b fold index>100). N/A=Not applicable.

(FIG. 3A) Limited-trypsin proteolysis of 30 pmol purified RIG-I with increasing amounts of RNA. Repressor domain, RD; helicase domain and CARDs, Helic. +CARDs. (FIG. 3B) Limited trypsin proteolysis of 30 pmol purified RIG-I protein with 1.0 pmol of each indicated RNA construct. RIG-I digestion products were separated on the same gel and relative band intensities (listed as % of total) were measured using ImageJ gel imaging software (NIH). (FIG. 3C) ATPase activity of purified RIG-I protein incubated with increasing amounts of RNA. Data shown are means±s.d. for two replicates.

(FIG. 4A) Huh7 cells were transfected with the indicated poly-U/UC RNA constructs 12 hours prior to HCV infection (MOI=0.1), and virus production was assessed 48 hours post-infection. Data shown are means±s.d. for three replicates. Asterisks indicate a significant difference compared to No RNA control as determined by a one-way ANOVA adjusted with Bonferroni's multiple comparison test ($*P<0.001$, $**P≤0.0001$). (FIG. 4B) Wild-type mice (n=2) received 200 μg of X-region RNA, X-region-U34 RNA, Con1 pU/UC RNA, or Δcore RNA. Mock-transfected wild-type mice (n=1) received PBS. Comparative measurements of hepatic mRNA and protein expression were measured 8 hours post-transfection. Real-time quantitative PCR was performed to examine expression of IFN-β, CCL5, Ifit2, ISG15, and GAPDH. Results were normalized to the expression of mouse GAPDH mRNA, and mRNA fold index was normalized to Mock controls. See the left panel for IFN-β and CCL5 expression and the right panel for Ifit2 and ISG15 expression. Data shown are means±s.d. for two replicates, and gene expression data was confirmed by two independent real-time PCR analyses. Asterisks indicate a significant difference as determined by a one-way ANOVA adjusted with Bonferroni's multiple comparison test ($*P<0.05$, $P<0.01$, $*P<0.001$). (FIG.

4C) Following RNA transfection, mouse livers were recovered and immunohistochemistry staining was conducted for mouse ISG54. The black scale bar indicates a distance of 500 mm.

Figure 5A:
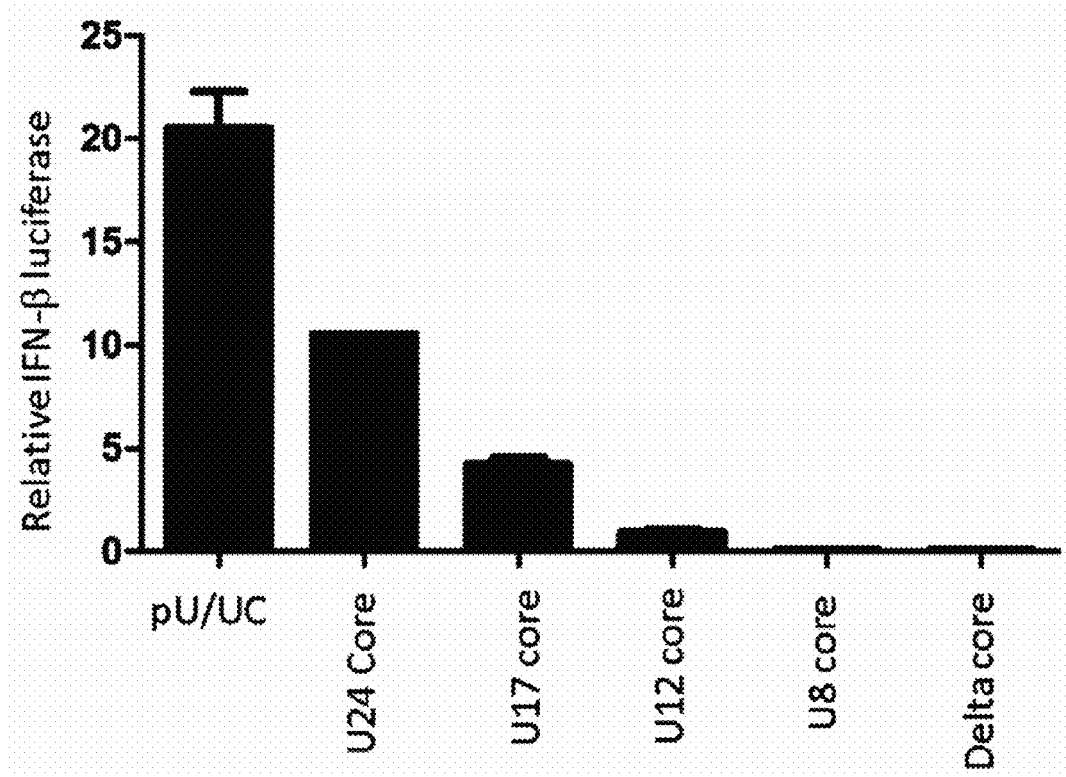
Figure 5B:
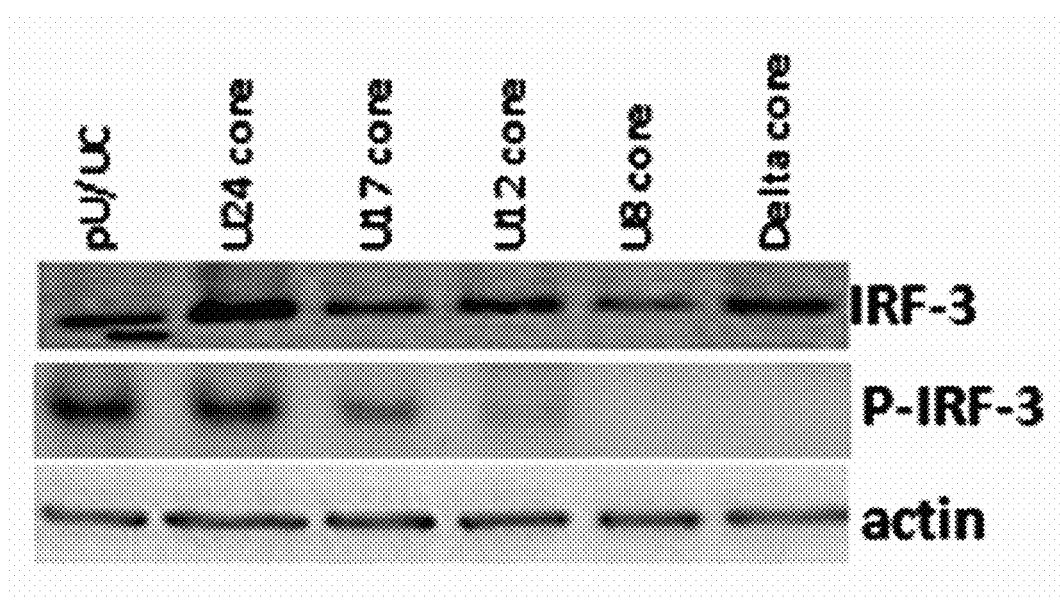

FIGS. 5A and 5B illustrates that IFN-beta promoter is induced by poly-U/UC, U12, U17, and U24 core RNA constructs. Interferon-beta luciferase activity was measured in Huh7 cells transfected with $10^5$ cells were co-transfected with 200 ng of the indicated RNA construct derived from HCV (Con1 strain), along with IFN-beta luc reporter promoter plasmid. Cells were harvested 16 hrs later. FIG. 5A illustrates the relative IFN-β luciferase activity stimulated by the various RNA constructs. FIG. 5B illustrates an immunoblot of cells harvested in parallel and assayed for abundance of total IRF-3, Phospho-IRF-3 (P-IRF-3), and actin.

Figure 6:
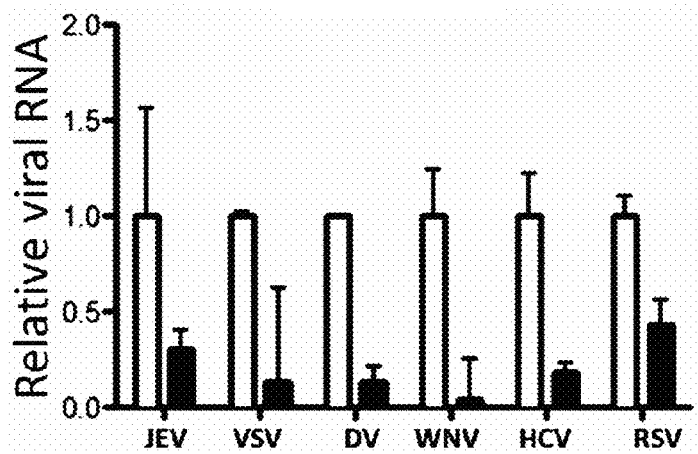

FIG. 6 illustrates the antiviral activity of the poly-U/UC PAMP RNA construct. Abbreviations: JEV, Japanese encephalitis virus; VSV, vesicular stomatitis virus; DV, dengue virus 2; WNV, West Nile virus; HCV, hepatitis C virus; RSV, respiratory syncytial virus. The graph shows viral load in cultured Huh7 (human hepatoma) cultures treated with transfection reagent alone (white) and in cultures transfected with poly-U/UC RNA (black). Cells were infected with virus at MOI=1.0, and after 3 hrs were treated as indicated. Cells were harvested at 72 hours post-treatment and intracellular viral RNA levels measured by virus-specific reverse transcriptase-quantitative PCR (RT-qPCR) assay. Bars show intracellular viral RNA levels compared to transfection reagent control. Error bars show standard error of the mean across 6 experiments. Differences between each control and poly-U/UC bar set are significant ($P<0.03$) based on Student's T-test. This demonstrates that the poly-U/UC RNA construct has antiviral activity.

Figure 7:
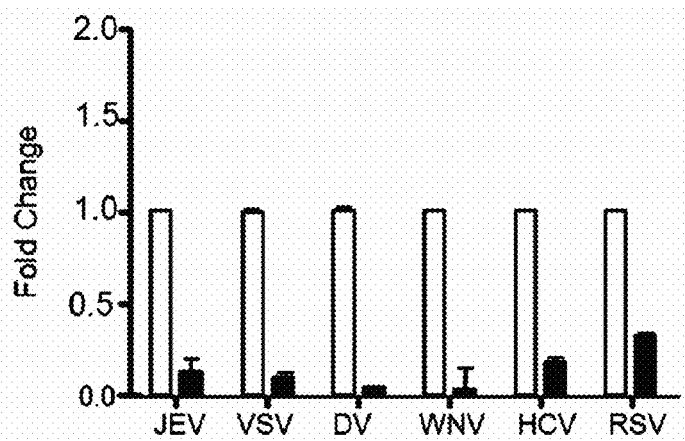

FIG. 7 illustrates the antiviral activity of U17 core PAMP RNA construct. Abbreviations: JEV, Japanese encephalitis virus; VSV, vesicular stomatitis virus; DV, dengue virus 2; WNV, West Nile virus; HCV, hepatitis C virus; RSV, respiratory syncytial virus. The graph shows viral load in cultured Huh7 (human hepatoma) cultures treated with transfection reagent alone (white) and in cultures transfected with the U17 core derivative of the poly-U/UC RNA PAMP (black). Cells were infected with virus at MOI=1.0, and after 3 hrs were treated as indicated. Cells were harvested at 72 hours post-treatment and intracellular viral RNA was measured by virus-specific RT-qPCR assay. Bars show intracellular viral RNA level compared to control. Error bars show standard error of the mean across 4 experiments. Differences between each control and U17 core RNA bar set are significant ($P<0.01$) based on Student's T-test. This demonstrates that the U17 core RNA has antiviral activity.

Figure 8:
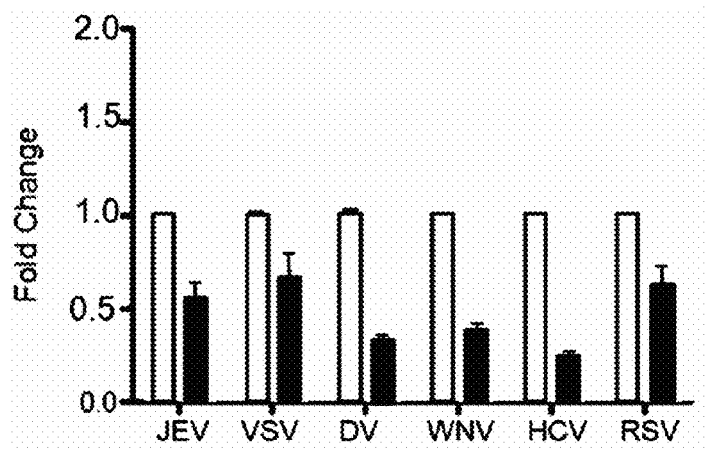

FIG. 8 illustrates the antiviral activity of U12 core PAMP RNA construct. Abbreviations: JEV, Japanese encephalitis virus; VSV, vesicular stomatitis virus; DV, dengue virus 2; WNV, West Nile virus; HCV, hepatitis C virus; RSV, respiratory syncytial virus. The graph shows viral load in cultured Huh7 (human hepatoma) cultures treated with transfection reagent alone (white) and in cultures transfected with the U12 core derivative of the poly-U/UC RNA PAMP (black). Cells were infected with virus at MOI=1.0, and after 3 hrs were treated as indicated. Cells were harvested at 72 hours post-treatment and intracellular viral RNA was measured by virus-specific RT-qPCR assay. Bars show intracellular viral RNA level compared to control. Error bars show standard error of the mean across 3 experiments. Differences between each control and U12 core RNA bar set are significant ($P<0.05$) based on Student's T-test. This demonstrates that the U12 core RNA has antiviral activity.

Figure 9A:
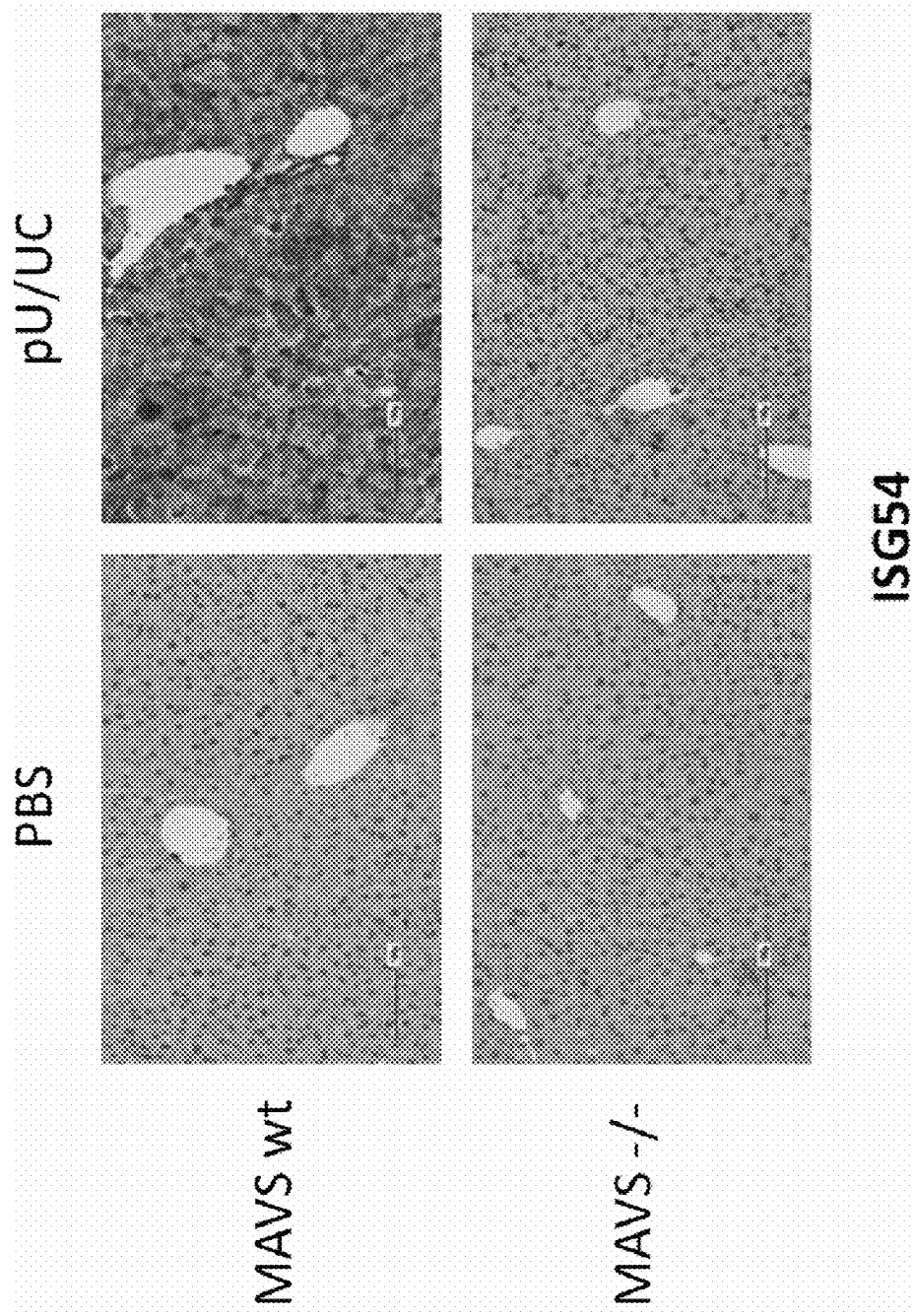
Figure 9B:
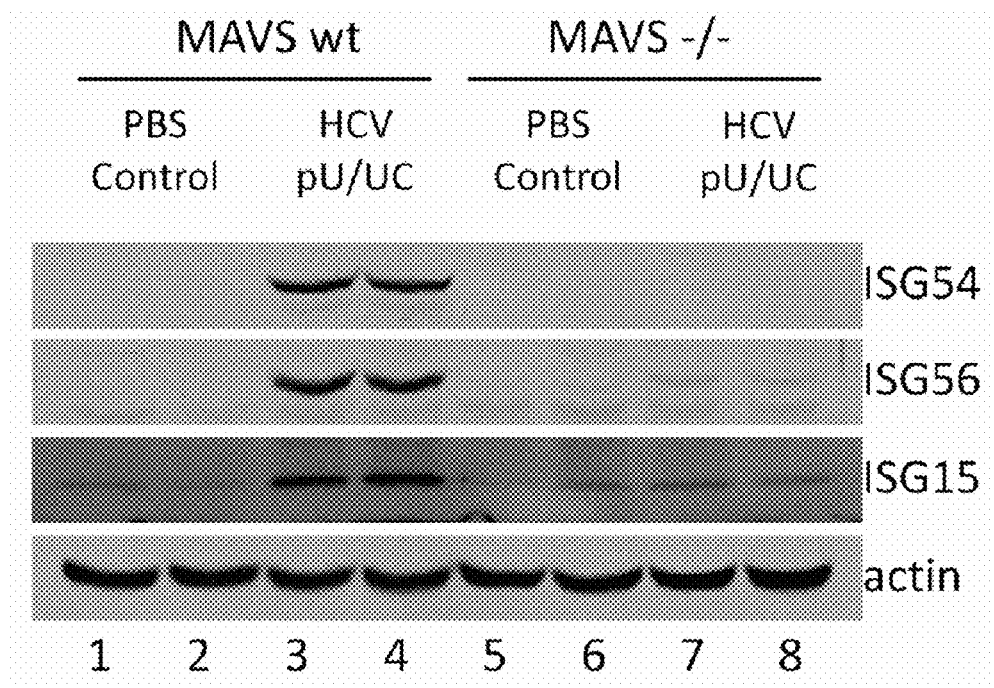
Figure 9C:
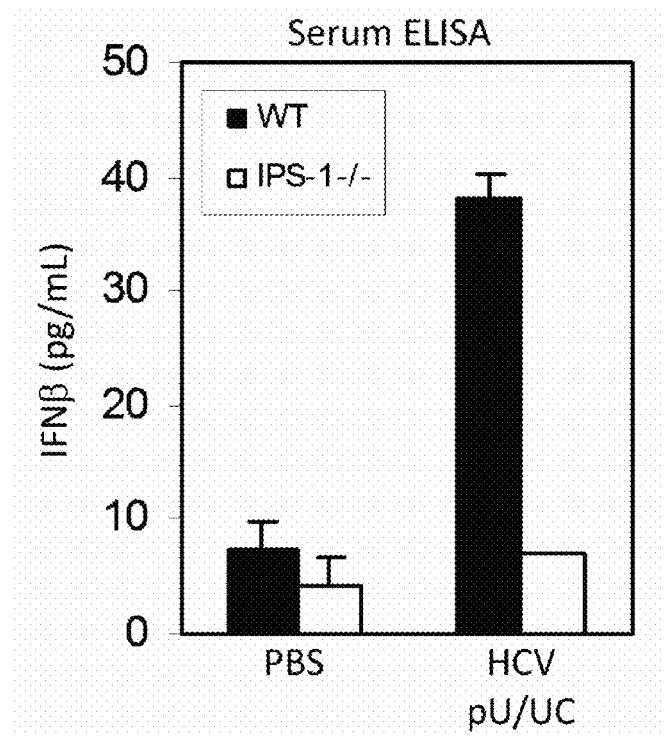

FIGS. 9A-9C illustrate that injection of polyU/UC RNA induces the innate immune response in vivo through MAVS/RLR-mediated signaling. 200 mg polyU/UC RNA or PBS control was administered to wildtype and MAVS-/-mice (MAVS-/-mice lack the MAVS adaptor protein that mediates RIG-I-like receptor (RLR) signaling) by hydrodynamic IV injection in the tail vein or IP. Mice were euthanized 8 hrs later and assessed for (FIG. 9A) ISG54 expression in the liver by immunohistochemistry, (FIG. 9B) innate immune antiviral gene induction in the liver by immunoblot and (FIG. 9C) IFNb levels in the sera by ELISA.

Figure 10:
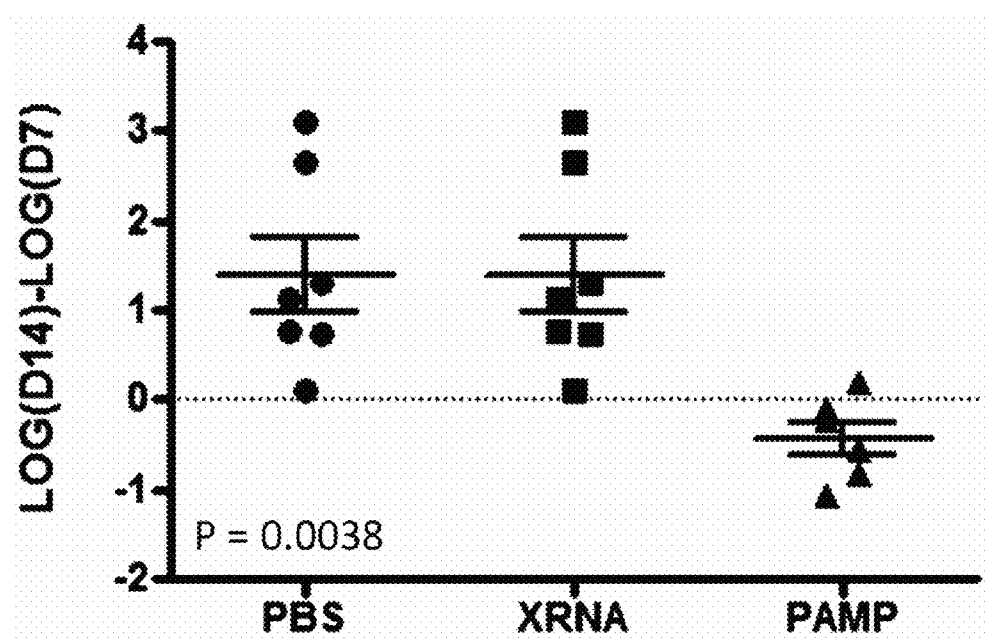

FIG. 10 illustrates that HCV polyU/UC RNA treatment reduces HCV viral burden in vivo. SCID/beige-Alb/uPA chimeric mice were transplanted with human primary hepatocytes derived from cryopreserved stocks purchased from CellDirect Inc. Human hepatocyte repopulation levels were verified at 4 and 8 weeks after transplantation by measuring human albumin levels by ELISA. Chimeric animals with human albumin concentrations greater than or equal to 1000 mg/mL received a single intravenous injection of 100 mL HCV-positive patient serum (HCV genotype 2b, $1.38\times10^5$ genome equivalents per animal). Mice were administered PBS alone or 150 mg polyU/UC (PAMP) RNA or control xRNA by hydrodynamic IV injections via the tail vein at days 11, 13 and 15 post-infection. Infected mice were bled at days 7 (pre-treatment baseline) and 14 post-infection for viremia measurements of HCV genomic RNA by qPCR. Shown here is difference in viral burden (log scale) in the sera compared to the day 7 baseline.

Figure 11B:
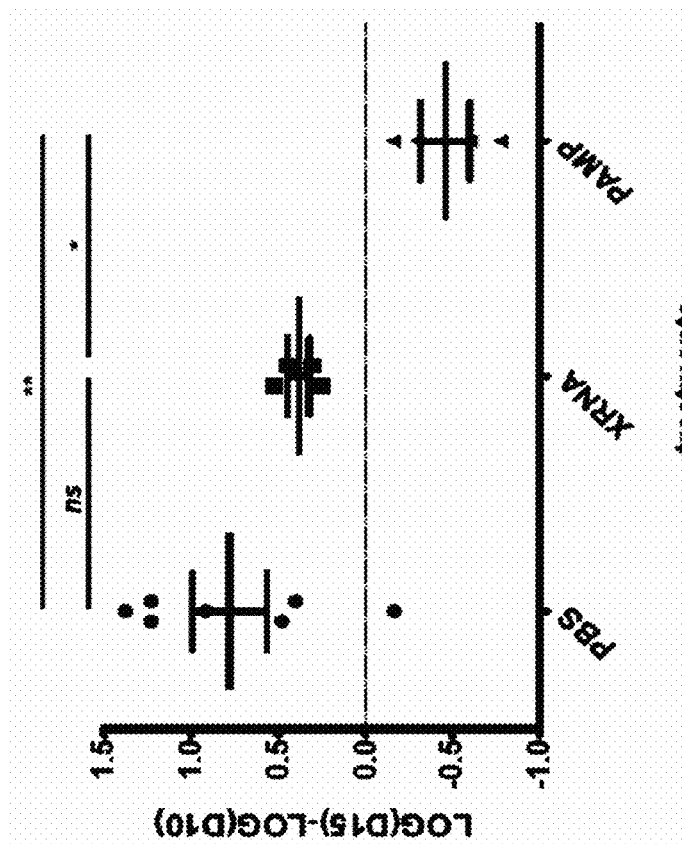
Figure 11A:
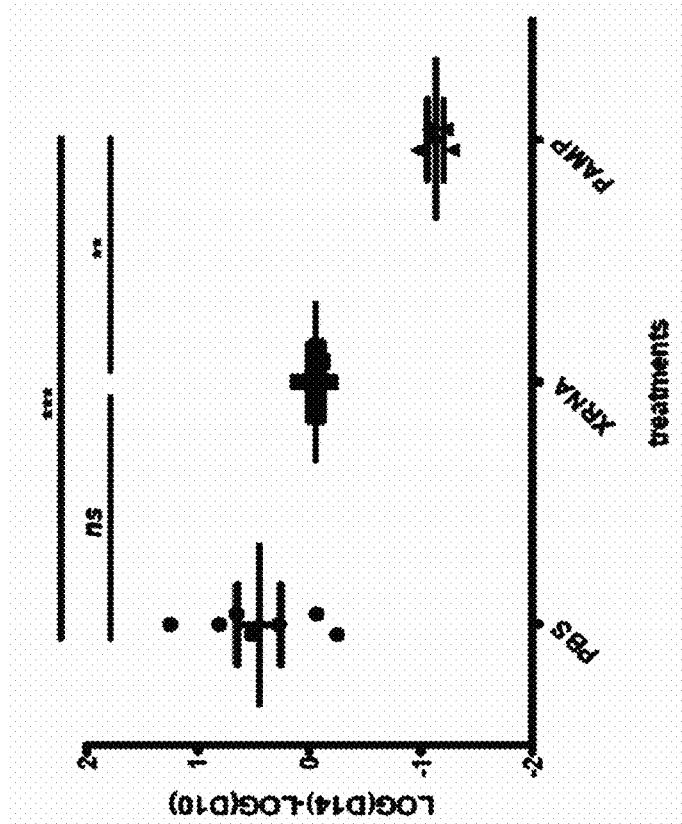

FIGS. 11A-11B illustrate that HCV polyU/UC RNA treatment reduces HCV viral burden in vivo. SCID/beige-Alb/uPA chimeric mice were transplanted with human primary hepatocytes derived from cryopreserved stocks purchased from CellDirect Inc. Human hepatocyte repopulation levels were verified at 4 and 8 weeks after transplantation by measuring human albumin levels by ELISA. Chimeric animals with human albumin concentrations greater than or equal to 1000 mg/mL received a single intravenous injection of 100 mL HCV-positive patient serum (HCV genotype 2b, $1.38\times10^5$ genome equivalents per animal). Mice were administered PBS alone or 150 mg polyU/UC (PAMP) RNA or control xRNA by hydrodynamic IV injections via the tail vein at days 11, 13, and 15 post-infection. Infected mice were bled at days 10 (pre-treatment baseline) and at days 14 and 15 post-infection for viremia measurements of HCV genomic RNA by qPCR. Illustrated here are differences in viral burden (log scale) in the sera on day 14 (FIG. 11A) and day 15 (FIG. 11B) compared to the day 10 baseline.

Figure 12:
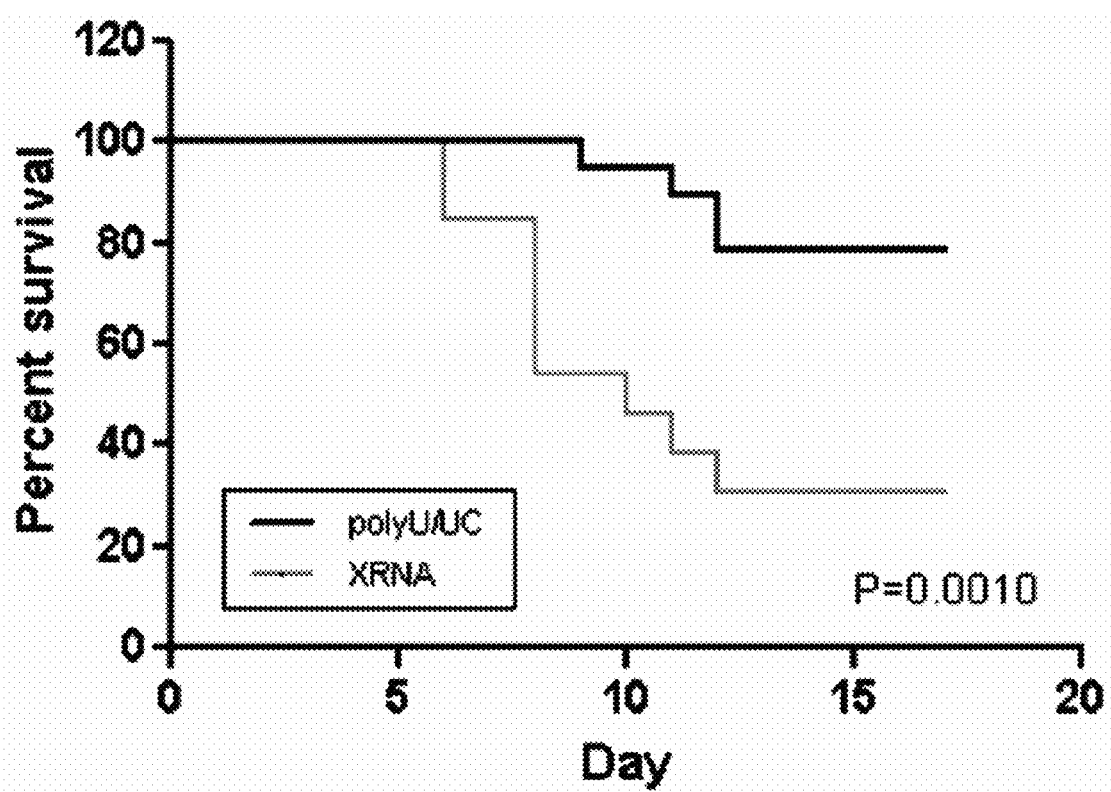

FIG. 12 illustrates that polyU/UC RNA, but not xRNA treatment, protects mice against disease from West Nile virus (WNV) infection. C57Bl6 mice were infected via subcutaneous injection of the left footpad with 1000 pfu WNV (Tx-02). At days 1.5, 3, and 5, mice were given 100 mg polyU/UC RNA or control xRNA by IP. Mice were monitored daily for body weight and clinical scores. Mice that lose greater than or equal to 20% body weight or that exhibit clinical symptoms greater than 5 were euthanized according to UW IACUC protocols. The graph shows percent survival/morbidity curve for mice over a course of 17 days post-infection. This demonstrates that poly-U/UC RNA provides therapeutic protection against WNV infection.

Figure 13A:
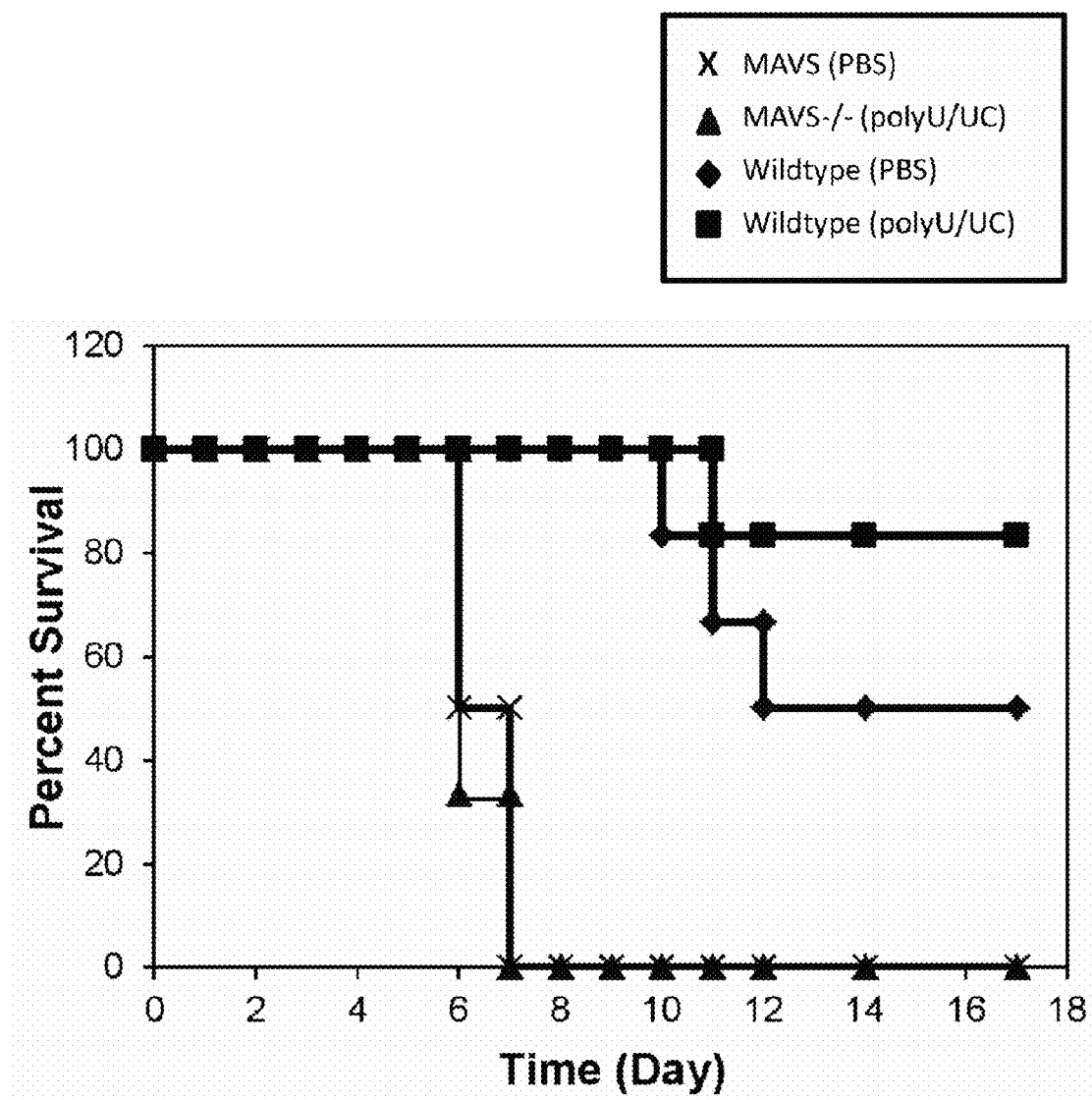
Figure 13B:
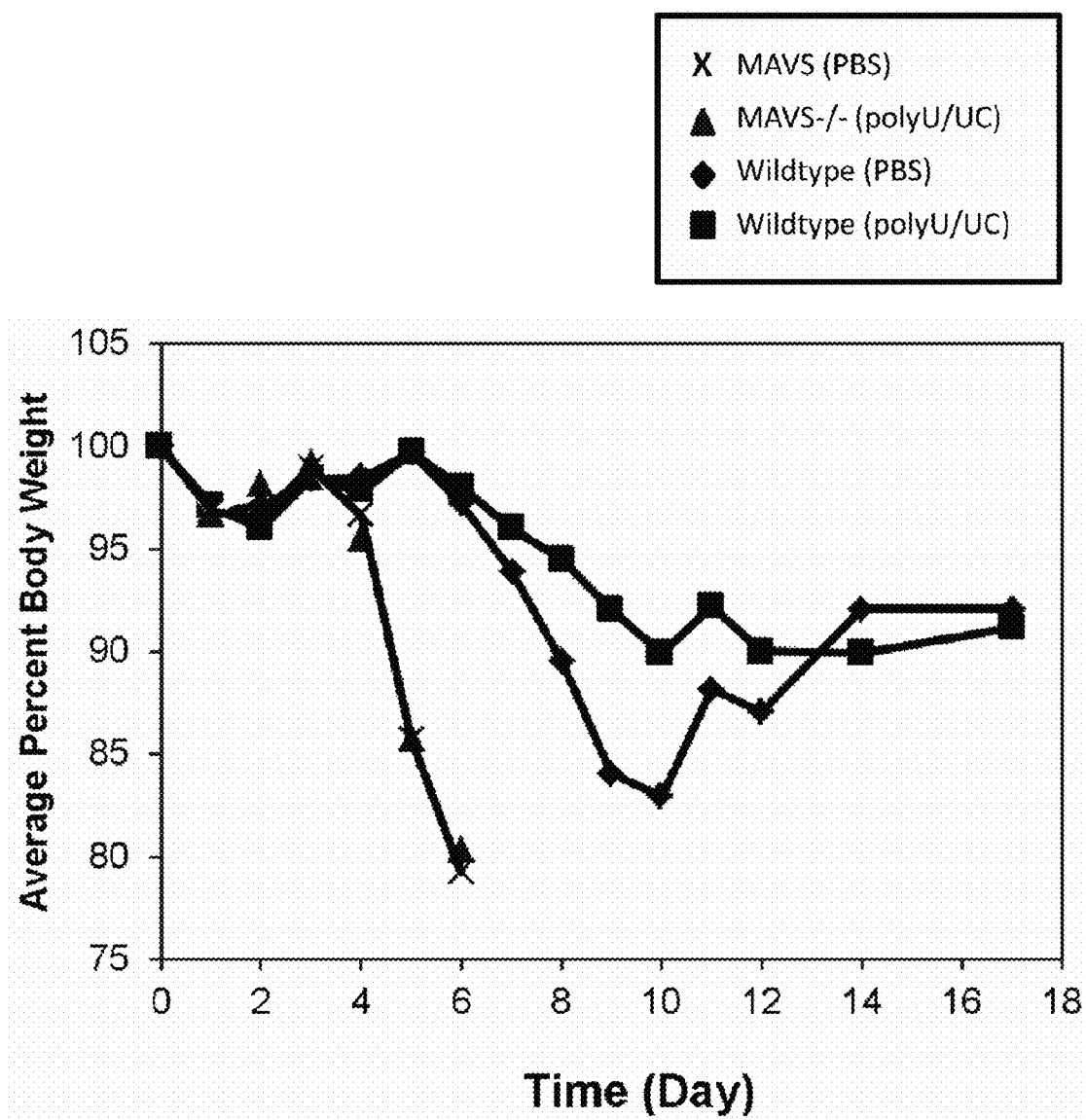
Figure 13C:
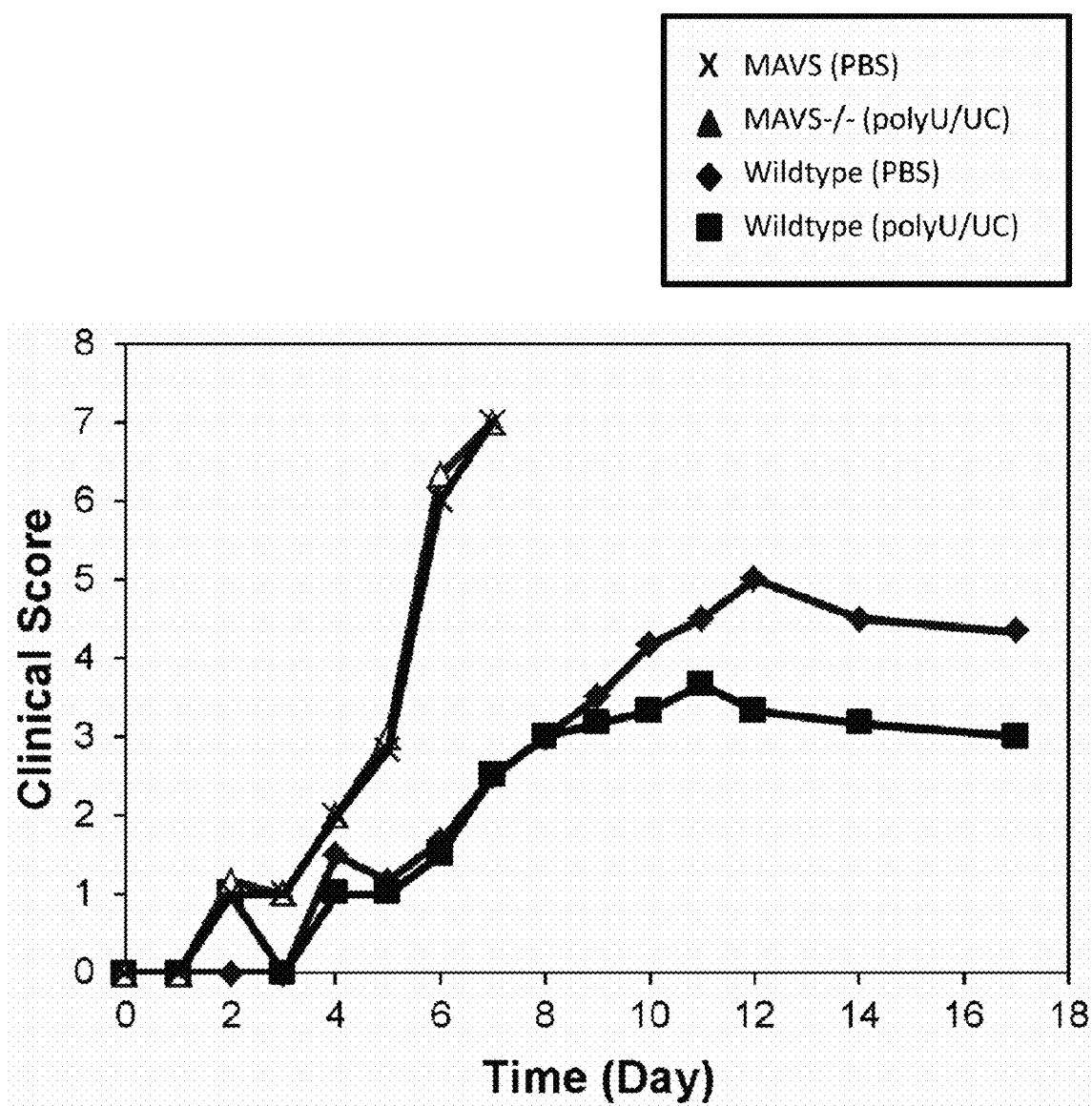
Figure 13D:
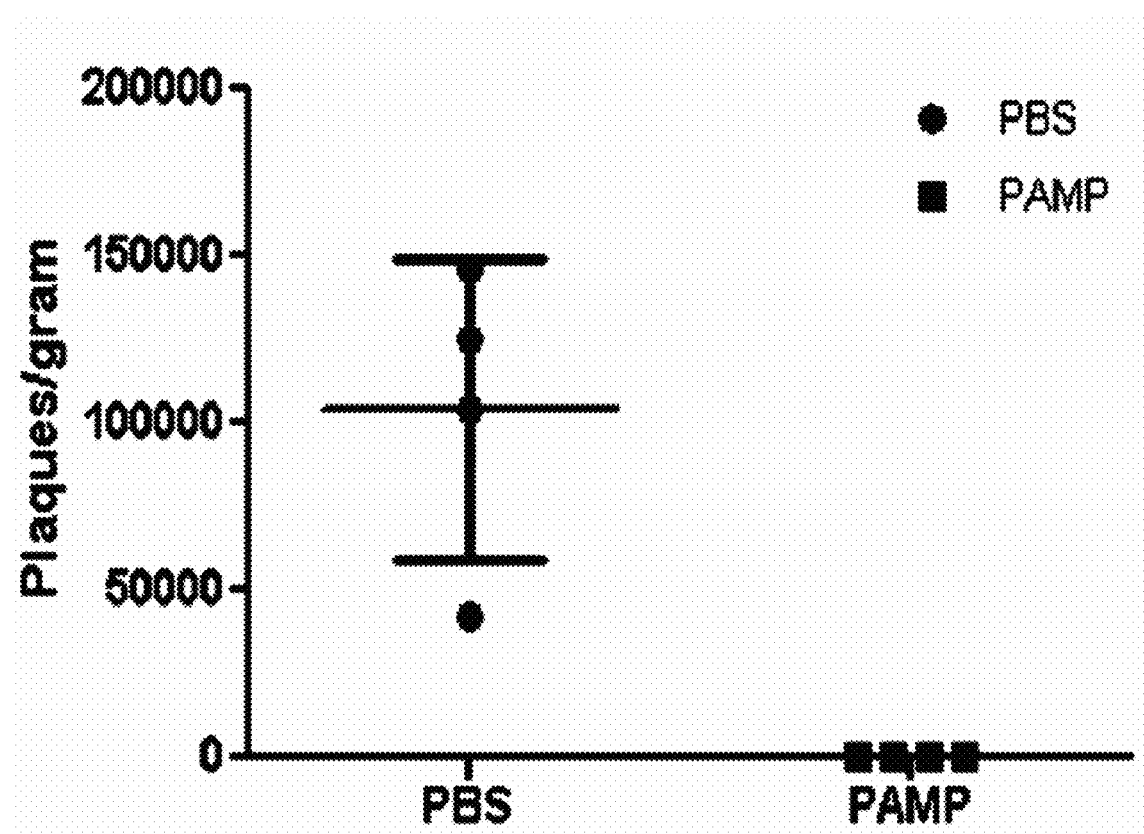

FIGS. 13A-13D illustrate that polyU/UC RNA treatment protects mice after West Nile virus (WNV) infection in a MAVS/RLR signaling-dependent manner. Wildtype and MAVS-/-mice were infected via subcutaneous injection of the left footpad with 1000 pfu WNV (Tx-02). At days 1.5, 3, and 5, mice were given 200 mg polyU/UC RNA or PBS control by hydrodynamic IV injection in the tail vein. Mice were monitored daily for body weight and clinical scores. Mice that lose greater than or equal to 20% body weight or that exhibit clinical symptoms greater than 5 were euthanized according to UW IACUC protocols. FIG. 13A shows the percent survival/morbidity curve, FIG. 13B shows the average body weight, and FIG. 13C shows the average clinical score for mice over a course of 17 days post-infection. FIG. 13D shows results of a standard plaque assay in a parallel study where the spleens were collected from wildtype mice at d8 post-infection and analyzed for viral burden. These data demonstrate that poly-U/UC RNA is a potent antiviral therapy.

Figure 14A:
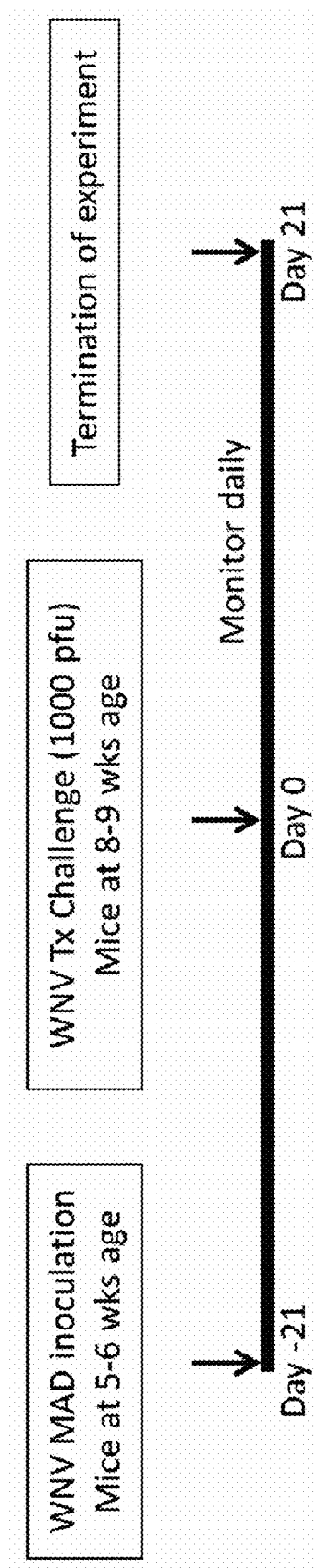
Figure 14B:
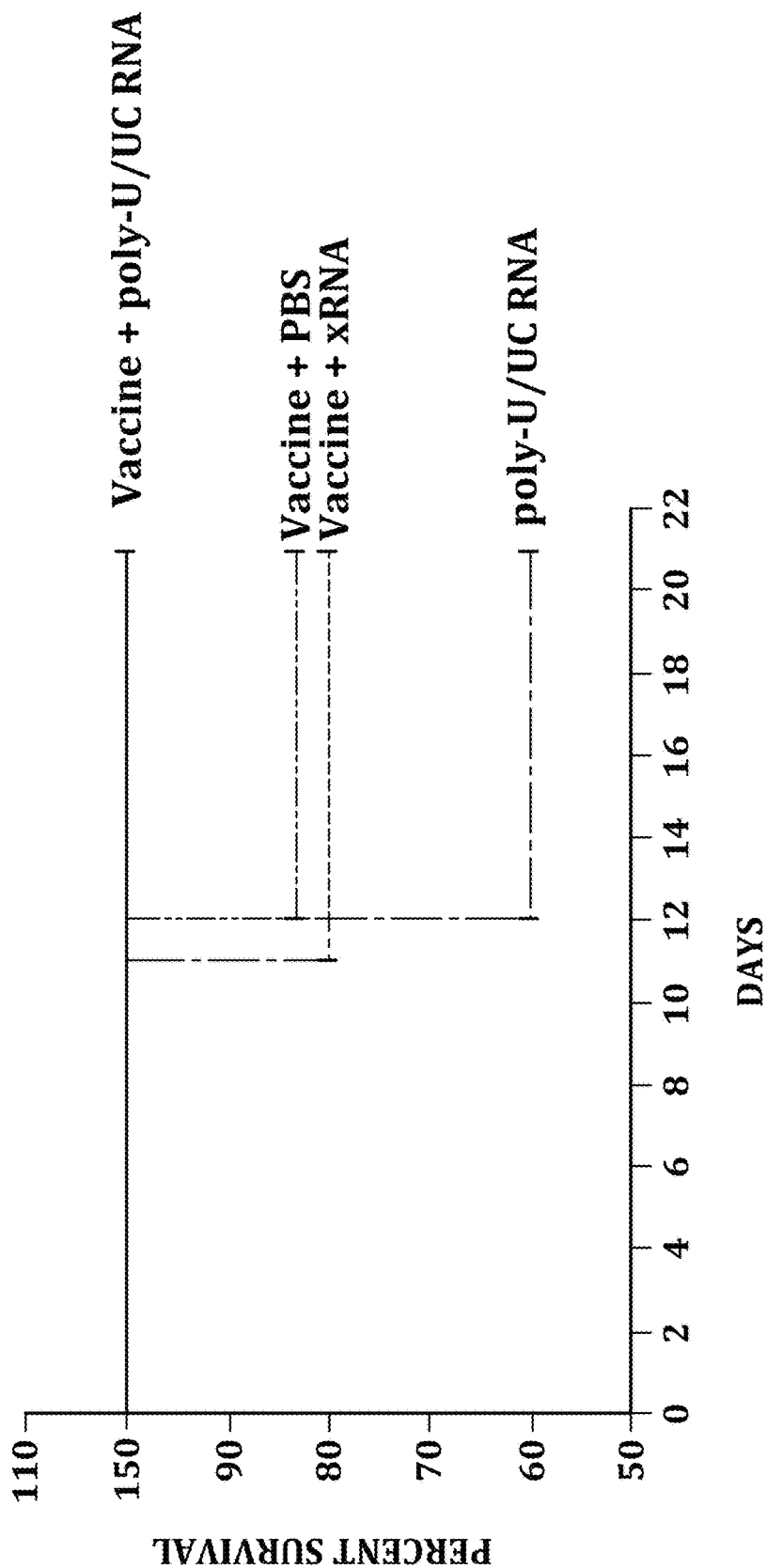

FIGS. 14A-14B illustrate the experimental approach (FIG. 14A) and the resulting survival data (FIG. 14B) demonstrating that polyU/UC RNA enhances vaccine-mediated protection of mice from West Nile virus (WNV) challenge. C57Bl6 mice were vaccinated with 100 mg polyU/UC RNA alone, 0.25 mg UV-inactivated WNV +PBS, or 0.25 mg UV-inactivated WNV mixed with 100 mg polyU/UC RNA or xRNA control. Mice were challenged 3 weeks later with 1000 pfu WNV (Tx-02) administered via subcutaneous injection of the left footpad. Mice were monitored daily for body weight and clinical scores. Mice that lose greater than or equal to 20% body weight or that exhibit clinical symptoms greater than 5 were euthanized according to UW IACUC protocols. The graph in FIG. 14B shows percent survival/morbidity curve for mice over a course of 21 days post-infection (starting at Day 0, as indicated in FIG. 14A). Differences shown between vaccine +poly-U/UC and other lines are significant (P<0.03). This demonstrates that poly-U/UC RNA is an effective vaccine adjuvant for enhancement of protection by RNA virus vaccines.

DETAILED DESCRIPTION

Viral infection of vertebrate host cells triggers the innate immune response through non-self recognition of pathogen associated molecular patterns (PAMPs), such as PAMPs in viral nucleic acid. Accurate PAMP discrimination is essential to avoid self-recognition that can generate autoimmunity, and therefore should be defined by the presence of multiple motifs in a PAMP that mark it as non-self. Furthermore, the degree of innate immune response should be properly controlled to avoid costly damage to healthy host tissue in an excessive immune response.

Hepatitis C virus (HCV) RNA is recognized as non-self by RIG-I through the presence of a 5'-triphosphate (5'-ppp) on the viral RNA in association with an untranslated 3' poly-U/UC tract. As described in more detail below in Example 1, the inventors defined the specific HCV PAMP and the criteria for RIG-I non-self discrimination of HCV by examining the RNA structure-function attributes that impart PAMP function to the poly-U/UC tract. It was determined that a poly-uracil (U) "core" of this sequence tract was essential for RIG-I activation, and that interspersed ribocytosine nucleotides between poly-U sequences in the general RNA 3' region helped to achieve optimal RIG-I signal induction. 5'-ppp-poly-U/UC RNA variants that stimulated strong RIG-I activation efficiently bound purified RIG-I protein in vitro, and RNA interaction with both the repressor domain and helicase domain of RIG-I was required to activate signaling. When appended to 5'-ppp RNA that lacks PAMP activity, the poly-U/UC U-core sequence conferred non-self recognition of the RNA and innate immune signaling by RIG-I. Importantly, HCV poly-U/UC RNA variants that strongly activated RIG-I signaling triggered potent anti-HCV responses in vitro and hepatic innate immune responses in vivo using a mouse model of PAMP signaling. These data indicate a multi-motif PAMP signature of non-self recognition by RIG-I that incorporates a 5'-ppp with varying poly-uracil sequence composition and length. This HCV PAMP motif drives potent RIG-I signaling to induce the innate immune response to infection. These studies define a basis of non-self discrimination by RIG-I and offer insights into the antiviral therapeutic potential of targeted RIG-I signaling activation.

Importantly, it was also found that the strength of RIG-I interaction and subsequent signaling varied with the length of the poly-uracil core. Accordingly, by the incorporation of poly-uracil cores of variable lengths, and the appropriate interspersing of non-uracil residues in the remainder of the general 3'-polyU/UC region, a PAMP can be rationally designed to elicit an innate immune response of appropriate intensity to provide an effective response while avoiding undue damage to host tissue, such as septic shock.

In Example 2, the inventors further demonstrate the utility of the HCV-derived poly-U/UC PAMP RNA constructs to elicit effective cellular responses to infection by a variety of virus types. As described in more detail in Example 2, it was determined that administration of poly-U/UC PAMP RNA constructs with U-core sequences over 8 nucleotides can lead to innate response signaling and reduction of viral load in vitro for a variety of viruses infections. In Example 3, the inventors established that poly-U/UC PAMP RNA constructs induced innate immune response signaling in vivo and led to reduced viral burden and increased survival. In Example 4, the inventors established that co-administration of poly-U/UC PAMP RNA constructs with an attenuated/killed West Nile virus (WNV) vaccine significantly enhanced the protective capacity of the vaccine against infection by infective WNV.

In accordance with the above discovery, in one aspect, the present disclosure provides a synthetic nucleic acid pathogen-associated molecular pattern (PAMP).

As used herein, the term "nucleic acid" refers to a polymer of monomer units or "residues". The monomer subunits, or residues, of the nucleic acids each contain a nitrogenous base (i.e., nucleobase) a five-carbon sugar, and a phosphate group. The identity of each residue is typically indicated herein with reference to the identity of the nucleobase (or nitrogenous base) structure of each residue. Canonical nucleobases include adenine (A), guanine (G), thymine (T), uracil (U) (in RNA instead of thymine (T) residues) and cytosine (C). However, the nucleic acids of the present disclosure can include any modified nucleobase, nucleobase analogs, and/or non-canonical nucleobase, as are well-known in the art. Modifications to the nucleic acid monomers, or residues, encompass any chemical change in the structure of the nucleic acid monomer, or residue, that results in a noncanonical subunit structure. Such chemical changes can result from, for example, epigenetic modifications (such as to genomic DNA or RNA), or damage resulting from radiation, chemical, or other means. Illustrative and nonlimiting examples of noncanonical subunits, which can result from a modification, include uracil (for DNA), 5-methylcytosine, 5-hydroxymethylcytosine, 5-formethylcytosine, 5-carboxycytosineb-glucosyl-5-hydroxy-methylcytosine, 8-oxoguanine, 2-amino-adenosine, 2-amino-deoxyadenosine, 2-thiothymidine, pyrrolo-pyrimidine, 2-thiocytidine, or an abasic lesion. An abasic lesion is a location along the deoxyribose backbone but lacking a base. Known analogs of natural nucleotides hybridize to nucleic acids in a manner similar to naturally occurring nucleotides, such as peptide nucleic acids (PNAs) and phosphorothioate DNA.

The five-carbon sugar to which the nucleobases are attached can vary depending on the type of nucleic acid. For example, the sugar is deoxyribose in DNA and is ribose in RNA. In some instances herein, the nucleic acid residues can also be referred with respect to the nucleoside structure, such as adenosine, guanosine, 5-methyluridine, uridine, and cytidine. Moreover, alternative nomenclature for the nucleoside also includes indicating a "ribo" or deoxyrobo" prefix before the nucleobase to infer the type of five-carbon sugar. For example, "ribocytosine" as occasionally used herein is equivalent to a cytidine residue because it indicates the presence of a ribose sugar in the RNA molecule at that residue. The nucleic acid polymer can be or comprise a deoxyribonucleotide (DNA) polymer, a ribonucleotide (RNA) polymer, including mRNA. The nucleic acids can also be or comprise a PNA polymer, or a combination of any of the polymer types described herein (e.g., contain residues with different sugars).

In some embodiments, the synthetic nucleic acid PAMP is an RNA construct. In some of these embodiments, the synthetic nucleic acid PAMP is derived from, or reflects the sequence of, the HCV poly-U/UC region and, thus, may be generally referred to as the poly-U/UC PAMP RNA construct.

As used herein, the term "synthetic," with reference to the synthetic nucleic acid PAMP, refers to non-natural character of the nucleic acid. Such nucleic acids can be synthesized de novo using standard synthesis techniques. Alternatively, the nucleic acid PAMPs can be generated or derived from naturally occurring pathogen sequences using recombinant technologies, which are well-known in the art. In some embodiments, the sequence of the synthetic nucleic acid PAMP construct is not naturally occurring. Descriptions of illustrative approaches to generate synthetic nucleic acid PAMPs are provided in more detail below.

The synthetic nucleic acid PAMP of this aspect comprises (a) a 5'-arm region comprising a terminal triphosphate; (b) a poly-uracil core (also referred to as a poly-U core); and (c) a 3'-arm region. In one embodiment, the three regions (a, b, and c) are covalently linked in a single nucleic acid polymer macromolecule. The covalent linkage can be direct (without interspersed linker sequence(s)) or indirect (with interspersed linker sequences(s)). In one embodiment, the 5'-arm region is covalently linked to the 5'-end of the poly-U core. In one embodiment the 3'-arm region is covalently linked to the 3'-arm region of the poly-U core. The polymer can be single or double stranded, or can appear with a combination of single and double stranded portions.

As described in more detail below, it is demonstrated for the first time herein that HCV-derived RNA PAMPs with poly-uracil core sequences have the capacity to trigger RIG-I signaling and, thus, can stimulate an innate immune response capable of reducing viral load, yet is appropriate to avoid septic shock. Accordingly, in one embodiment, the poly-U core comprises at least 8 contiguous uracil residues. In further embodiments, the comprises between 8 and 30 contiguous uracil residues, such as 8, 9, 10, 11, 12, 13, 14, 15, 16, 17, 18, 19, 20, 21, 22, 23, 24, 25, 26, 27, 28, 29, or 30 contiguous uracil residues. In one embodiment, the poly-U core comprises more than 8 contiguous uracil residues. In one embodiment, the poly-U core comprises 12 or more contiguous uracil residues. In some embodiments, the poly-U core consists of a plurality of contiguous uracil residues, such as 8, 9, 10, 11, 12, 13, 14, 15, 16, 17, 18, 19, 20, 21, 22, 23, 24, 25, 26, 27, 28, 29, or 30 contiguous uracil residues.

In one embodiment, the 3'-arm region comprises a 5'-most nucleic acid residue that is not a uracil residue. Instead, the 5'-most nucleic acid residue of the 3'-arm region can be an adenine, guanine, or cytosine residue, or any non-canonical residue. In one embodiment, the 5'-most nucleic acid residue of the 3'-arm region is a cytosine residue or a guanine residue.

In one embodiment, the nucleotide composition of the 3'-arm region is at least 40% uracil residues. In some embodiments, the 3'-arm region is at least 45%, is at least 50%, is at least 60%, is at least 70%, is at least 80%, or is at least 90% uracil residues. In one embodiment, the 3'-arm region comprises a plurality of short stretches (for example, between about 2 and about 15 nucleotides in length) of contiguous uracil residues with one or more cytosine residues interspersed therebetween. In one embodiment, the 3'-arm region comprises a stretch of consecutive uracil residues that does not exceed the length of the poly-U core of the synthetic PAMP construct. In one embodiment, the 3'-arm region does not comprises a stretch of consecutive uracil residues that exceeds the length of the poly-U core of the synthetic PAMP construct. In some embodiments, the 3'-arm region comprises at least 7 consecutive uracil residues, such as 7, 8, 9, 10, 11, 12, 13, 14, 15, 16, 17, 18, 19, 20, 21, 22, 23, 24, 25, 26, 27, 28, or 29, contiguous uracil residues.

At a minimum, the 5'-arm region consists of a terminal tri-phosphate (ppp) moiety. In such embodiment, the triphosphate is at the 5'-terminus of the synthetic nucleic acid PAMP and can be represented as "5'-ppp". In a further embodiment, the terminal triphosphate is linked directly to the 5'-end of the poly-U core sequence. In an alternative embodiment, the 5'-arm region comprises the 5'-end terminal triphosphate and one or more additional nucleic acid residues, the sequence of which terminates with a 3'-end. The one or more additional nucleic acid residues in the 5'-arm region of this embodiment are disposed between the terminal triphosphate and the 5'-most uracil residue of the poly-U core. Persons of ordinary skill in the art will readily appreciate that the one or more additional nucleic acid residues in the 5'-arm region can be any number of nucleic acid residues and can present any sequence without limitation. As is described in more detail below, the sequence of the one or more additional nucleic acid residues in the 5'-arm region does not affect the functionality of the synthetic PAMP. For instance, it is described that the addition of a poly-U core region to a non-stimulatory nucleic acid that contains a 5'-triphosphate (such as the HCV X region) confers stimulatory properties for innate immune system signaling. In one embodiment, the sequence of the one or more additional nucleic acid residues in the 5'-arm region does not consist of the entire 5'-end portion of a naturally occurring HCV genome sequence that naturally occurs "upstream" or 5' to the poly-U core of the poly-U/UC region for that HCV strain. Stated differently, in this embodiment the entire synthetic nucleic acid PAMP construct is not a naturally occurring HCV genome, complete with the 5' triphosphate, the entire coding region, and the untranslated 3' poly-U/UC region. Accordingly, in this embodiment, the 5'-arm region, the one or more nucleic acid residues of the 5'-arm region, and the poly-uracil core do not naturally occur together in an HCV genome. However, in this embodiment, the one or more nucleic acid residues of the 5'-arm region can comprise or consist of a subfragment of the entire naturally occurring sequence that exists between the 5'-arm region and the poly-uracil core. Alternatively, in this embodiment, the one or more nucleic acid residues of the 5'-arm region can comprise sequence in addition to a portion or the entire naturally occurring HCV genome sequence that exists between the 5'-end and the poly-uracil core.

The synthetic PAMP of claim 1, wherein the synthetic PAMP is capable of inducing retinoic acid-inducible gene I (RIG-I)-like receptor (RLR) activation. In one embodiment, the RLR is RIG-I. Persons of ordinary skill in the art would readily be able to determine the activation of an RLR, such as by assaying the transcription of known downstream RLR-regulated genes, as described in more detail below. For example, in some embodiments, RLR activation can be established by an increase in IFN-β or ISG54 expression. In another embodiment, RLR activation can be established by an increase in IRF-3 phosphorylation.

In some embodiments, the synthetic nucleic acid PAMP further comprises and additional nucleic acid domain that encodes a functional gene product, such as a polypeptide or interfering RNA construct. The additional nucleic acid domain can be part of the 3'-arm domain, as the whole or part of the one or more additional nucleic acid residues therein. In another embodiment, the additional nucleic acid domain can be disposed between any of the 5'-arm region comprising a terminal triphosphate, the poly-uracil core, and the 3'-arm region. In some embodiments, the nucleic acid domain further comprises promoter regions, known in the art, to facilitate the general or inducible expression of the functional gene product in a host cell. Such gene products can be selected based on specific functionality, such as gene products that can further assist in the treatment or prevention of pathogen infections.

In another aspect, the present disclosure provides a pharmaceutical composition comprising the synthetic nucleic acid PAMP of claim 1.

In some embodiments, the pharmaceutical composition further comprises an attenuated, inactivated, or killed virus, bacterium, protozoan, fungus, and/or helminth. The inclusions of such attenuated, inactivated, or killed virus, bacterium, protozoan, fungus, and/or helminth provides additional antigens that that can be recognized by components of the adaptive immune system. For example, the additional antigen may stimulate antibody production, or when presented on MHC, may stimulate a T-cell receptor to trigger antigen-specific responses of B and T cells, respectively. With the stimulation of the adaptive immune system, and specific memory cells that are specific to the antigen, a more long term protection against the pathogen can be generated in addition to conferring immediate protection.

In other embodiments, the pharmaceutical composition further comprises an antigen derived from a pathogen, such as a viral antigen, a bacterial antigen, a protozoal antigen, a fungal antigen, and/or a helminth antigen, and the like.

In some embodiments, the pharmaceutical composition comprises any additional known therapeutic composition, such as anti-viral compositions, anti-biotic therapeutic, anti-fungal therapeutic, anti-protozoal therapeutic, and anti-helminth therapeutic, as are known in the art. Co-administration of such therapeutic(s) with the synthetic nucleic acid PAMP constructs in a pharmaceutical composition can provide the advantage of triggering a multi-approach to responding to the presence of a pathogen.

In any of the above embodiments, the virus can be any known pathogenic virus of interest. For example, the virus can be a member of, or is derived from, the Flaviviridae, Paramyxoviridae, Hepaciviridae, Orthomyxoviridae, Bunyaviridae, Arenaviridae, Reoviridae, Retroviridae, Enteroviruses, Picornaviridae, Coronaviridae, or Noroviridae families, or the viral antigen is derived from a virus of the Flaviviridae, Paramyxoviridae, Hepaciviridae, Orthomyxoviridae, Bunyaviridae, Arenaviridae, Reoviridae, Retroviridae, Enteroviruses, Picornaviridae, Coronaviridae, or Noroviridae families. Specific examples include West Nile virus, dengue virus, Japanese encephalitis virus, vesicular stomatitis virus, hepatitis C virus, respiratory syncytial virus, yellow fever virus, influenza A virus, Lassa fever virus, Hantavirus, lymphocytic choriomenengitis virus, polio virus, parainfluenza virus, rotavirus, human immunodeficiency virus (HIV), human T-lymphotropic virus (HTLV), enterovirus 21 and strains thereof, severe acute respiratory syndrome (SARS) virus, Middle East respiratory syndrome (MERS) virus, corona virus, or norovirus. In some embodiments, the attenuated, inactivated, or killed virus, is derived from any of the above classifications, for example, by multiple passages through cell culture or modification through any molecular technique known in the art, such as recombinant technologies.

As will be appreciated by persons of skill in the art, the pharmaceutical composition can comprise additional components to enhance functionality or stability of the pharmaceutical composition for use in any relevant and appropriate application. For example, the pharmaceutical composition can further comprise one or more of the following: an adjuvant (e.g., a vaccine delivery system and/or immunostimulatory compound), stabilizer, buffer, surfactant, controlled release component, salt, and/or a preservative, depending on the intended formulation for administration, as would be readily determined by persons of skill in the art.

The pharmaceutical composition described herein can include an adjuvant. As used herein, the term "adjuvant" can be broadly separated into two classes, based on the principal mechanisms of action: carrier/delivery systems and immunostimulatory compounds.

A variety of carrier or therapeutic delivery systems are known and can be applied to the pharmaceutical composition. Delivery systems can include particle formulations, such as emulsions, microparticles, immune-stimulating complexes (ISCOMs), nanoparticles, which can be, for example, particles and/or matrices, and liposomes, and the like, which are advantageous for the delivery of antigens.

In addition, or alternatively, an adjuvant is provided to generate a signal to the immune system so that it facilitates a response to the antigen, wherein the antigen drives the specificity of the response to the pathogen. Such "immunostimulatory" compound adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system. However, it is noted that the optional adjuvant referred to herein refers to a component that is in addition to, and distinct from, the novel synthetic nucleic acid PAMP that is provided in this disclosure. Organic adjuvants can also include toxins produced by pathogens, such as cholera toxin.

Additionally, preferred inorganic adjuvants include aluminum salts (alum) such as aluminum phosphate, amorphous aluminum hydroxyphosphate sulfate, and aluminum hydroxide, which are commonly used in human vaccines and are easily adapted to new vaccine technologies.

Typically, the same adjuvant or mixture of adjuvants is present in each dose of the pharmaceutical composition. Optionally, however, an adjuvant can be administered with the first dose of the pharmaceutical composition and not with subsequent doses (i.e., booster shots). Alternatively, a strong adjuvant can be administered with the first dose of the pharmaceutical composition and a weaker adjuvant or lower dose of the strong adjuvant can be administered with subsequent doses. The adjuvant can also be selected according to the relative efficacy of the adjuvant in consideration of the selected strength of the synthetic nucleic acid PAMP, which can vary depending on the length of the poly-U core.

In addition to the additional antigens and the adjuvants described above, the pharmaceutical composition formulation can include one or more additional components, such as a stabilizer, buffer, surfactant, controlled release component, salt, and/or preservative, as are well-known in the art.

In another aspect, the present disclosure provides a method of inducing RLR signaling in a cell. The method comprises contacting the cell with an effective amount of the synthetic nucleic acid PAMP described herein. In some embodiments, the RLR is RIG-I. The method can be performed in vitro, ex vivo, or in vivo. In some embodiments, the method is repeated one or more times. In some embodiments, the induction of RLR signaling is detectable by an increase in IFN-β levels, an increase in ISG54 levels, an increase in IRF3 phosphorylation, or an increase in the expression of any other interferon stimulated gene regulated by RLRs such as RIG-I.

In another aspect, the present disclosure provides a method of treating a condition in a subject treatable by inducing RLR signaling. Such conditions include any infection by a pathogen that is treatable by induction or enhancement of an innate immune response. Such pathogens are well-known, and include viruses, bacteria, protozoa, fungi, and helminth parasites.

As used herein, the term "treating" with reference to any condition, disease or infection includes preventing (e.g., a prophylactic use) the condition, disease or infection. In this context, the term treating refers to preventing or suppressing the infection of colonization of a pathogen. Additionally, the term "treating" refers to a therapeutic use, such as addressing an infection that has already started. In one embodiment, the term "treating" refers to curing the infection to a point where no active pathogens remain in the host. In another embodiment, the term "treating" also encompasses slowing or inhibiting the spread of the infection within the body, such as slowing or inhibiting the replication rate of the pathogen. The term also encompasses reducing the pathogenic burden in a cell (or host tissue or body). The term also encompasses accelerating the rate of clearance of the pathogen relative to the time period required by the host's endogenous immune response to clear the pathogen without administration of the synthetic nucleic acid PAMP. Finally, the term "treating" also encompasses ameliorating the symptoms caused by pathogenic infection.

In yet another aspect, the present disclosure also provides a method of inducing an innate immune response in a subject. The method comprises administering to the subject an effective amount of the pharmaceutical composition as described herein. As described, the pharmaceutical composition can be formulated for any appropriate route of administration. The method comprises administering an effective amount of the pharmaceutical composition to the subject in need thereof. The pathogenic burden can be monitored by any known technique for detection and quantification of the pathogen. As described above, the pharmaceutical composition can comprise additional components that address the disease or condition, such as pathogenic antigens to further stimulate the innate and/or adaptive immune responses, additional therapeutic agents, and the like.

In yet another aspect, the present disclosure also provides a method of treating a viral, bacterial, protozoal, fungal, and/or helminth infection in a subject. The method comprises administering to the subject an effective dose of the pharmaceutical composition described herein. As with other aspects of the disclosure, the pharmaceutical composition can comprise other therapeutic components, such as pathogen agents, attenuated, killed, or inactivated pathogens, therapeutic agents, such as antibiotics and the like), additional adjuvants, and the like.

In preferred embodiments of any of the methods described herein, the administration or application of pharmaceutical composition comprising the synthetic nucleic acid PAMP does not induce septic shock to the subject.

In any of the above methods, the pharmaceutical compositions can be appropriately formulated for preferred routes of administration according to known methods. The pharmaceutical composition can be formulated for delivery by any route of systemic administration (e.g., intramuscular, intradermal, subcutaneous, subdermal, transdermal, intravenous, intraperitoneal, intracranial, intranasal, mucosal, anal, vaginal, oral, or buccal route, or they can be inhaled). Certain routes of administration are particularly appropriate for pharmaceutical compositions intended to induce, at least, an innate immune response. In particular, transdermal administration, intramuscular, subcutaneous, and intravenous administrations are particularly appropriate.

The formulations suitable for introduction of the pharmaceutical compositions vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

As will be readily appreciated, the amount of nucleic acid PAMP in the administered formulation will vary depending upon the design of the nucleic acid PAMP (e.g., the "strength" as determined by the length of the poly-U core), as well as the inclusion and identity of any additional adjuvants or antigens.

The above methods can also comprise one or more administrations to the subject (or to the culture of cells). The doses of pharmaceutical composition can be the same or different for each dose in the administration regime, as can be readily determined by skilled persons in the art.

In any of the above methods, the administration or application of synthetic nucleic acid PAMP can be in conjunction or in association with the administration of a vaccine to stimulate a response against a pathogen. As described, in some instances, the pharmaceutical composition containing the synthetic nucleic acid PAMP can further comprise a pathogen antigen or even the entire killed, inactivated, or attenuated pathogen to stimulate an immune response and/or generate immunological memory against the pathogen. In another embodiment, the synthetic nucleic acid PAMP can be administered separately, but in coordination with a vaccine to achieve the same effects. The inducement of the innate immune response by the synthetic nucleic acid PAMP can provide enhanced protection against the pathogen as compared to the protection provided by the vaccine alone.

Without being bound by any particular theory, the added protection likely results from the direct anti-pathogenic effects of the innate immune response, in addition to the enhanced stimulation of the adaptive immune response mechanisms through cross-signaling provided by the stimulated cells of the innate immune system. An example of this effect is described in more detail in Example 4.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

The use of the term "about" is intended to include a slight variation, such as 10%, above and below the stated value.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

General texts which describe molecular biological techniques useful herein, including the use of vectors, promoters and many other relevant topics, include Berger and Kimmel, Guide to Molecular Cloning Techniques, Methods in Enzymology Volume 152, 1987 (Academic Press, Inc., San Diego, Calif.) ("Berger"); Sambrook et al., Molecular Cloning: A Laboratory Manual, 2d ed., Vol. 1-3, Cold Spring Harbor Laboratory, Cold Spring Harbor, N.Y., 1989 ("Sambrook"); and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). These and any other publications cited herein and the subject matter for which they are cited are hereby specifically incorporated by reference in their entireties.

EXAMPLES

Example 1

Summary

Pathogen recognition receptors (PRRs) are critical components of the innate immune response to viral pathogens, and function in the host to recognize pathogen-associated molecular patterns (PAMPs) in pathogen proteins or nucleic acids. Retinoic acid-inducible gene I (RIG-I) is a cytoplasmic PRR that senses viral RNA inside an infected cell. For example, RIG-I recognizes hepatitis C virus (HCV) RNA as non-self through the presence of both a 5'-triphosphate (5'-ppp) and a 3' poly-U/UC tract within the viral RNA. This Example describes the examination of the RNA structure-function attributes that define the HCV poly-U/UC tract as non-self to RIG-I, including nucleotide composition. It was found that a 34 nucleotide poly-uridine "core" (U-core) within the HCV poly-U/UC tract RNA stimulated non-self recognition by RIG-I, and interspersed ribocytosine nucleotides were also important to induce optimal RIG-I signaling. Furthermore, constructs with poly-uridine cores as short as 8 nucleotides stimulated RIG-I signaling. RIG-I/RNA binding studies revealed that RIG-I formed weaker interactions with HCV RNAs lacking poly-U sequences, and RNA interaction with multiple domains of RIG-I was required to activate signaling. Finally, RIG-I recognition of the U-core within the poly-U/UC tract activated anti-HCV responses in vitro and hepatic innate immune responses in vivo. These studies identify long poly-uridine sequences with interspersed ribocytosines as an HCV PAMP motif that drives optimal RIG-I signaling. The results of these studies were also published in Schnell, G., et al., "Uridine Composition of the Polu-U/UC Tract of HCV RNA Defines Non-Self Recognition by RIG-I," *PLOS Pathogens* 8(8):e1002839 (2012), incorporated herein by reference in its entirety.

Introduction

Mammalian cells respond to pathogens, such as in acute virus infections, through the actions of host pathogen recognition receptors (PRRs) that recognize viral pathogen-associated molecular patterns (PAMPs). The RIG-I-like receptors (RLRs) are cytoplasmic RNA helicases that function as PRRs for the recognition of RNA virus infection. The RLRs include RIG-I (retinoic acid-inducible gene I), MDA5 (melanoma differentiation-associated gene 5), and LGP2 (laboratory of genetics and physiology 2). Whereas RIG-I and MDA5 encode tandem amino-terminal caspase activation and recruitment domains (CARDs), LGP2 lacks CARDs and is thought to play a regulatory role in signaling initiated by RIG-I or MDA5. Following the recognition and binding of viral PAMP RNA, RIG-I signals through the adaptor protein mitochondrial antiviral signaling (MAVS, also known as IPS-1/VISA/Cardif). Downstream signaling by the RLRs induces the activation of latent transcription factors, including interferon regulatory factor (IRF)-3 and NF-κB, leading to the production of type-I interferons (IFN) from the infected cell. Local IFN secretion leads to the expression of hundreds of interferon-stimulated genes (ISGs) in the infected cell and surrounding tissue that mediate antiviral and immunomodulatory properties in order to restrict virus replication and impart the onset of the immune response to infection.

The process of RIG-I signaling activation has been revealed through structure-function studies. In addition to the N-terminal CARDs, RIG-I possesses a central DExD/H box RNA helicase/ATPase domain and a C-terminal repressor domain (RD). RIG-I recognizes and binds to specific PAMP motifs within RNA marked by a free/exposed 5'-triphosphate (5'-ppp), including single-stranded (ss)RNA or double-stranded (ds)RNA. RIG-I binding interactions with viral RNA are mediated through multiple contacts with the helicase domain and the C-terminal RD, the latter of which binds 5'-ppp motifs with high specificity. RIG-I recognition and binding of viral RNA relieves auto-repression and drives ATP hydrolysis and conformational rearrangements that expose the CARDs for downstream signaling to initiate the immune response to infection. Despite the recent advancements in RIG-I structural biology, the nature of RIG-I recognition of sequence-specific PAMP RNA motifs remains unclear. Accurate discrimination of self from non-self by PRRs is essential to avoid immune triggering against self that leads to autoimmunity. In this sense, PRR recognition of a single PAMP motif alone, such as 5'-ppp, within viral RNA is unlikely to accurately discriminate the comparably low abundance PAMP RNA from the high abundance host RNA. Moreover, the presence of a single motif within host RNA that displays the PAMP signature could induce aberrant signaling against self, whereas a combinatorial non-self signature for PRR binding and signaling activation would serve to accurately discriminate it as a PAMP. Previous studies have revealed that multiple parameters define an RNA PAMP for RIG-I recognition, including 5'-ppp, length (>19 nt), secondary structure characteristics, and nucleotide sequence motifs.

RIG-I is essential for host cell recognition of a variety of RNA viruses, including hepatitis C virus (HCV). HCV is a positive-sense ssRNA virus that replicates in hepatocytes and causes chronic liver disease and liver cancer. Approximately 200 million people worldwide are persistently infected with HCV, and infection is characterized by chronic viral replication, producing viral RNA that can trigger innate immune responses. HCV RNA is recognized as non-self by RIG-I through recognition of the poly-U/UC tract located in the 3' non-translated region (NTR) of the viral genomic RNA, thus defining the poly-U/UC tract as a PAMP motif of HCV. The HCV poly-U/UC tract is approximately 100 nucleotides (nt) in length and is essential for virus replication and viability. While the poly-U/UC tract is conserved in 39 NTR placement within all genotypes and strains of HCV, it varies in the length of poly-uridine sequences and the positioning of ribocytosine nucleotides. RIG-I recognition of the HCV poly-U/UC tract is dependent on the 5'-ppp RNA length and sequence composition, and RIG-I signaling is attenuated in response to HCV poly-U/UC RNAs shorter than 50 nucleotides in length or with a reduced poly-uridine nucleotide composition compared to wild-type viral RNA. Although RIG-I recognizes HCV RNA, the specific RNA sequence motifs in the HCV poly-U/UC tract that confer RIG-I recognition are not known.

In this study, the properties of RIG-I recognition of HCV RNA were evaluated by conducting a detailed structure-function analysis of RIG-I and poly-U/UC RNA interactions and innate immune signaling. The results show that the poly-uridine core (U-core) within the HCV poly-U/UC tract was essential for recognition by RIG-I, indicating that RIG-I recognizes long poly-uridine regions as non-self motifs within 5'-ppp RNA. In addition, the affinity of RIG-I/RNA binding interactions, and critical contacts between the PAMP RNA and RIG-I helicase domain, both defined an HCV RNA recognition sequence in which long poly-uridine sequences (>U17) with interspersed ribocytosines induced in vitro anti-HCV responses and hepatic innate immune responses in vivo. Furthermore, it was demonstrated that HCV RNA sequences in which shorter poly-uridine sequences with at least 8U core sequences stimulated some IFN-β signaling. Thus, RIG-I recognition of the U-core within the poly-U/UC tract of the 5'-ppp HCV RNA is the trigger of innate antiviral immunity to HCV infection. Poly-uridine sequences could thereby offer a novel application for innate immune stimulation in vaccine vectors and antimicrobial therapeutic strategies for controlling infections.

Results

The U-core of the HCV poly-U/UC tract is required for RIG-I signal induction.

Figure 1A:
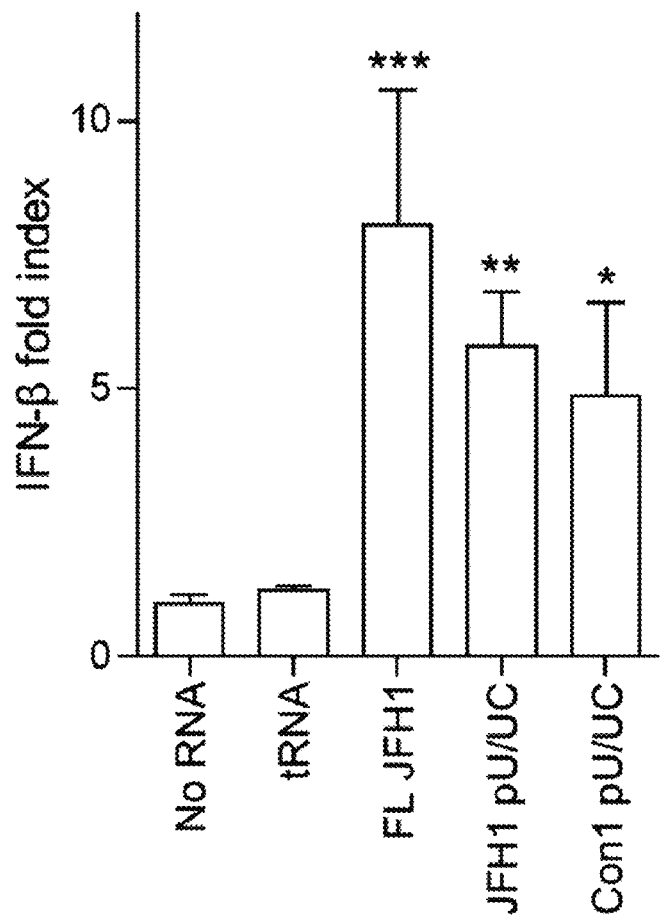
FIGS. 1A-1C illustrate that HCV-derived poly-U/UC RNA constructs activate RIG-I signaling.

To determine the RNA sequence elements in the HCV poly-U/UC tract required for non-self recognition by RIG-I, multiple poly-U/UC RNA constructs were developed that encoded changes in distinct regions termed the 5'arm, U-core, and 3'arm, and based on the HCV genotype 1b consensus (Con1) poly-U/UC sequence (Table 1). Two RNA constructs encoding either the HCV Con1 3' NTR X-region sequence alone, or including a 34 nt poly-uridine sequence between stem-loops 1 (SLI) and 2 (SLIT) of the X-region were also developed. Each RNA was generated in vitro from a DNA template using the T7 RNA polymerase, which resulted in the RNA products having a 5'-ppp and three guanine nt at the 5' end. Previous studies demonstrated that the poly-U/UC tract, but not the X-region, of the HCV 3' NTR was responsible for RIG-I recognition and triggering of innate immune signaling. The ability of equal moles of 5'-ppp full-length JFH1 HCV RNA or the JFH1 poly-U/UC tract to activate RIG-I signaling to the IFN-β-promoter in human hepatoma (Huh7) cells harboring an intact RIG-I pathway were assessed. The full-length HCV RNA genome and the poly-U/UC tract RNA from either genotype 1b (Con1) or 2a (JFH1) were able to activate signaling and drive transcription from the IFN-β-promoter (FIG. 1A), confirming that the poly-U/UC tract of the HCV RNA is a PAMP that triggers PRR signaling. Additionally, induction of the IFN-β-promoter by the Con1 and JFH1 poly-U/UC tract (pU/UC) RNAs in Huh7 cells (FIG. 1B) was also found to be linked with the induction of IRF-3 phosphorylation and ISG expression (FIG. 1C). Additionally, Huh7.5 cells that lack a functional RIG-I pathway failed to respond to transfected HCV RNA constructs (FIG. 1B), thus defining RIG-I-dependence to HCV PAMP recognition and innate immune signaling.

TABLE 1

HCV poly-U/UC RNA constructs developed for RIG-I binding and activation studies.

| RNA construct[a] | 5' arm[b] | U-core | 3' arm | SEQ ID NO: |
|---|---|---|---|---|
| Con1 pU/UC | 5'GGCCAUCCUGUUUUUUCCC(U11)C | U34 | CUCCUUUUUUUUCCUCUUUUUUUCCUUUUCUUUCCUUU | 1 |
| JFH1 pU/UC | 5'ACUGUUCC | U43 | C(U14)CCCUCUUUCUUCCCUUCUCAUCUUAUUCUACUU UCUUUCUU | 2 |

TABLE 1-continued

HCV poly-U/UC RNA constructs developed for RIG-I binding and activation studies.

| RNA construct[a] | 5' arm[b] | U-core | 3' arm | SEQ ID NO: |
|---|---|---|---|---|
| pU/UC C26 | 5'GGCCAUCCUGUUUUUUCCC(U11)C | U34 | CUCCUUUUUUUUCCUCUUUUUUUCCUUUUCUUUCCUUU (C26) | 3 |
| pU/UC 3'C26 | 5'GGCCAUCCUGUUUUUUCCC(U11)C | U34 | CUCCUUUUUUUUCCCCCCCCCCCCCCCCCCCCCCCCCCC | 4 |
| pU/UC C67U | 5'GGCCAUCCUGUUUUUUCCC(U11)C | U34 | UUCCUUUUUUUUCCUCUUUUUUUCCUUUUCUUUCCUUU | 5 |
| poly-U 107 | 5'UUUUUUUUUUUUUUUUUUU(U11)U | U34 | UUUUUUUUUUUUUUUUUUUUUUUUUUUUUUUUUUUUUUU | 6 |
| Δcore | 5'GGCCAUCCUGUUUUUUCCC(U11)C | --- | CUCCUUUUUUUUCCUCUUUUUUUCCUUUUCUUUCCUUU | 7 |
| U8core | 5'GGCCAUCCUGUUUUUUCCC(U11)C | U8 | CUCCUUUUUUUUCCUCUUUUUUUCCUUUUCUUUCCUUU (C26) | 8 |
| U17core r | 5'GGCCAUCCUGUUUUUUCCC(U11)C | U17 | CUCCUUUUUUUUCCUCUUUUUUUCCUUUUCUUUCCUUU (C17) | 9 |
| pU/UC 62 | 5'GGCAUCCUG-------------- | U34 | CUCCUUUUUUUUCCUCU-------------------- | 10 |
| 5'C | 5'CCCCCCCCCC------------- | U34 | CUCCUUUUUUUUCCUCU-------------------- | 11 |
| 3'C | 5'GGCCAUCCUG-------------- | U34 | CCCCCCCCCCCCCCCCC-------------------- | 12 |
| poly-U 62 | 5'UUUUUUUUUU-------------- | U34 | UUUUUUUUUUUUUUUUU-------------------- | 13 |
| poly-U 62-C | 5'UUUUUUUUUU-------------- | U34 | CUUUUUUUUUUUUUUUU-------------------- | 14 |
| U/C1 | 5'UUCCUUCCUU-------------- | U34 | CUCCUUUUUUUUCCUCU-------------------- | 15 |
| U/C2 | 5'UUUUUUUUUG-------------- | U34 | CUCCUUUUUUUUCCUCU-------------------- | 16 |
| U/C3 | 5'UUUUUUUUUG-------------- | U34 | CUUUUUUUUUUUUCCUUU------------------- | 17 |
| U/C4 | 5'GGUUUUCCUU-------------- | U34 | CUUUUUUUUUUUUUUUU-------------------- | 18 |
| U/C5 | 5'GGCCAUCCUG-------------- | U10 | C(U10)C(U10)CUCUCCUUUUUUUUCCUCU------- | 19 |
| U/C6 | 5'GGCCAUCCUG-------------- | U15 | C(U15)CUUCUCCUUUUUUUUCCUCU------------ | 20 |
| U/C7 | 5'GGCCAUCCUG-------------- | U10 | CCC(U10)CCC(U8)CUCCUUUUUUUUCCUCU------ | 21 |
| U/C8 | 5'GGCCAUCCUG-------------- | U18 | CCCCCC(U10)CUCCUUUUUUUUCCUCU---------- | 22 |

[a]The X-region RNA construct has the sequence 5'-GGUGGCUCCAUCUUAGCCCUAGUCACGGCUAGCUGUGAAAGGUCCGUGAGCCGC-UUGACUGCAGAGAGUGCUGAUACUGGCCUCUCUGCAGAUCAAGU-3' (SEQ ID NO: 23). The X-region-U34 RNA construct has the sequence 5'-GGGUGGCUCCAUCUUAGCCCUAGUCACGGCUAGCUGUGAAAGGUCCGUGAGC(U34)CGCUUGACUGCAGAGAGUGCUGAUACUGGCCU-CUCU-GCAGAUCAAGU-3' (SEQ ID NO: 24).
[b]All RNAs include a 5'-ppp and three guanine nucleotides at the 5' end of the RNA. Dashes indicate nucleotide deletions, and underlined nucleotides show changes from the HCV Con1 poly-U/UC sequence. Long homo-polymeric nucleotide sequences are indicated in parentheses with the nucleotide designation followed by the number of nucleotides in the sequence.

Figure 1B:
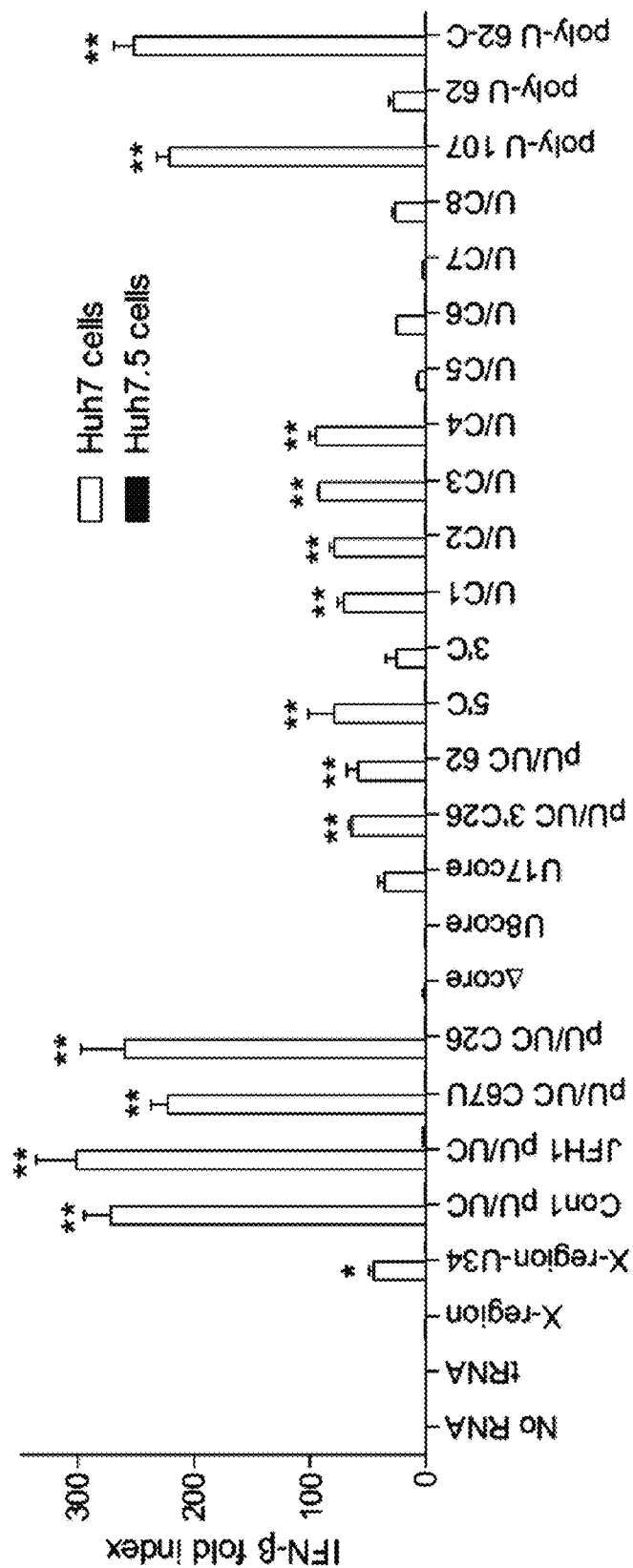
Figure 1C:
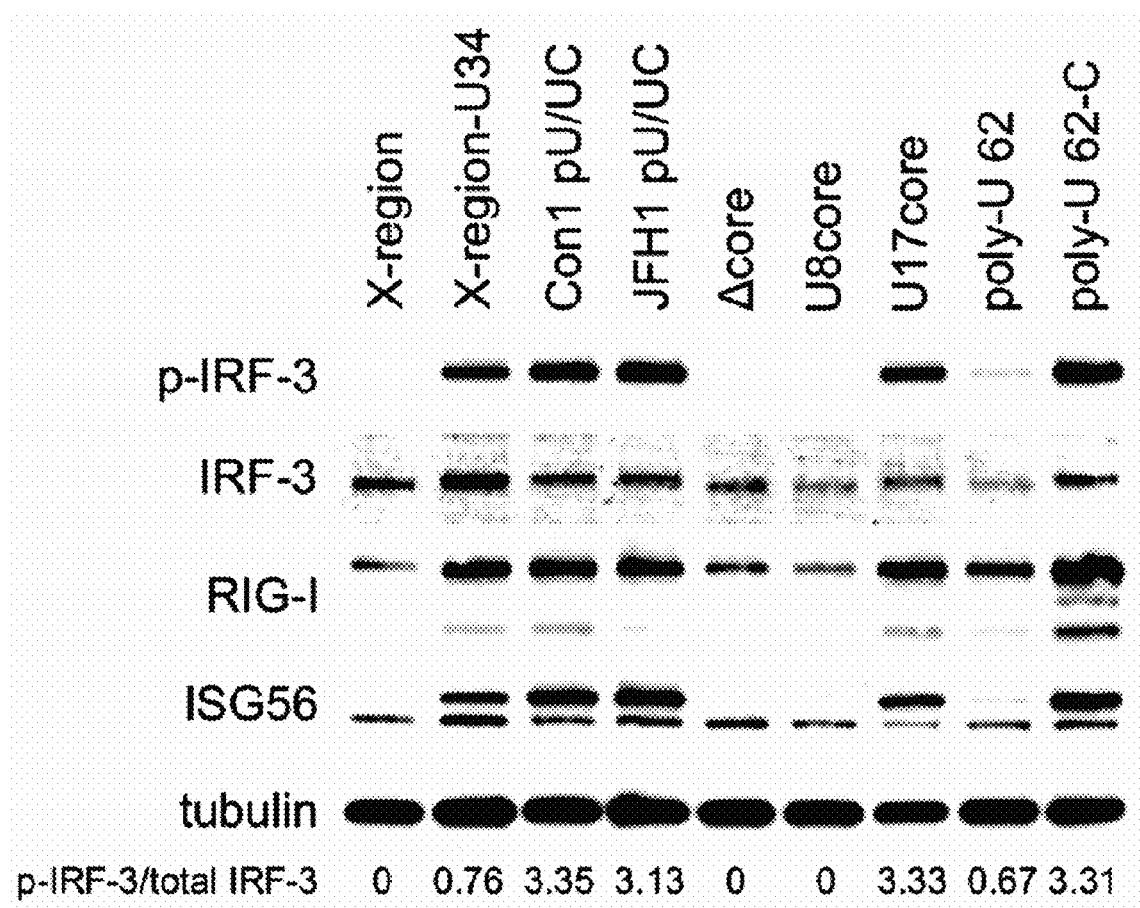

Huh7 and Huh7.5 cell responses to HCV poly-U/UC tract RNA construct derivatives were further evaluated (Table 1 and FIG. 1). Neither the C67U nt substitution (pU/UC C67U construct) nor the addition of 26 ribocytosine nucleotides to the 3'end of the RNA (pU/UC C26) significantly changed signaling compared to wild-type poly-U/UC RNA in Huh7 cells. However, despite the presence of a 5'-ppp, deletion of the U-core from the pU/UC tract (Δcore) ablated the induction of IRF-3 phosphorylation and signaling to the IFN-β-promoter, thus preventing ISG expression (FIG. 1B and FIG. 1C). While replacement of the U-core with 8 uridine nts (U8core) did not result in detectable IRF-3 phophorylation, a 17 uridine nt core RNA (U17core) triggered low levels of IFN-β signaling activity and IRF-3 phosphorylation. These data indicate that in addition to a 5'-ppp, a U-core length of over 8 uridine nucleotides may be sufficient to stimulate some RIG-I based signaling. In addition, while the 5'-ppp HCV X-region RNA did not trigger RIG-I signaling, it was found that insertion of a 34 nt poly-U sequence (U34) into the X-region RNA between SLI and SLII (X-region-U34) resulted in its recognition as a PAMP to stimulate IRF-3 phosphorylation, IFN-β-promoter activity, and ISG expression (FIG. 1B and FIG. 1C). Other RNA constructs with sequence changes in the U-core region (U/C5, U/C7) exhibited a significantly decreased capacity to stimulate induction of the IFN-β-promoter ($P<0.01$ and $P<0.001$ respectively, two-tailed Student's t-test) compared to either the wild-type Con1 pU/UC RNA or the truncated pU/UC 62 RNA (encoding the wild-type U-core). Taken together, these results demonstrate that the U-core of the HCV poly-U/UC tract exceeding 8 uridine residues is required for non-self recognition by RIG-I and subsequent activation of the innate immune response.

Analysis of specific poly-U/UC tract constructs also revealed that interspersed ribocytosine nucleotides between the poly-U sequences in the RNA were necessary to achieve optimal RIG-I signal induction. It was noted that substitution of the last 26 nucleotides in the 3'arm of the poly-U/UC tract to ribocytosines (pU/UC 3'C26) resulted in a significant decrease in IFN-β-promoter induction compared to the wild-type Con1 pU/UC sequence (FIG. 1B; P=0.0047, two-tailed Student's t-test). Thus, although the U-core is required for poly-U/UC recognition by RIG-I, the uridine/ribocytosine sequences located in the 3'arm play a role in PAMP recognition. Therefore, a set of truncated poly-U/UC constructs was developed with C to U substitutions and their PAMP activity was compared. Activity was defined as signaling of IFN-β-promoter induction, with PAMP activity driven by the equivalent-length pU/UC 62 construct. The 5'C, 3'C, U/C1, U/C2, U/C3, and U/C4 RNA constructs each exhibited similar PAMP activity as the pU/UC 62 RNA to induce the IFN-β-promoter (FIG. 1B). Removal of all ribocytosine nucleotides revealed a property of length-dependent, U-specific PAMP activity of which the shorter poly-U 62 RNA induced significantly less signaling to the IFN-β-promoter compared to the longer poly-U 107 RNA in Huh? cells (FIG. 1B; P=0.0004, two-tailed Student's t-test). However, this effect of RNA length was overcome by inserting a single ribocytosine nucleotide into the poly-U 62 RNA, wherein the poly-U 62-C RNA was able to drive IRF-3 phosphorylation, IFN-β-promoter induction, and ISG expression as efficiently as the wild-type Con1 pU/UC RNA (FIG. 1B and FIG. 1C). Thus, poly-U length and ribocytosine content impact RIG-I recognition and PAMP activity of the HCV poly-U/UC tract.

RNA binding interactions determine RIG-I signaling activation.

Figure 2A:
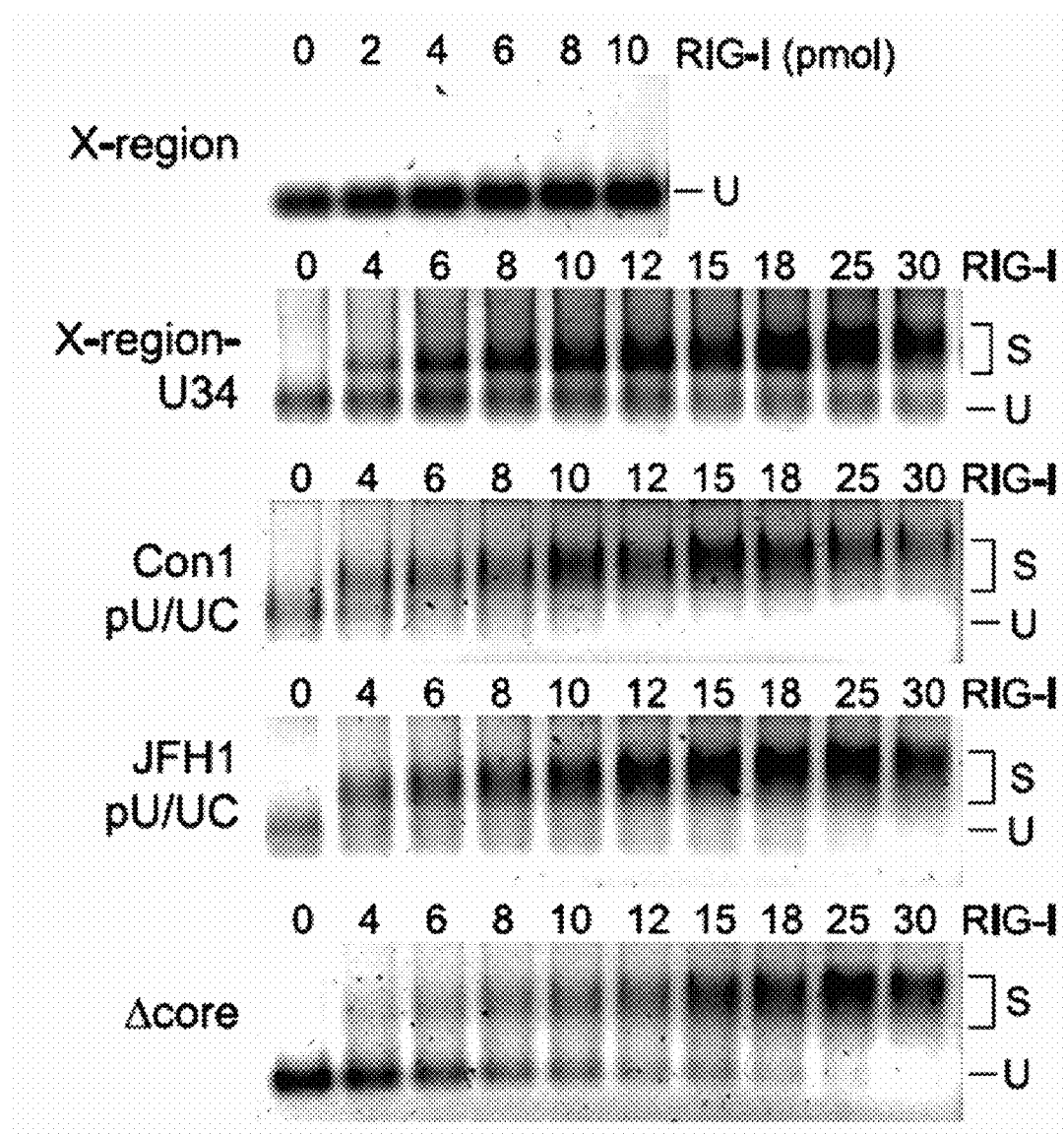
Figure 2A:
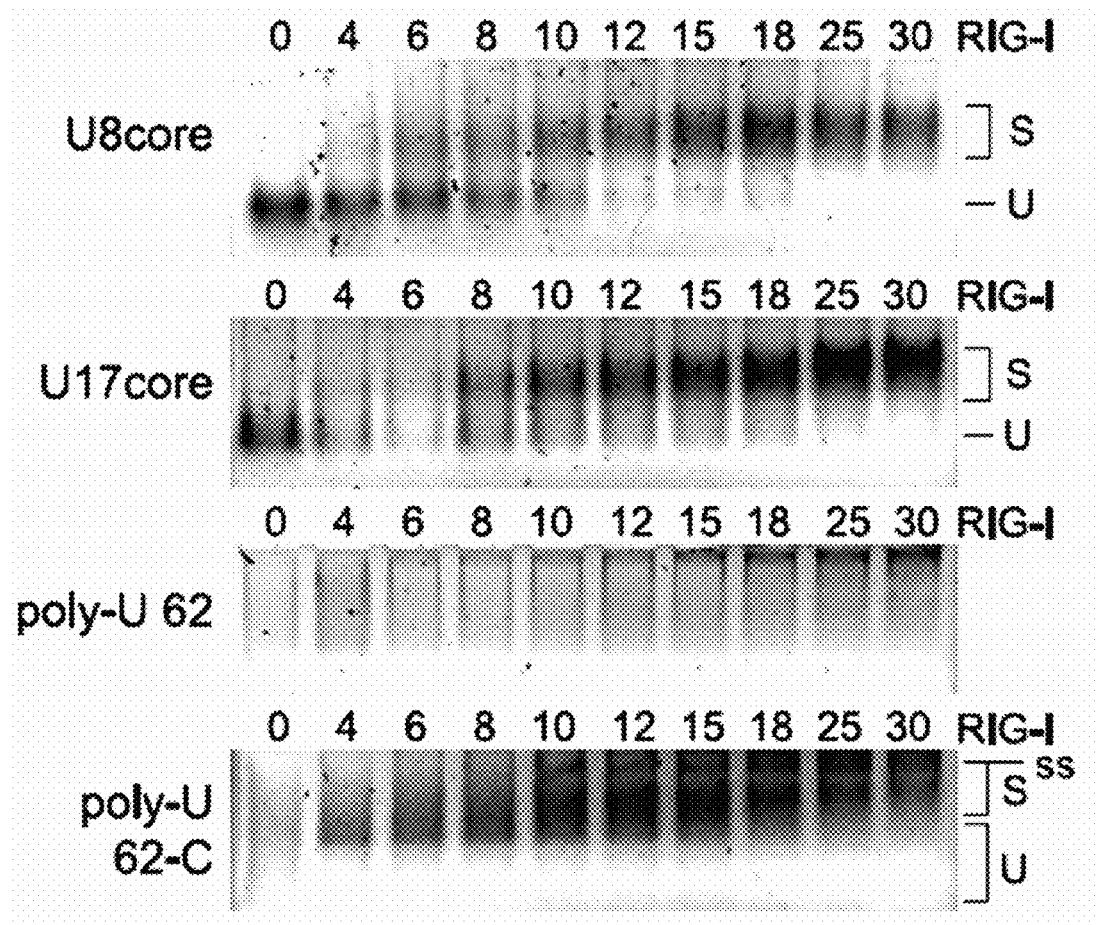
Figure 2A:
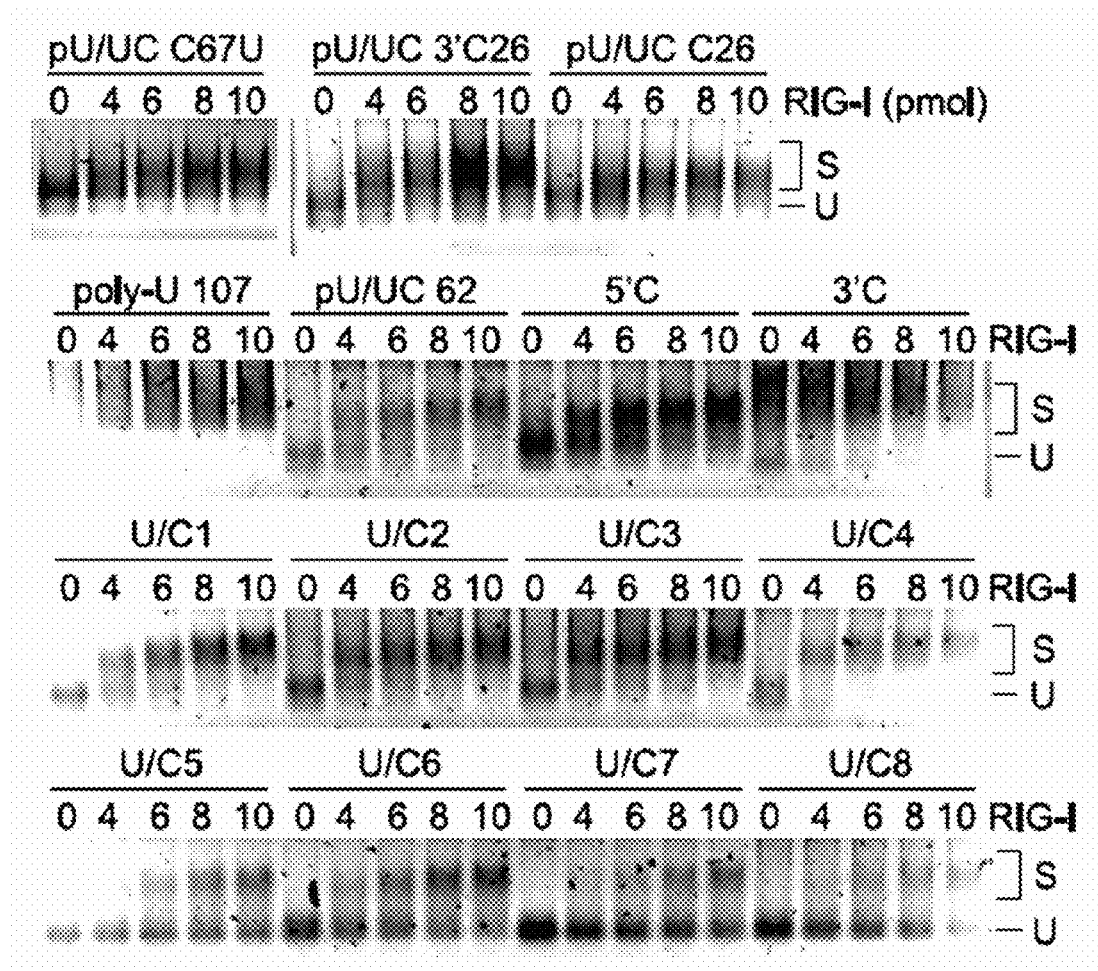
Figure 2B:
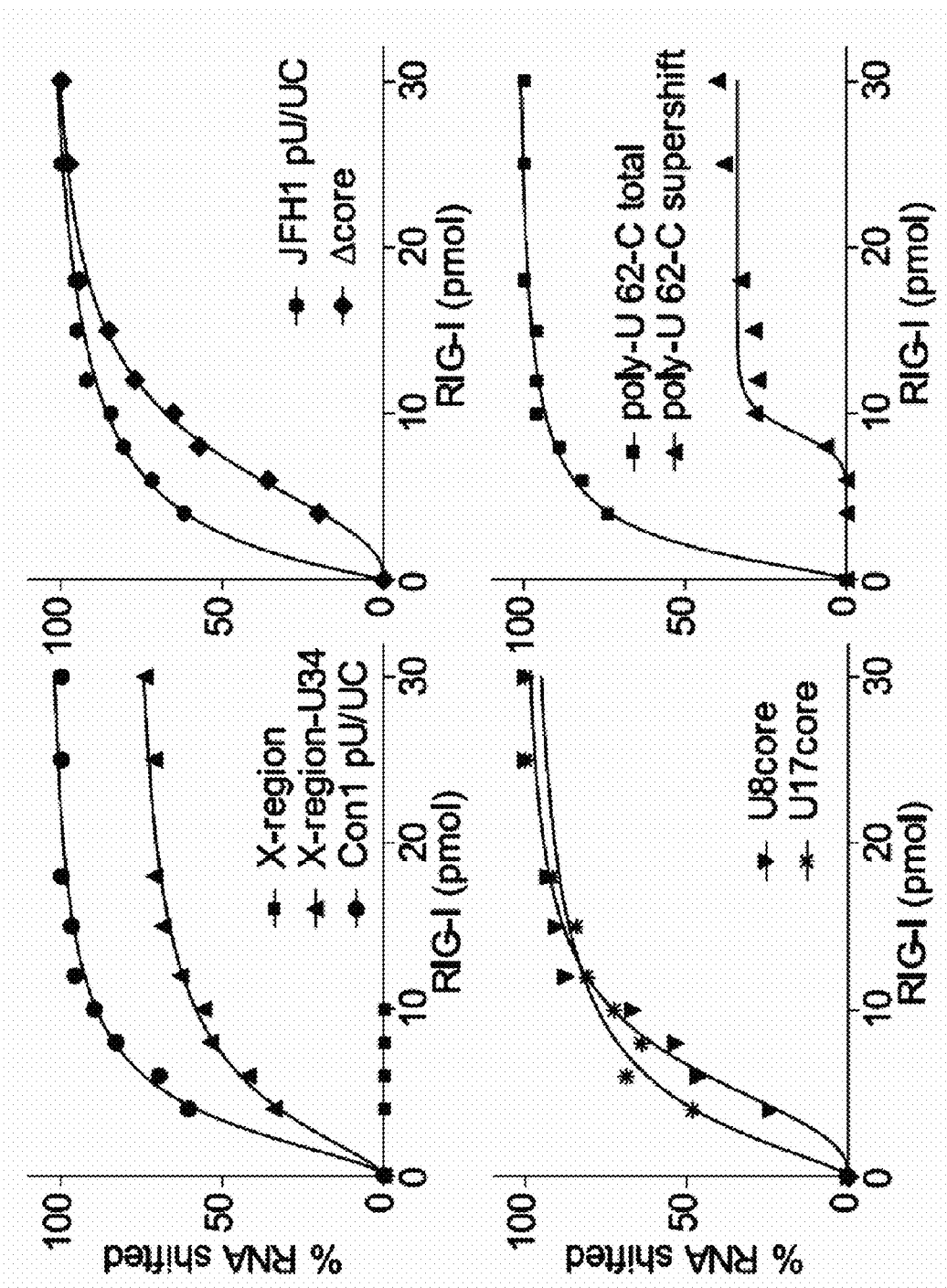

To examine the binding interactions between HCV poly-U/UC RNA and RIG-I that impart PAMP activity, an electrophoretic mobility gel-shift assay (EMSA) was conducted with purified recombinant RIG-I protein and 10 pmol of each poly-U/UC RNA construct (FIG. 2A). Comprehensive EMSA analyses were conducted on nine RNA constructs to generate saturation-binding curves (FIG. 2B). The largest differences in RIG-I binding between the various poly-U/UC RNA constructs were detected at lower RIG-I concentrations (0-10 pmol), whereas increasing saturation of RIG-I/RNA binding reactions were observed for most RNA constructs at concentrations of RIG-I that exceeded 10 pmol. In order to compare the association differences between the RNA constructs and RIG-I, the pmol effective concentration (EC) of RIG-I required to shift 10% ($EC_{10}$), 50% ($EC_{50}$), or 90% ($EC_{90}$) of each RNA as determined by EMSA was calculated (FIG. 2C). The EC values for the X-region, X-region-U34, Con1 pU/UC, JFH1 pU/UC, Δcore, U8core, U17core, and poly-U 62-C RNAs were calculated using the graphical equation generated from the comprehensive EMSA analyses (graphically depicted in FIG. 2B). The remaining RNA constructs had more limited EMSA analyses; therefore, only the general ranges for the EC values to between 0-10 pmol RIG-I were able to be calculated.

As shown in FIG. 2C, the $EC_{10}$ values for the various poly-U/UC RNA constructs ranged from 0.65-3.04 pmol RIG-I, and $EC_{50}$ values ranged from 2.28-7.31 pmol RIG-I. Noting that all RNAs included a 5'-ppp, it was found that the X-region RNA did not bind to RIG-I in the range of 0-10 pmol of protein, while the X-region-U34 RNA had an $EC_{10}$ value of 1.42 pmol RIG-I and >50% of the RNA bound to 8 pmol of RIG-I, demonstrating that the inserted U34 sequence promoted stable binding interactions between RIG-I and the X-region-U34 RNA. In addition, it was found that $EC_{10}$ values were significantly larger (P=0.0005, two-tailed Student's t-test) for RNAs that did not signal (Δcore) versus RNAs that demonstrated PAMP activity and signaled to the IFN-β-promoter (X-region-U34, Con1 pU/UC, JFH1 pU/UC, U17core, and poly-U 62-C). The non-signaling Δcore RNA contain large deletions in the U-core region, while the RNAs that induced RIG-I signaling all contained poly-U sequences >8 nt in length. These data reveal that RIG-I forms only weak interactions with 5'-ppp RNAs lacking poly-U sequences, and demonstrate that the poly-U core of the HCV pU/UC tract over 8 nucleotides long is likely required to confer stable RIG-I/RNA binding interactions. There was not a significant difference in the $EC_{50}$ or $EC_{90}$ values between the signaling and non-signaling RNAs, indicating that differences in RNA affinity may play an important role in determining RIG-I signaling activation at lower, more physiologically relevant concentrations of RIG-I.

RIG-I/RNA affinity among RNAs denoted as non-signaling/low signaling (Δcore, U8core), medium signaling (X-region-U34, U17core), and high signaling (Con1 pU/UC, JFH1 pU/UC, poly-U 62-C) were also examined based on their ability to induce different levels of signaling to the IFN-β promoter. There was a statistically significant increase in the $EC_{10}$ (P=0.0025, two-tailed Student's t-test) and $EC_{50}$ (P=0.004) values measured for no/low signaling RNAs compared to high signaling RNAs, thus demonstrating that the Δcore and U8core RNAs (lacking a poly-U core) form significantly weaker interactions with RIG-I than those RNAs with stronger PAMP activity. A significant difference was also detected when comparing the $EC_{10}$ values measured for no/low signaling compared to medium signaling RNAs (P=0.0263). In general, the $EC_{90}$ for all RNA constructs was >10 pmol RIG-I regardless of whether or not the RNA could drive RIG-I activation. However, there was still a significant difference in the $EC_{90}$ values between RNAs that did not signal (Δcore, U8core) and the RNAs that induced high signaling to the IFN-β-promoter (Con1 pU/UC, JFH1 pU/UC, poly-U 62-C; P=0.0208 using a two-tailed Student's t-test). Thus, these data link HCV RNA sequences containing poly-U motifs with stronger RIG-I binding and enhanced signaling for an overall potent PAMP activity. Taken together, the data indicate that the strength of RIG-I/RNA binding interactions defines an HCV RNA recognition sequence in which poly-uridine sequences greater than 8 uridine nucleotides with interspersed ribocytosines drive RIG-I binding and signaling to induce the innate immune response.

RNA interactions with the RIG-I RD and helicase domain are important for PAMP signaling.

RIG-I is maintained in an auto-repressed conformation in uninfected cells where the CARDs interact with either the C-terminal repressor domain (RD), the helicase insertion domain (Hel2i), or both domains. Crystal structure studies of RIG-I bound to RNA have revealed that the RD interacts with the 5'-ppp terminus of the RNA, which brings RNA structures in close contact with the helicase domains to allow for more specific RIG-I/RNA interactions. To further assess RNA interactions with RIG-I, and to determine how HCV PAMP RNA interacts with the helicase domain and RD of RIG-I, limited-trypsin proteolysis of RIG-I/RNA complexes were conducted for nine RNA constructs selected to represent a range of PAMP activity (FIG. 3). RIG-I is highly sensitive to trypsin proteolysis in the absence of PAMP RNA; however, upon binding to an RNA ligand RIG-I undergoes conformational changes that protect the RD and other RNA-bound domains from trypsin digestion.

Figure 3A:
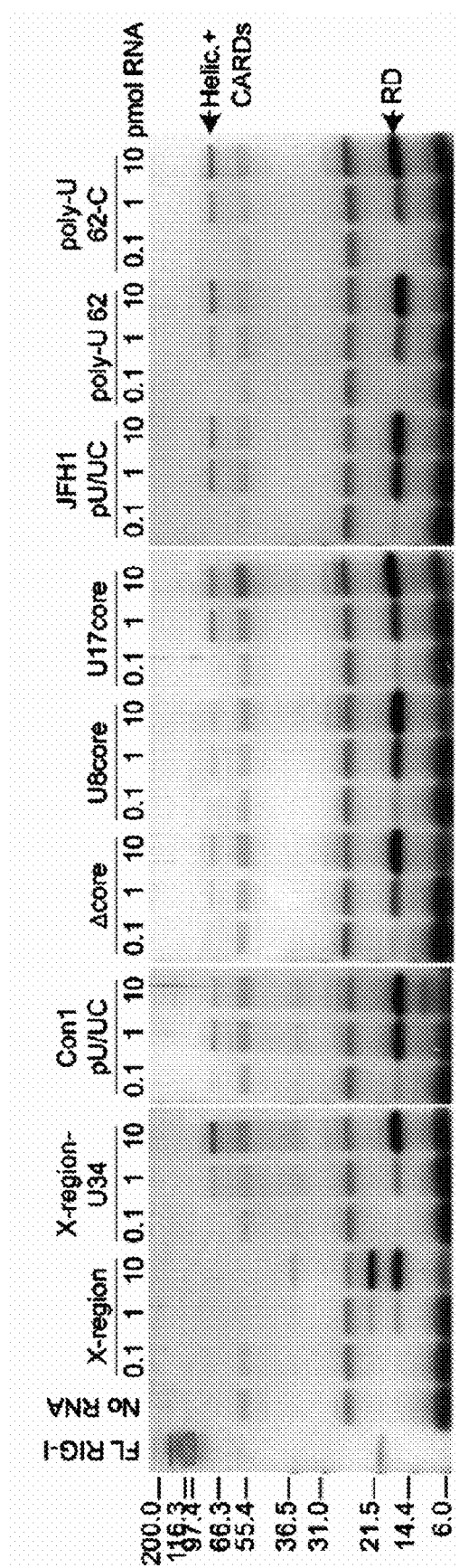
FIGS. 3A-3C illustrate that HCV poly-U/UC RNA constructs interact with the RIG-I RD and helicase domain.
Figure 3B:
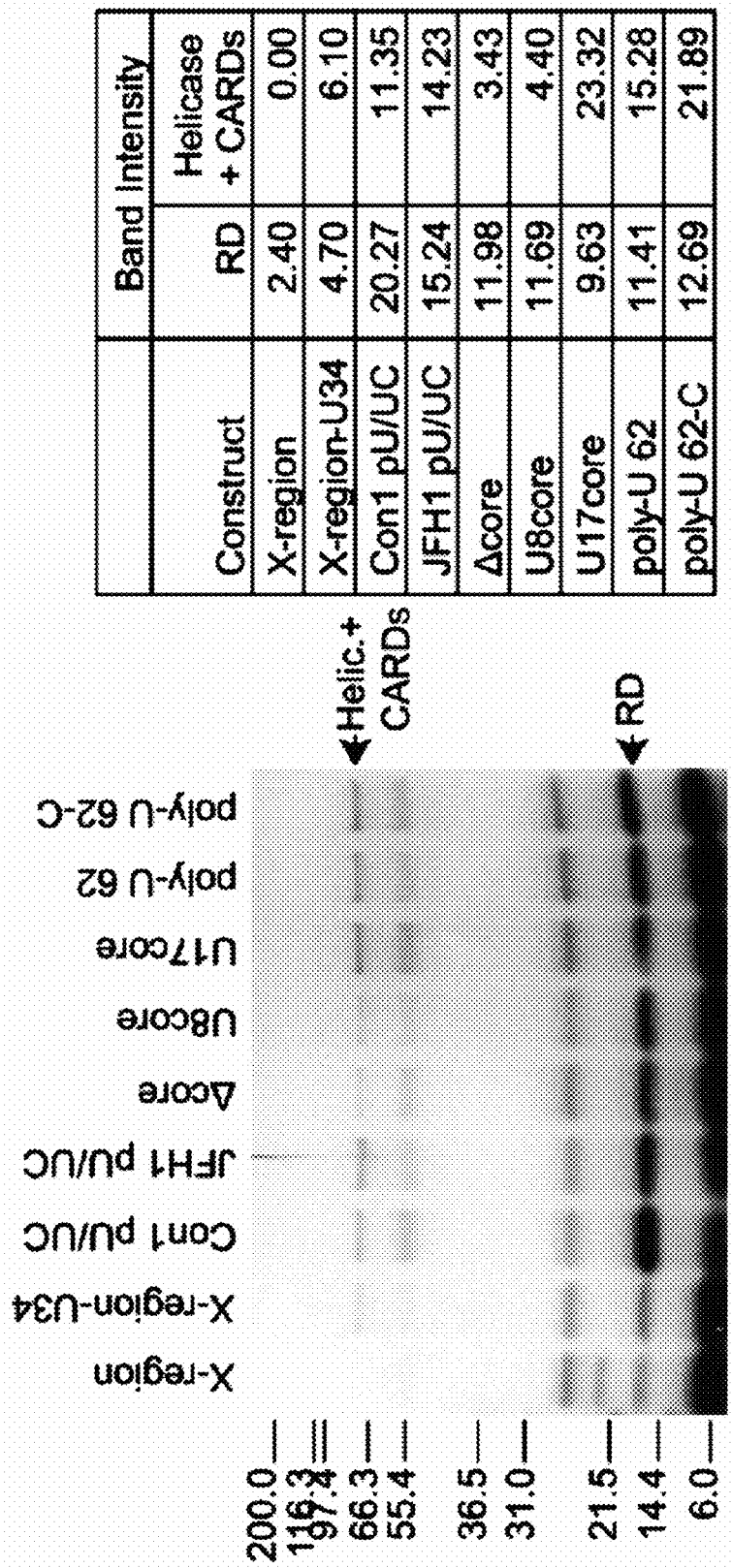
Figure 3C:
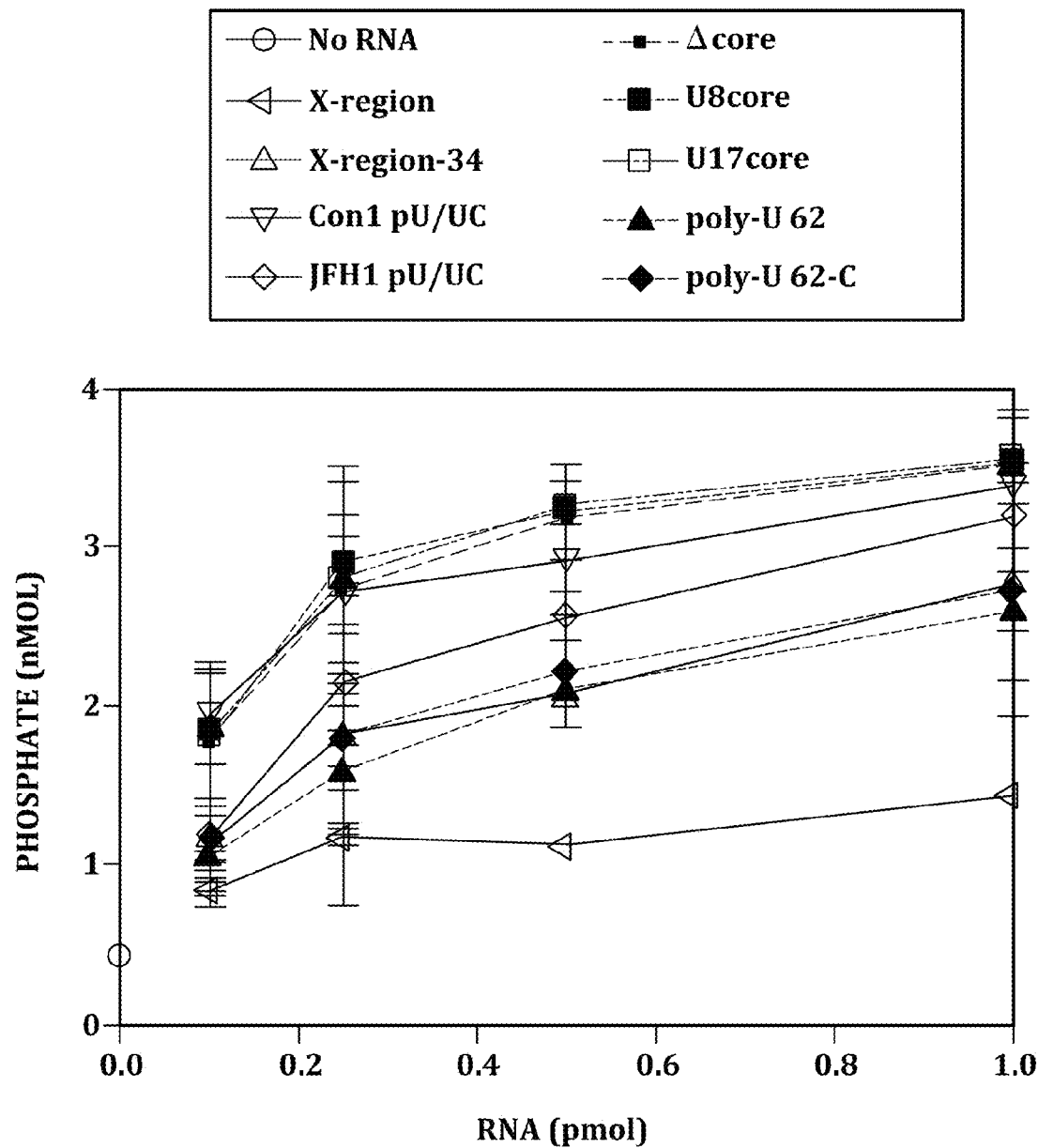

It was observed that all RNA constructs were able to bind and protect the RIG-I RD, albeit variably, from trypsin proteolysis in a dose-dependent manner (FIG. 3A). While no binding between RIG-I and the X-region RNA was previously observed in the EMSA analysis, the trypsin proteolysis assay revealed limited protection of the RIG-I RD by the X-region RNA. These differences in X-region binding likely reflect the higher amount of RIG-I required for protein visualization in the limited-trypsin proteolysis assay, and indicate that some degree of background binding occurs between RIG-I and ligand RNA in this assay. There was not a significant difference in the RD band intensity when comparing RIG-I protection from 1 pmol of non-signaling (X-region, Δcore) versus signaling RNAs, likely reflecting binding supported by the 5'-ppp on all of the RNAs (FIG. 3B). However, a dose-dependent protection of an approximately 78 kDa proteolytic product was detected representing a large portion of the RIG-I helicase domain and CARDs (FIG. 3A). This product was only detected for RNA constructs that exhibited PAMP activity to induce signaling to the IFN-β-promoter (X-region-U34, Con1 pU/UC, JFH1 pU/UC, U17core, poly-U 62, poly-U 62-C). In addition, there was a statistically significant difference in the helicase+CARDs band intensity when comparing protease protection of RIG-I resulting from 1 pmol of non-signaling versus signaling RNA (FIG. 3B; P=0.0147, two-tailed Student's t-test). These observations suggest that in addition to RD interactions, RNA interactions with the helicase domain may be required for induction of RIG-I signaling. No significant difference was detected in RIG-I ATPase activity when bound to the various RNA constructs, but the lowest ATPase activity was observed for RIG-I bound to the X-region RNA (FIG. 3C). Taken together, these results indicate that RNA binding interactions with the RIG-I RD are mediated by the 5'-ppp, and specific interactions between the helicase domain and poly-uridine tract of the HCV RNA are required for PAMP activity and to initiate RIG-I signaling.

HCV poly-U/UC RNA variants trigger differential anti-HCV and hepatic innate immune responses.

Figure 4A:
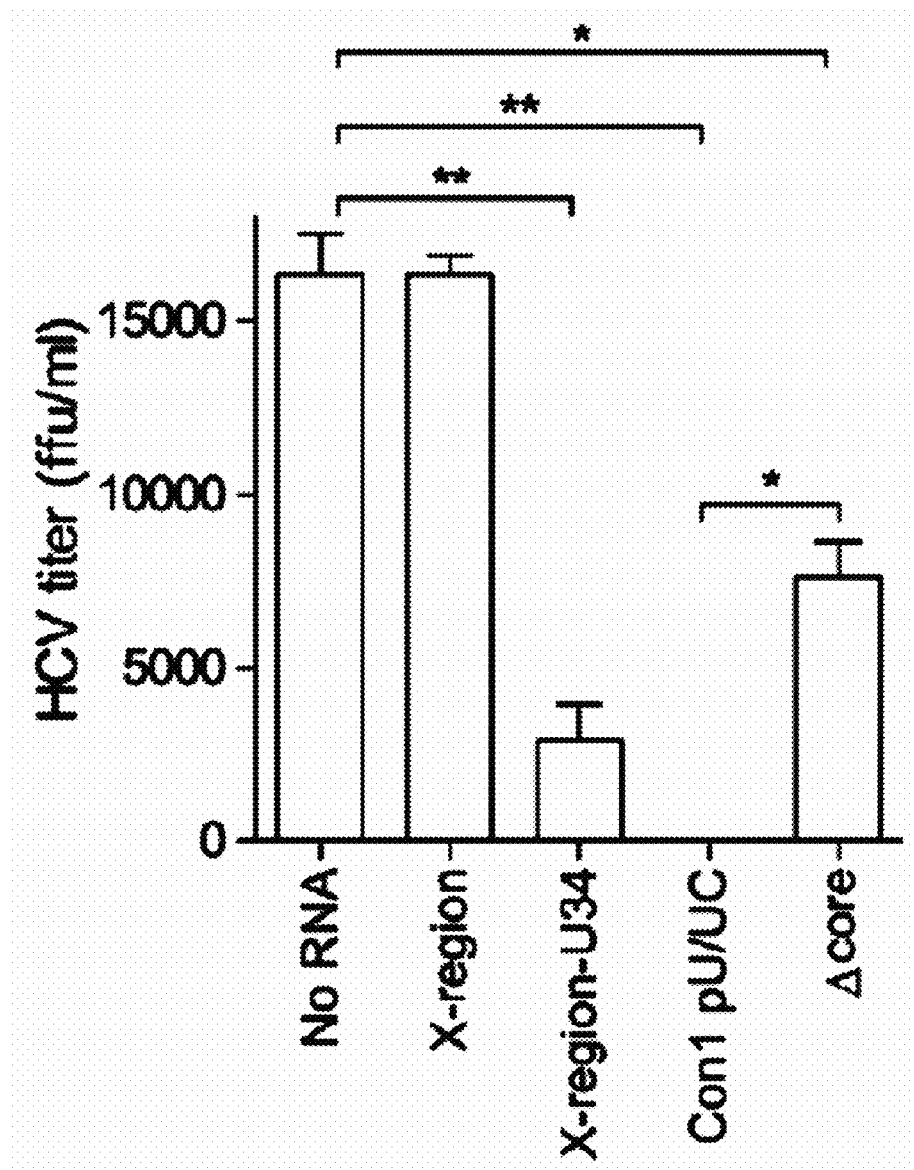
FIGS. 4A-4C illustrate that HCV poly-U/UC RNA variants trigger differential anti-HCV and hepatic innate immune responses.

To determine how the poly-U core sequence imposes PAMP activity that initiates RIG-I signaling of innate immunity, HCV production was measured in Huh7 cells that were first transfected with poly-U/UC RNA constructs to stimulate RIG-I signaling (FIG. 4A; No RNA, X-region, X-region-U34, Con1 pU/UC, and Δcore). 12 hours following RNA transfection, the cells were infected with HCV, and virus production was then assessed 48 hours later. It was observed that X-region RNA did not stimulate cellular suppression of HCV infection, whereas the Con1 pU/UC RNA stimulated a potent innate immune response that significantly suppressed HCV infection as compared to non-transfected control cultures (FIG. 4A). These analyses were applied to a non-parametric correlation test to reveal an inverse correlation between HCV production titer (ffu/ml) in the transfected cells and PAMP activity of the different RNAs as measured by the IFN-β-promoter fold index in Huh7 cells (Spearman r=−0.97; two-tailed P-value=0.0167). Overall, RNA constructs that induced higher levels of IRF-3 phosphorylation and IFN-β-promoter activity (X-region-U34, Con1 pU/UC; FIG. 1) were more effective in inducing RIG-I signaling to suppress HCV infection.

Figure 4B:
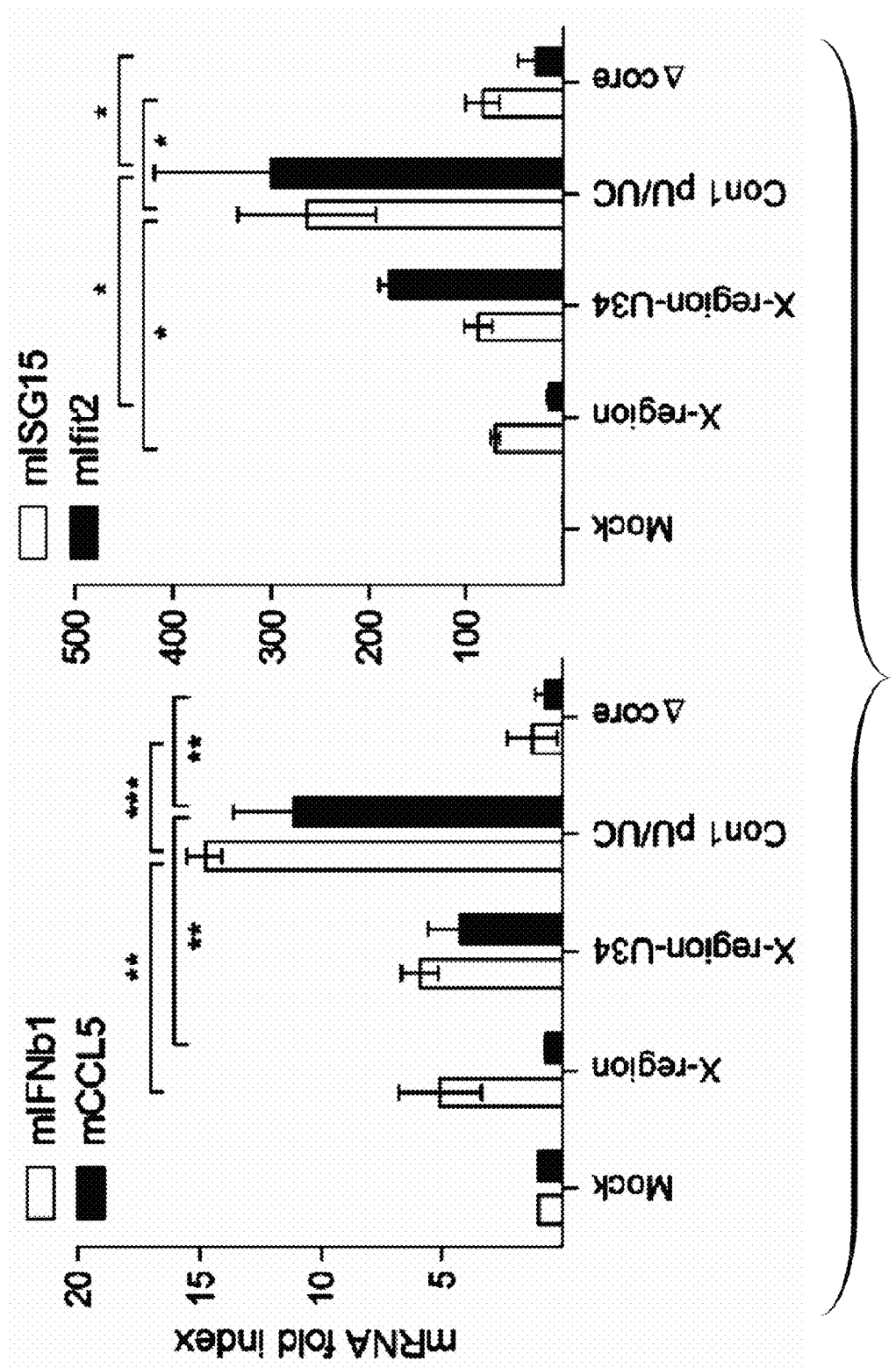
Figure 4C:
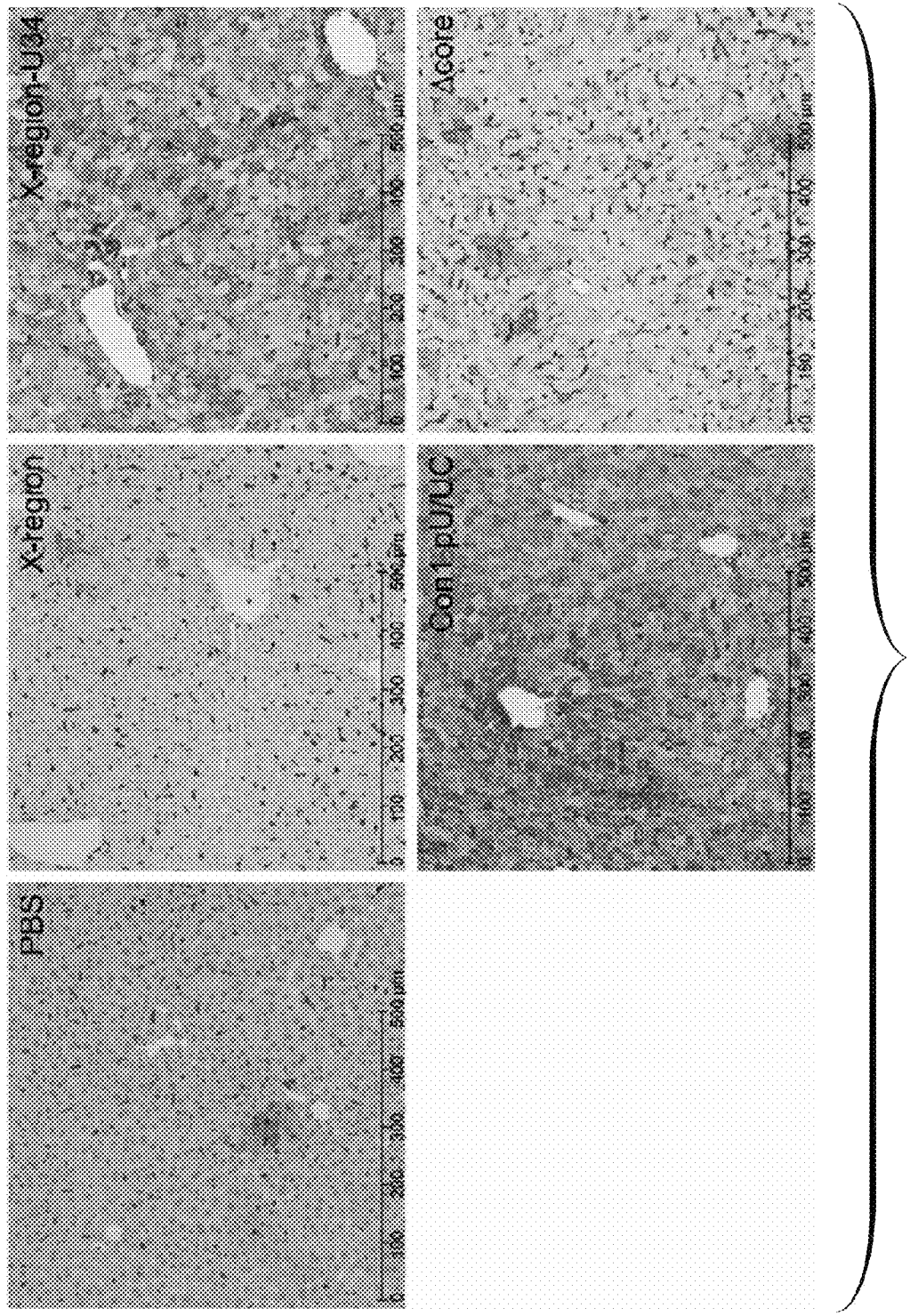

To determine if the differential PAMP activity of HCV RNA constructs imposed different levels of hepatic innate immune signaling and response in vivo, the ability of the constructs to trigger hepatic innate immune responses was examined using an intraperitoneal injection model in mice. This model recapitulates RIG-I-dependent PAMP signaling of hepatic innate immunity triggered by HCV RNA (Saito, T., et al., "Innate Immunity Induced by Composition-Dependent RIG-I Recognition of Hepatitis C Virus RNA," Nature 454:523-527 (2008)). Four poly-U/UC RNA variants (X-region, X-region-U34, Con1 pU/UC, and Δcore) were mixed with a lipid-based in vivo RNA transfection reagent and injected into wild-type C57BL/6 mice, and livers were collected 8 hrs later for assessment of the hepatic innate immune response. Expression of IFN-β mRNA and several interferon-stimulated genes (ISGs) were measured using real-time quantitative PCR (FIG. 4B). Hepatic IFN-β, CCL5, ISG15, and Ifit2 (also known as ISG54) mRNA expression were found to be significantly higher in mice transfected with Con1 pU/UC RNA compared to either X-region or Δcore RNA, indicating that a U-core of the pU/UC tract over 8 uridine nucleotides long is required for PAMP activity that induces the expression of IFN-β and other ISGs. Expression of hepatic Ifit2 mRNA was also higher in mice transfected with X-region-U34 RNA compared to X-region RNA, although the difference in gene expression did not reach statistical significance, implicating the requirement of poly-U RNA sequences for activation of hepatic innate immune responses in vivo. Expression of Ifit2 also correlated with ISG54 protein expression as shown by immunohistochemical staining of mouse liver sections (FIG. 4C). ISG54 protein expression was substantially higher in mice that received X-region-U34 or Con1 pU/UC RNA compared to either PBS, X-region, or Δcore RNA. Taken together, these studies indicate that >8 nt poly-U core of the HCV poly-U/UC tract is required for PAMP activity in vivo to drive RIG-I signaling of the hepatic innate immune response.

HCV Poly-U/UC Sequence Variability

Genetic variability of the poly-U/UC tract in HCV genome sequences containing full coverage of the 3'NTR that were available from the GenBank sequence database was examined. Non-redundant HCV poly-U/UC sequences were aligned to examine sequence variability. It was found that the poly-U/UC sequences varied in both length and nucleotide (nt) composition (see Table 2). In terms of length, the 5'arm ranged from 8-42 nt, the U-core ranged from 12-96 nt, and the 3'arm ranged from 0-80 nt. Nine pU/UC sequences contained a U-core with fewer than 20 uridine nucleotides, suggesting that these genomes likely have low RIG-I signaling activity. In general, HCV pU/UC genotype 1 sequences contained fewer purine nucleotides than genotype 2 sequences. Within the 5'arm of the pU/UC tract, genotype 1 nucleotide composition ranged from 12-44% purines compared to 16.7-50% purines in genotype 2 sequences. Within the 3'arm of the pU/UC tract, 41% of the genotype 1 sequences lacked purine nts (range of 0-11.6% purine composition), whereas genotype 2 sequence composition ranged between 5-11% purine nts in the 3'arm. We were unable to examine pU/UC sequence variability for genotypes 3-6 due to a deficiency of full-length 3'NTR sequences from those viral genotypes in the available sequence databases. Our analysis of HCV genome sequences reveal nt composition and length variability in the poly-U/UC tract of the HCV genome, and importantly within the U-core, suggesting that PAMP activity may differ substantially between HCV genotypes and within patient quasispecies populations.

TABLE 2

HCV poly-U/UC sequence variability.

| GenBank Acc. Gen.[a] | 5' arm[b] | U-core | 3' arm[c] | SEQ ID NO: |
|---|---|---|---|---|
| AJ238799.1b | 5'GGCCAUCCUGUUUUUUCCC(U11)C | U34 | CUCCUUUUUUUCCUCUUUUUUUCCUUUUCUUUCCUUU | 25 |
| AB001040.1b | 5'GGCCAUUC | U16 | CUUUCUUCUUU | 26 |
| AB016785.1b | 5'GGCCGUCCUG | U18 | | 27 |
| AB049088.1b | 5'GGCCAUUCCC | U81 | CUCUUCUUUUCUUUAUUCCUUCUUU | 28 |
| AB049089.1b | 5'GGCCGUUCC | U64 | CUUUUCCCCUUUUUUAUUUUUCUUUCUU | 29 |
| AB049090.1b | 5'GGCCAUCCUGUUUUUUUGUUUUUUC | U43 | CUUUUUUUCCCUUUUUUUUAUUUUAUUUUCUUUUGGU | 30 |
| AB049091.1b | 5'GGCCAUCCCCC | U96 | CCUCUUUUUUCCUUUUCUUCUUU | 31 |
| AB049095.1b | 5'GGCCGUUCUG | U85 | CCUUUUUUUUAUUCCUCUUUCU | 32 |
| AB049101.1b | 5'GGCCAUCCCCUUUG | U94 | AUUUCUCCUUCUUUU | 33 |
| AB080299.1b | 5'GGCCAUUCCU | U24 | CUUUUUUUUUCC(U24)CCUUUUCUUUCUUCUUU | 34 |
| AB249644.1b | 5'GGCCAUUUUC | U14 | CUUCUUUCUUUUUCUUUUUCUUUUUUUCCUUCUUU | 35 |
| AF054247.1b | 5'AGCCAUUCCUG | U28 | CUUUUUUUUUUCUUUCCUUUCCUUCUUUUUUUCCUUUC UUUUUCCCUUCUUUAAU | 36 |
| AF139594.1b | 5'GGCCAUUUCCUG(U15)GG | U39 | CCUUCCUUCUUUUUUUUUUUUUCCCUCUUUAU | 37 |
| AF333324.1b | 5'GGCCAUUUCCUG | U34 | CUUUUCCUUCUUUUUCCCUUUUUCUUUCUUCCUUCUUUA AU | 38 |
| AF176573.1b | 5'GGCCAUCCUGUG | U75 | AUUUCCUUUUCUU | 39 |
| AF356827.1b | 5'GGCCAACCUG(U26)CC | U34 | CCUUUUUUCUUUUUUUUUUUUUUUUUCCUUCCUUUU | 40 |
| AJ132997.1b | 5'GGCCAUCCUG | U16 | CUUUCUUU | 41 |
| AY460204.1b | 5'GGCCAUUUUCC | U23 | CUUUUUUUUCCUUUUUUUCUUUUUUUUCUUUUCUUU | 42 |
| D85018.1b | 5'GGCCAUUC | U35 | CGUUUCUUUUCUUCUUUUUGUUUUCUCUUCUCCUUUU | 43 |
| D85021.1b | 5'GGCCAUUCCCC(U14)CCGC | U33 | CUUUUUUUUCC(U27)CUUUUU | 44 |
| D85022.1b | 5'GGCCAUCCCCC(U13)CCGC | U21 | CUUUUUUUUUUUCUUUUUUUUUCC(U24)CUUUUCUUU UU | 45 |
| D85516.1b | 5'GGCCAUUC | U16 | CUUUCUUCUUU | 46 |
| D89815.1b | 5'GGCCAUCCCCUUC | U22 | CCUUUUCUUCUUU | 47 |
| EU857431.1b | 5'GGCCAUCCUGUUUUUUCCC(U11)C | U29 | CUCCUUUUUUUUCCUCUUUUUUUCCUUUUCUUUCCUUU | 48 |
| FN435993.1b | 5'GGCCGUCCUG(U19)CC | U67 | CUUCUUUCUUUCUU | 49 |
| GU133617.1b | 5'GGCCAUUCCUG | U53 | C(U17)CC(U20)CUUUCCUUCUUUUUUCCUUUCUUUC CUUCCUUCUUUAAU | 50 |
| AB520610.1a | 5'GGCCAUUCCUG | U16 | CUUUUGUUUUUUUG(U17)CCUUUC(U15)CCUUUCUU CUUUAAU | 51 |
| AF009069.1a | 5'GGCCAUUUCCUG | U20 | CUUUCCUUCUUUUUUCCUUUCUUUUCCUUCCUUCUUUAA U | 52 |
| AF009070.1a | 5'GGCCAUUUCCUG | U34 | CUUUUCCUUCUUUUUCCCUUUUUCUUUCUUCCUUCUUUA AU | 53 |
| AF009071.1a | 5'GGCCAUUUCCUG | U51 | C(U17)CC(U20)CUUUCCUUCUUUUUUCCUUUCUUUC CUUCCUUCUUUAAU | 54 |
| AF009072.1a | 5'GGCCAUUUCCUG(U14)CCC | U37 | CUUUUCCUUCUUUUUUUUCCUUUUUCUUUUUCCUUCCUUU AAU | 55 |
| AF009074.1a | 5'GGCAUCCUG | U64 | CUUUUCUUU | 56 |
| AF009075.1a | 5'ACACUCCAUUUCUUUUUUG | U67 | CUUUUUCUUUCCUUUCUUUUCUGACUUCUAAUUUUCCUU CUUA | 57 |

TABLE 2-continued

HCV poly-U/UC sequence variability.

| GenBank Acc. Gen.[a] | 5' arm[b] | U-core | 3' arm[c] | SEQ ID NO: |
|---|---|---|---|---|
| AF009076.1a | 5'GUCCUUCUG | U78 | CCUUACCCUUUCCUUCUUUUCUUCCUUUUUUUCCUUACUUU | 58 |
| AF009077.1a | 5'GGGUCCCCUUG | U12 | CUUUCCUUCUUUCCUUUCCUAAUCUUUCUUUCUU | 59 |
| AF011751.1a | 5'AGCCAUUCCUG | U28 | CUUUUUUUUUUUCUUUCCUUUCCUUCUUUUUUUCCUUUCUUUUUCCCUUCUUUAAU | 60 |
| AF271632.1a | 5'GGCCAUUCCUG(U15)G | U55 | CCUUUCCUUUUUUUUUUUUUUCCCUUUUUAU | 61 |
| AJ278830.1a | 5'GGCCAUCCUG(U22)C | U17 | CUUUUUUUUCUUCUUUUUCUUUCC(U24)CUUCUUUC | 62 |
| EF621489.1a | 5'GGCCAUUCCUG | U46 | CUUUUCCCUCUUUUUCUUCUCUUUUUCCUUCUUUAAU | 63 |
| AB047639.2a | 5'GCUAACUGUUCC | U43 | CUUUUUUUUUUUUUUCCCUCUUUCUUCCCUUCUCAUCUUAUUCUACUUUCUUUCUU | 64 |
| AB047640.2a | 5'GCUAACUGUUCC | U38 | C(U15)CCCUCUUUCUUCCCUUCUCAUCUUAUUCUACUUUCUUUCUU | 65 |
| AB047641.2a | 5'GCUAACUGUUCC(U11)C | U27 | CCUUCUUUCUUUCUUUCUUACCUUACUUUACUUUCUUUUCU | 66 |
| AB047642.2a | 5'GCUAACAGUUUCUC(U13)CC(U6)AUUUUA | U25 | AUUUUCUUUUCCUUUCUUUCUCACCUUACAUUACUUUCUUUCUU | 67 |
| AB047643.2a | 5'GCUAAUUUCCUUAUUG | U19 | CUUUCCAUUUCCUUCCUUCUUACUUCACUUUACCUUCUUUCU | 68 |
| AB047644.2a | 5'GCUAACUG | U77 | CCUUUCCUUUCUUUCUUACCUUACUUUACAUUCUUUUCU | 69 |
| AB047645.2a | 5'GCUAACUGUUCC | U70 | CUUUCCUUCCUUUCUCACCUUCUUUUACUUCUUUCCU | 70 |
| AF169002.2a | 5'GCUAACUG | U45 | CUUUUCUUUCCUUUCCUUCUUACUCUACUUUACUUUUCU | 71 |
| AF169003.2a | 5'GCUAACUGUUC | U78 | CUUUUCCUUCUUCUUUCUUACCUUAUUUCCUUCUUUCUU | 72 |
| AF169004.2a | 5'GCUAACUG | U30 | CUUUUUUUUCUUUCUUUCCUUCUUACCUUACUUUACUUUCUUUUCU | 73 |
| AF169005.2a | 5'GCUAACUG | U81 | CCUUUUUCCUUUUCCUUCUCUUUUUACCUUACUUUACUUUUCUU | 74 |
| AF177036.2a | 5'GCUAACUGUCCC | U84 | CUUUUUUUCUCUUUUUCCUUCUUUCUUACCUUAUUUUACUUUCUUUCCU | 75 |
| AY746460.2a | 5'GCUAACUGUCCCUUUUUUUUUG | U30 | C(U18)GUUUCUUUUCCUUCUCAUUUCCUUCUUAUCUUAAUUACUUCCUUUCCU | 76 |
| D67095.2a | 5'GCUAACUG | U39 | CCUUCUUCCUUUCCUUCUUACCUUACUUUAUUUCUUUCCU | 77 |
| D67096.2a | 5'GCUAACUG | U54 | CUUUCUUUUCUUUUCUCACCUUACUUUACUUCCUUUCUU | 78 |
| AB030907.2b | 5'GCUAGUUUUC | U24 | G(U14)CCUCUUUUUCCGUAUUUUUUUUUUUCCUCUUUUCUU | 79 |

[a]DNA sequences were obtained from GenBank, converted to RNA sequences, and aligned to examine sequence variability. Duplicate sequences were removed from the alignment, and sequences are listed as [GenBank Accession #.Genotype].
[b]Within the 5'arm of the pUC/UC tract, genotype 1 nucleotide composition ranged from 12.1-44.4% purine nucleotides; genotype 2 nucleotide composition ranged from 16.7-50% purine nucleotides.
[c]Within the 3'arm of the pU/UC tract, genotype 1 nucleotide composition ranged from 0 (16 sequences)-11.6% purine nucleotides; genotype 2 nucleotide composition ranged from 5.0-11.4% purine nucleotides.

Discussion

The present data demonstrate that a nucleotide polyuridine core of the HCV poly-U/UC tract is required for non-self recognition by RIG-I. Interspersed ribocytosine nucleotides between the poly-U sequences in the RNA were also important for optimal RIG-I signaling to the IFN-β promoter. The RIG-I/RNA binding studies found that RIG-I formed weaker interactions with HCV RNAs lacking poly-U sequences, while the 34 nt poly-U core of the poly-U/UC tract resulted in stimulating RIG-I/RNA binding interactions. Additionally, limited-trypsin proteolysis studies revealed that while the RIG-I RD interacts with the 5'-ppp terminus of HCV RNA, interactions between the helicase domain and poly-uridine HCV RNA sequences are required to activate RIG-I signaling. Finally, it was found that poly-U/UC RNA variants with high RIG-I signaling activity induced significant anti-HCV responses in cultured cells and also induced hepatic innate immune responses in vivo. Together, these studies identify long poly-uridine sequences (>U8) with interspersed ribocytosines as an HCV PAMP motif that drives optimal RIG-I signaling.

Previous studies have demonstrated the importance of the 5'-ppp for non-self recognition by RIG-I, wherein 5'-ppp was necessary but not sufficient for PAMP activity conferred by HCV RNA. The current results reveal the additional requirement for the U-core as a non-self signature to demonstrate the combinatorial presentation of multiple non-self motifs within a PAMP RNA. These include 5'-ppp, poly-uridine sequences and arrangements such as interspersed ribocytosine nucleotides, as well as length and certain secondary structures, to define an RNA as non-self. Such a requirement for combinatorial non-self recognition by RIG-I serves to provide several checkpoints for immune signaling that prevent spurious recognition of self, thus avoiding autoimmune reactions by requiring PAMP motifs that confer stable RIG-I interactions to induce activation of RIG-I signaling.

RIG-I is maintained in an auto-repressed conformation in uninfected cells. The initial step in RNA recognition and binding likely involves RD interaction with 5'-ppp RNA due to the high affinity of the RD for 5'-ppp moieties, which brings RNA structures in close contact with the helicase domains to allow for more specific RIG-I/RNA interactions. Following ligand RNA binding, RIG-I uses ATP hydrolysis to translocate along an RNA wherein upon engaging a PAMP motif it undergoes conformational rearrangements that release the N-terminal CARDs for downstream ubiquitination, translocation to mitochondrial-associated membranes, and interaction with MAVS to drive IFN expression. Recent RIG-I structural studies have found that a V-shaped linker/pincer/bridging domain connects the helicase domain 2 and the RD, and likely controls RIG-I conformational changes following RNA binding through strong interactions with helix α17 from helicase domain 1. In the present study, it was found that RIG-I/RNA binding association differences correlated with PAMP activity, revealing that a >8 nt poly-U core of the poly-U/UC tract was required to stimulate potent RIG-I/RNA binding interactions, form contacts with the helicase domain, and activate RIG-I signaling to the IFN-β-promoter.

These results imply a model of RIG-I interaction with the HCV PAMP RNA in which the RIG-I RD interacts with the 5'-ppp terminus of HCV ligand RNA. While kissing loop interactions between structures in the 5' and 3' NTR of the HCV genomic strand RNA would be expected to bring the 5'-ppp into proximity to the poly-U/UC tract for non-self recognition, these motifs are each present in the anti-genomic strand replication intermediate HCV RNA (5'-ppp with poly-A/AG) where they confer PAMP activity through RIG-I recognition. This process of RIG-I binding brings RNA sequence domains into close proximity for PAMP recognition and binding with the helicase domain, thus providing an opportunity for RIG-I to form more stable/specific RNA contacts. ATP hydrolysis allows RIG-I to translocate on the RNA and "scan" for HCV PAMP sequences. Following the recognition of an HCV PAMP motif, defined here as poly-uridine sequences (>U8) with interspersed ribocytosines, RIG-I likely undergoes a final conformational change to activate signaling via the CARDs and drive the innate immune response to infection.

All HCV genomes contain a poly-U sequence in the 3' NTR; therefore, certain restrictions must exist which prevent viral evolution of this genomic region to mitigate RIG-I recognition. Indeed, previous studies have reported that the poly-U/UC tract is essential for HCV RNA replication. A minimum pU/UC core length of 26 consecutive uridine nucleotides (U26) has been indicated as required for HCV replication, while a core length of 33 uridine nucleotides has been indicated as necessary for optimal HCV RNA amplification in cell culture. A detailed study revealed that in addition to the long-range kissing-loop interactions between the NS5B SL3.2 and the 3'SL2 loops in the genomic RNA, a poly-U/UC tract with a minimum U-core length of 33 uridines (U33) is also necessary for HCV RNA replication. In addition, viral mutants with truncated poly-U core lengths had impaired replication kinetics (U27 core) or absent replication (U7 or U16 core) until selection for longer U-core lengths resulted in greater replication fitness. The strong selective pressure for a long uninterrupted poly-U nucleotide sequence within the pU/UC tract suggests that this region of the HCV RNA may mediate essential interactions with replication factors, thus explaining the evolution restriction of this viral genomic region. Due to the high fitness cost, HCV is unable to prevent RIG-I recognition via genomic sequence evolution, which makes the HCV poly-U/UC tract an optimal target for non-self recognition. In the present study, it was found that deletion of the U-core resulted in the loss of PAMP activity to drive RIG-I signaling to the IFN-β-promoter. However, a poly-U core exceeding 8 uridine nucleotides restored signaling, indicating that RIG-I recognition of the poly-U core can occur at a U-core length below what is required for efficient HCV RNA replication. This restriction also explains why the viral NS3/4A protease has evolved to target the downstream signaling protein MAVS for cleavage in order to suppress the RIG-I pathway and evade restriction otherwise imposed by the innate immune response in HCV patients.

HCV encompasses 6 major genotypes and multiple subtypes, and this increased viral diversity results in highly variable treatment outcomes. Standard treatment is currently limited to interferon (IFN)-based therapies, and although two viral protease inhibitors were recently approved for use in humans, these drugs are to be applied in combination with IFN therapy. Overall, treatment with IFN-based therapy results in viral clearance in only 50% of infected subjects, and HCV genotypes 1a and 1b are the least responsive to standard therapies. RIG-I recognition of HCV RNA and subsequent activation of antiviral immune responses may influence the response to therapy, especially in subjects taking viral protease inhibitors where the RIG-I pathway blockade by the viral NS3/4A protease would be temporarily lifted. Genetic variability within the poly-U/UC tract of the HCV genome between different viral genotypes was examined using sequences available from the GenBank database. In general, HCV pU/UC genotype 1 sequences contained fewer purine nucleotides than genotype 2 sequences. In addition, nine pU/UC sequences contained a U-core with fewer than 20 consecutive uridine nucleotides, likely representing poorly replicating genomes with decreased fitness. Further studies will help determine whether innate immune activation differs substantially between HCV genotypes and within patient quasispecies populations to impact the outcome of HCV infection and immunity.

HCV evades the host immune response using multiple mechanisms, while host PRRs target critical regions of viral RNA or protein to suppress HCV replication. Understanding the virus-host interface regulating innate immunity against HCV is necessary to develop new therapies and restrict infection. In the present study, it was found that a 5'-ppp and a poly-U core exceeding 8 uridine nucleotides within the HCV poly-U/UC tract are required for non-self recognition of HCV RNA by RIG-I. In addition, RIG-I recognition of the U-core within the poly-U/UC tract can activate innate anti-HCV immune responses in vitro and hepatic innate immune responses in vivo, thus providing a potential target for restricting HCV infection. Similar poly-uridine molecules could be used to induce antiviral immune responses in conjunction with IFN-based and viral protease-targeted therapies to improve HCV clearance in chronically-infected subjects. In addition, vaccine strategies that activate RIG-I signaling pathways may be required to induce appropriate immune responses to RNA viruses, including HCV, which are highly sensitive to IFN and other innate antiviral ISGs in the absence of viral antagonism. Given that RIG-I can activate innate antiviral immune responses upon recognition of poly-uridine sequence motifs, incorporation of poly-U sequences into vaccine vectors could act as an adjuvant to mimic the natural early immune response following virus infection.

Materials and Methods

Ethics Statement

C57BL/6 mice were housed under pathogen-free conditions in the animal facility at the University of Washington. Experiments and procedures were performed with approval from the University of Washington Institutional Animal Care and Use Committee (IACUC; protocol number 4158-01). Methods for mice use and care were performed in accordance with the guidelines of the University of Washington Institutional Animal Care and Use Committee, and also followed the recommendations in the Guide for the Care and Use of Laboratory Animals of the National Institutes of Health.

Cells and Viruses

Huh7 cells and Huh7.5 cells were cultured in Dulbecco's modified Eagle medium (DMEM) supplemented with 10% fetal bovine serum (FBS) and 100 µg/ml of penicillin and streptomycin. Huh7.5 cells encode a mutant RIG-I protein that cannot signal (Sumpter, R., Jr., et al., "Regulating Intracellular Antiviral Defense and Permissiveness to Hepatitis C Virus RNA Replication Through a Cellular RNA Helicase, RIG-I," *J. Virol.* 79:2689-2699 (2005); Blight, K. J., et al., "Highly Permissive Cell Lines for Subgenomic and Genomic Hepatitis C Virus RNA Replication," *J. Virol.* 76:13001-13014 (2002)). The hepatitis C virus (HCV) used in these studies was a cell culture adapted virus that was produced from the pJFH-1 HCV 2a infectious clone as previously described (Zhong, J., et al., "Robust Hepatitis C Virus Infection In Vitro," *Proc. Nat'l Acad. Sci. USA* 102: 9294-9299 (2005)).

Plasmids and Proteins

The plasmids pIFN-β-luc, pCMV-*Renilla*-luc (Foy, E., et al., "Regulation of Interferon Regulatory Factor-3 by the Hepatitis C Virus Serine Protease," *Science* 300:1145-1148 (2003)), and pJFH-1 (Zhong, J., et al., "Robust Hepatitis C Virus Infection In Vitro," *Proc. Nat'l Acad. Sci. USA* 102: 9294-9299 (2005); Wakita, T., et al., "Production of Infectious Hepatitis C Virus in Tissue Culture From a Cloned Viral Genome," *Nat. Med.* 11:791-796 (2005)) have been described. The pX-region-c4 plasmid was generated by inserting an HCV Con1 X-region T7 promoter-linked PCR product into the pCR2.1 vector (Invitrogen) as per the manufacturer's instructions. Purified recombinant full-length RIG-I protein was produced as previously described (Jiang, F., et al., "Structural Basis of RNA Recognition and Activation by Innate Immune Receptor RIG-I," *Nature* 479:423-427 (2011)).

RNA Methods.

All in vitro transcribed RNAs contain a 5'-triphosphate (5'-ppp) and three guanine nucleotides at the 5' end to enhance T7 polymerase transcription. HCV X-region 5'-ppp RNA was synthesized from a T7 promoter-linked PCR product generated from the pX-region-c4 plasmid using the primers X-regionF (5'-TAATACGACTCACTATAGGTG-GCTCCATCTTAGCCCTA-3') (set forth as SEQ ID NO:80) and X-regionR (5'-ACTTGATCTGCAGAGAGGCCAG-TATCA-3') (set forth as SEQ ID NO:81). The amplified PCR product was purified by agarose gel extraction using the QIAquick gel extraction kit (Qiagen) as per the manufacturer's protocol. Full-length HCV RNA was produced from the pJFH-1 plasmid (genotype 2a) as previously described (Zhong, J., et al., "Robust Hepatitis C Virus Infection In Vitro," *Proc. Nat'l Acad. Sci. USA* 102:9294-9299 (2005)). All other 5'-ppp RNA products were generated using synthetic DNA oligonucleotide templates (Integrated DNA Technologies) and the T7 RNA polymerase as previously described (Milligan, J. F., et al., "Oligoribonucleotide Synthesis Using T7 RNA Polymerase and Synthetic DNA Templates," *Nucleic Acids Res.* 15:8783-8798 (1987)) using the T7 MEGAshortscript kit (Ambion) as per the manufacturer's instructions. Following in vitro transcription, DNA templates were removed with DNAse treatment and unincorporated nucleotides were removed from the reaction using illustra MicroSpin G-25 columns (gel filtration column chromatography, GE Healthcare). RNA was then precipitated using ethanol and ammonium acetate as described by the manufacturer, then resuspended in nuclease-free water. RNA concentration was determined by absorbance using a Nanodrop spectrophotometer. RNA quality was assessed on denaturing 8 M urea polyacrylamide gels for short RNA transcripts (50-150 nts) (not shown). Full-length HCV RNA quality was assessed on a denaturing formaldehyde-agarose gel (not shown).

Luciferase Reporter Assay

Huh7 or Huh7.5 cells were plated on 10 cm dishes, and 24 hours later cells were transfected with 5.76 µg pIFN-β-luc (firefly luciferase) and 0.24 µg pCMV-*Renilla*-luc (*Renilla luciferase*) plasmids using the FuGENE 6 transfection reagent and protocol (Roche). Transfected Huh7 or Huh7.5 cells were incubated at 37° C. for 18 hours, then split into 48-well plates and incubated for an additional 12 hours prior to RNA transfection. RNA transfection was conducted in a 48-well plate format using the TransIT-mRNA Transfection kit (Mirus) as per the manufacturer's instructions. RNA transfection was conducted using either equal numbers of moles of each RNA or 350 ng RNA, depending on the experiment. Following RNA transfection, cells were incubated an additional 18 hours and luciferase activity was measured using the Dual-Luciferase reporter assay system (Promega). All conditions and experiments were conducted in triplicate.

EMSA

Various amounts of purified recombinant full-length RIG-I protein (0-30 pmol) were mixed with 10 pmol RNA and 10 ml ATPase reaction buffer (20 mM Tris-HCl, pH 8.0; 1.5 mM $MgCl_2$; 1.5 mM DTT). Reactions were incubated at 37° C. for 15 minutes, then 4× native sample buffer (25 mM Tris-HCl, pH 6.8; 0.02% bromophenol blue; 60% glycerol) was added to samples. Products were separated on a 2% agarose gel (TAE, pH 7.2) and RNA was visualized using SYBR Gold nucleic acid stain (Invitrogen). Gel-shift images were analyzed using ImageJ software (National Institutes of Health), and RNA-protein binding curves were graphed using Prism 5 software (GraphPad).

Limited Trypsin Proteolysis of RIG-I/RNA Complexes

Various amounts of RNA (0-10 pmol) were mixed with 30 pmol purified RIG-I protein, 2 µl of 5× reaction buffer (20 mM Tris-HCl, pH 8.0; 1.5 mM $MgCl_2$; 1.5 mM DTT; 70 mM KCl), 0.67 µl AMP-PNP (10 mg/ml), and nuclease-free water up to 10 µl total volume. Reactions were incubated for 5 minutes at room temperature. Sequencing grade TPCK-treated modified trypsin (Promega) was added to the RIG-I/RNA mixtures at a protease:protein ratio of 1:20 (w/w), and the reactions were incubated at 37° C. for 15 minutes. Proteolysis was stopped by adding 0.5 ml TLCK (1 mg/ml) and incubating reactions for 5 minutes at room temperature. SDS-PAGE Laemmli sample buffer (Bio-Rad) was then added to the samples and reaction products were analyzed by SDS-PAGE followed by silver stain using the Silver-Quest silver staining kit (Invitrogen) as per the manufacturer's instructions.

ATPase Assay

Various amounts of RNA (0-1 pmol) were mixed with 5 pmol purified RIG-I protein in a total of 25 µl ATPase reaction buffer (20 mM Tris-HCl, pH 8.0; 1.5 mM $MgCl_2$; 1.5 mM DTT). Reactions were incubated at 37° C. for 15 minutes, ATP (Sigma) was added to the reaction mixture at a final concentration of 1 mM, and the reactions were incubated at 37° C. for 15 minutes. Free-phosphate concentration was determined using BIOMOL Green reagent (Enzo Life Sciences) in a microplate format and absorbance was measured at $OD_{630}$ nm.

Immunoblotting and Antibodies

Protein extracts were prepared and analyzed by immunoblotting as previously described (Foy, E., et al., "Regulation of Interferon Regulatory Factor-3 by the Hepatitis C Virus Serine Protease," *Science* 300:1145-1148 (2003)) using antibodies specific to phospho-IRF-3 Ser396 (Cell Signaling Technology), IRF-3 (from A. Rustagi at University of Washington, Seattle), RIG-I (Enzo Life Sciences), ISG56 (from G. Sen at Cleveland Clinic Foundation, Cleveland), and tubulin (Sigma). All secondary antibodies were obtained from Jackson ImmunoResearch, and immunoreactive bands were detected with the Amersham ECL Plus Western Blotting Detection Reagents (GE Healthcare).

HCV Infections

Huh7 cells were plated on 48-well plates and incubated for 12-24 hours at 37° C. Cells were transfected with 350 ng RNA using the TransIT-mRNA Transfection kit (Mirus) as per the manufacturer's instructions and incubated at 37° C. for 12 hours. The transfection media was removed and the cells were washed gently with complete DMEM. Transfected cells were then infected with cell culture adapted JFH-1 HCV (MOI=0.1) in 100 ml total media volume and incubated at 37° C. for 3 hours. The virus inoculum was then removed and 300 µl complete DMEM was added, and the cells were incubated at 37° C. for 48 hours. HCV-infected cell supernatants were collected and titered on Huh7.5 cells. For the HCV titer assay, Huh7.5 cells were plated on 48-well plates and incubated for 12-24 hours at 37° C., media was removed, and 100 ml of infectious supernatants were added to cells using the following dilutions (no dilution, 1:2, 1:10, 1:100, 1:1000). Cells were incubated with supernatants at 37° C. for 3 hours, the virus inoculum was removed and complete DMEM (300 µl) was added, and cells were incubated at 37° C. for 48 hours. Media was then removed and the cells were washed 2 times with phosphate buffered saline (PBS). Huh7.5 cells were fixed with 4% paraformaldehyde for 30 minutes at room temperature. Cell monolayers were permeablized with a solution of PBS/0.2% Triton X-100 for 15 minutes at room temperature, washed with PBS, and then incubated with 10% fetal bovine serum in PBS for 10 minutes. After rinsing with PBS, cells were incubated with a human antiserum specific for HCV for 1 hour, washed three times with PBS, then incubated for 1 hour with donkey anti-human-HRP secondary antibody. Cells were washed 3 times with PBS, then immunoreactive cells were visualized using the Vector VIP substrate kit for peroxidase (Vector Laboratories) following the manufacturer's instructions. Cells were allowed to dry and focus forming units were counted to determine HCV titers in the cell supernatants. All conditions were conducted in triplicate.

Mice and Immunohistochemistry Staining

Mouse experiments and procedures were performed with approval from the University of Washington Institutional Animal Care and Use Committee. C57BL/6 mice were transfected via intraperitoneal injection with 200 µg RNA using a lipid-based in vivo RNA transfection reagent (Altogen Biosystems), and were euthanized 8 hours later for comparative measurement of mRNA and protein expression. Following systemic PBS perfusion to remove contaminating blood cells, mouse livers were recovered and fixed in 4% formalin solution for 24 hours and immunohistochemistry staining for mouse ISG54 was performed as previously described (Saito, T., et al., "Innate Immunity Induced by Composition-Dependent RIG-I Recognition of Hepatitis C Virus RNA," *Nature* 454:523-527 (2008)) by the Histology and Imaging Core at the University of Washington.

Real-Time PCR

Mouse liver sections were collected following systemic PBS perfusion and soaked in RNAlater reagent (Ambion). Liver sections were homogenized and RNA was extracted using the RNeasy kit (Qiagen). Synthesis of cDNA was conducted using the iScript select cDNA synthesis kit (Bio-Rad) with both oligo(dT) and random primers following the manufacturer's instructions. One-step real-time quantitative PCR was performed with SYBR Green master mix (Applied Biosystems) using an ABI PRISM 7300 Real-Time PCR System. Gene specific primers for mouse IFN-β, CCL5, Ifit2, ISG15, and GAPDH were purchased from SABiosciences. Results were normalized to the expression of mouse GAPDH mRNA.

Example 2

Summary

As described above, binding of Pathogen Associated Pattern (PAMP) RNA by RIG-I-like receptors (RLRs), RIG-I or MDA5, results in induction of signaling events that trigger type I interferon production and direct the innate immune response that limits pathogen infection, such as limiting virus replication and spread. RLRs trigger interferon production through the activation of latent transcription factors IRF-3 and NF-κB in a process that is mediated by a signalosome assembled on the membrane-associated adaptor molecule, MAVS. Toward defining the actions of PAMP signaling by RLRs through MAVS in innate immunity against virus infection, it was established above in Example 1 that HCV PAMP RNA requires at least a 5'-triphosphate (5'-ppp) in association with a minimal poly U core sequence. The strength of RLR signaling was increased with the inclusion of an interspersed ribocytosine residue to provide a poly-U/UC sequence. The poly-U/UC PAMP is immunostimulatory when transfected into cells or injected in mice in vivo, and thus represents a therapeutic agent for treatment of viral infection. The poly-U/UC RNA induces RIG-I signaling through the MAVS adaptor protein, but how these processes function to mechanistically limit virus infection is not fully understood.

To further investigate the utility of a poly-U/UC sequence for use in stimulating innate immune responses, additional analyses of the host response induced by poly-U/UC PAMP motif from hepatitis C virus (HCV) genome RNA were conducted.

Results and Discussion

The RIG-I signaling capacities of various poly-U/UC RNA constructs derived from HCV (Con1 strain) were assayed in Huh7 cells using an IFN-β luciferase reporter assay. $10^5$ cells were co-transfected with 200 ng of each RNA construct along with IFN-beta luc reporter promoter plasmid. The poly-U/UC RNA constructs included: poly-U/UC, which is listed in Table 1 as "pU/UC C67U"; U24 Core, which is a derivative of the poly-U/UC construct with a 24 residue U-core; U17 Core, which is a derivative of the poly-U/UC construct with a 17 residue U-core; U12 Core, which is a derivative of the poly-U/UC construct with a 12 residue U-core; U8 Core, which is a derivative of the poly-U/UC construct with an 8 residue U-core; and Delta Core, which is a derivative of the poly-U/UC construct but with the U-core removed. At 16 hours post-transfection, the cells were harvested and assayed for luciferase activity. As illustrated in FIG. 5A, the poly-U/UC construct elicited the greatest induction of IFN-β luciferase reporter, with the strength of the induction decreasing with the decrease of U-core length. IFN-β luciferase reporter was not detected with the U8 Core or Delta-Core constructs. This indicates that poly-U/UC RNA PAMP constructs with poly-U core sequences over 8 nucleotides long can stimulate detectable expression of IFN-β.

In a parallel assay, Huh7 cells similarly transfected were harvested and assayed for abundance of total IRF-3 and phospho-IRF-3 (P-IRF-3), which is indicative of an innate immune response signaling cascade, and actin as a control. FIG. 5B illustrates that co-transfection with the poly-U/UC RNA PAMP constructs containing poly-U core sequences over 8 nucleotides long can cause the detectable phosphorylation of IRF-3.

Having established that poly-U/UC RNA PAMP constructs with poly-U core sequences over 8 nucleotides can detectably stimulate innate immune response signaling, the constructs were assayed for the ability to reduce viral load in cells for a variety of different RNA viruses, namely Japanese encephalitis virus (JEV); vesicular stomatitis virus (VSV); dengue virus 2 (DV); West Nile virus (WNV); hepatitis C virus (HCV); and, respiratory syncytial virus (RSV). Cells were infected with the indicated virus. After three hours of the infection, the cells were treated with poly-U/UC RNA PAMP constructs of varying U-core lengths, or mock treated for control. At 72 hours post treatment, the cells were harvested and intracellular viral RNA levels were measured using virus-specific RT qPCR. The results are illustrated in FIG. 6 through FIG. 8. FIG. 6 illustrates the significant reduction in viral RNA for all viruses tested after administration of the poly-U/UC PAMP RNA construct. FIG. 7 illustrates the significant reduction in viral RNA for all viruses tested after administration of the poly-U/UC PAMP RNA derivative construct with a U17 core. Finally, FIG. 8 illustrates the significant reduction in viral RNA for all viruses tested after administration of the poly-U/UC PAMP RNA derivative construct with a U12 core.

These data demonstrate that the tested poly-U/UC PAMP RNA constructs, with U-core sequences as short as 12 nucleotides long, have significant antiviral activity in infected cells. Moreover, consistent with the data described above in Example 1, the varying lengths of the poly-U core result in varying strength innate response signaling. Accordingly, the relative strength of an innate immune response can be controlled through the rational design of poly-U/UC PAMP RNA constructs, which can be useful to avoid over-stimulation of the innate response mechanisms.

Method and Materials

Cells and Viruses

Huh7 cells and Huh7.5 cells were cultured in Dulbecco's modified Eagle medium (DMEM) supplemented with 10% fetal bovine serum (FBS) and 100 µg/ml of penicillin and streptomycin. Huh7.5 cells encode a mutant RIG-I protein that cannot signal. The hepatitis C virus (HCV) used in these studies was a cell culture adapted virus that was produced from the pJFH-1 HCV 2a infectious clone.

Plasmids and Proteins

The plasmids pIFN-β-luc, pCMV-Renilla-luc, and pJFH-1 encode human IFN-beta promoter driving firefly luciferase expression, and a CMV promoter driving Renilla luciferase expression, respectively. The pX-region c4 plasmid was generated by inserting an HCV Con1 X-region T7 promoter-linked PCR product into the pCR2.1 vector (Invitrogen) as per the manufacturer's instructions.

RNA Methods

All in vitro transcribed RNAs contain a 5'-triphosphate (5'-ppp) and three guanine nucleotides at the 5' end to enhance T7 polymerase transcription. For negative control, HCV X-region 5'-ppp RNA was synthesized from a T7 promoter-linked PCR product generated from the pX-region c4 plasmid using the primers X-regionF and X-regionR, described above in Example 1 and set forth herein as SEQ ID NOS:80 and 81, respectively. The amplified PCR product was purified by agarose gel extraction using the QIAquick kit (Qiagen) as per the manufacturer's protocol. 5'-ppp RNA products were generated using synthetic DNA oligonucleotide templates (Integrated DNA Technologies) and the T7 RNA polymerase as described by the manufacturer using the T7 MEGAshortscript kit (Ambion). The various derivatives of the poly-U/UC RNA constructs included, namely the U12, U17, and U24 core RNA constructs differed from the poly-U/UC RNA ("pU/UC C67U" in Table 1) by virtue of shorter poly-U core sequences, as indicated, and with a C21 nucleotide at the 3' end. Following in vitro transcription, DNA templates were removed with DNAse treatment and unincorporated nucleotides were removed from the reaction using illustra MicroSpin G-25 columns (gel filtration column chromatography, GE Healthcare). RNA was then precipitated using ethanol and ammonium acetate as described by the manufacturer, then resuspended in nuclease-free water. RNA concentration was determined by absorbance using a Nanodrop spectrophotometer. RNA quality was assessed on denaturing 8M urea polyacrylamide gels for short RNA transcripts (50-150 bp). Full-length HCV RNA quality was assessed on a denaturing formaldehyde-agarose gel.

Luciferase Reporter Assay

Huh7 cells were plated on 10 cm dishes, and 24 hours later cells were transfected with 5.76 µg pIFN-β-luc (firefly luciferase) and 0.24 µg pCMV-Renilla-luc (Renilla luciferase) plasmids using the FuGENE 6 transfection reagent and protocol (Roche). Transfected Huh7 or Huh7.5 cells were incubated at 37° C. for 18 hours, then split into 48-well plates and incubated for an additional 12 hours prior to RNA transfection. RNA transfection was conducted in a 48-well plate format using the TransIT-mRNA Transfection kit (Mirus) as per the manufacturer's instructions. RNA transfection was conducted using either equal numbers of moles of each RNA or 350 ng RNA, depending on the experiment. Following RNA transfection, cells were incubated an additional 18 hours and luciferase activity was measured using the Dual-Luciferase reporter assay system (Promega). All conditions and experiments were conducted in triplicate.

Immunoblotting and Antibodies

Protein extracts were prepared and analyzed by immunoblotting as previously described in Schnell, G., et al., "Uridine Composition of the Polu-U/UC Tract of HCV RNA Defines Non-Self Recognition by RIG-I," PLOS Pathogens 8(8):e1002839 (2012) using antibodies specific to phospho-IRF-3 Ser396 (Cell Signaling Technology), IRF-3 (from A. Rustagi at University of Washington, Seattle), and actin (Sigma). All secondary antibodies were obtained from Jackson ImmunoResearch, and immunoreactive bands were detected with the Amersham ECL Plus Western Blotting Detection Reagents (GE Healthcare).

Virus Infection

Respiratory syncytial virus (RSV) was prepared from HeLa cells using virus stocks obtained from M. E. Peeples (Ohio State University). Infected HeLa cells and culture medium were collected at 48 hrs post-infection. The cell pellet was resuspended in PBS supplemented with 2 mM EDTA, and lysed by successive cycles of freezing and thawing. Cellular debris was removed by centrifugation, and the supernatant pooled with the previously collected culture medium. Virus was concentrated with the addition of 50% (v/v) polyethylene glycol (PEG, FW=8000) in NTE buffer (150 mM NaCl, 50 mM Tris base pH 7.2, 10 mM EDTA) to a final concentration of 10% (v/v) PEG, followed by centrifugation at 10,000 rpm. The virus pellet was reconstituted in 20% sucrose in NTE buffer, and further purified by sedimentation using a discontinuous gradient of 35 and 60% (w/v) sucrose in NTE buffer that was centrifuged at 37000 rpm for 1 hr at 4° C. The purified virus stock was titrated on HeLa cells and assayed for focus forming unitus (FFU) at 48 hrs post-infection. Vesicular stomatitis virus (VSV) was a gift from Dr. Phillip Marcus (University of Connecticut). Dengue virus type 2 was a gift from Lee Gehrke (Massachusetts Institute of Technology and Harvard Medical School). Hepatitis C virus (HCV) was produced from the JFH1 HCV infectious clone as described by Saito, T., et al., "Innate Immunity Induced by Composition-Dependent RIG-I Recognition of Hepatitis C Virus RNA," Nature 454:523-527 (2008). Japanese Encephalitis virus (JEV; strain 14-14-2) was a gift from Michael Diamond, (Washington University). West Nile virus strain TX-02 was isolated and prepared as described in Keller, B. C., et al., "Resistance to alpha/beta interferon is a determinant of West Nile virus replication fitness and virulence," J. Virol. 80:9424-9434 (2006). Virus infections were conducted as follows: Cells were infected with virus at multiplicity of infection (MOI) of 1.0. $5 \times 10^5$ cells were cultured in a 6 cm dish in complete media with 10% fetal bovine serum (DME). Cells were transfected with transfection reagent alone (media control) or with the indicated PAMP RNA (1 ug/dish). 16 hours later the media was removed and the cells were rinsed 3 times with fresh serum-free media. After the final rinse, the indicated virus in serum-free media was added to the culture, after which the cultures were incubated for 4 hr at 37° C. After 4 hr the media was removed and replaced with DME, and the cells were cultured for an additional 48 hrs. Cells were then harvested by removing the media, washing the cell monolayer in PBS and scrapping the cells off of the culture dish. Cell pellets were collected and subjected to freeze-thaw for cell lysis, and cell extracts were prepared for immunoblot analysis or RT-qPCR analysis.

PCR

RNA was isolated from cell extracts using the RNA isolation kit from Qiagen. Synthesis of cDNA was conducted using the iScript select cDNA synthesis kit (Bio-Rad) with both oligo(dT) and random primers following the manufacturer's instructions. One-step real-time quantitative PCR was performed with SYBR Green master mix (Applied Biosystems) using an ABI PRISM 7300 Real-Time PCR System. Gene specific primers for human or mouse GAPDH were purchased from SABiosciences. Virus-specific primers for HCV, reovirus, JEV, DV, VSV, and RSV were from Loo et al., (Loo, Y.-M., et al., "Distinct RIG-I and MDA5 signaling by RNA viruses in innate immunity," J. Virol. 82:335-345 (2008)). Results were normalized to the expression of mouse GAPDH mRNA.

Statistics

Data sets were analyzed by Student's T test for assessment of significant differences. P value<0.5 represents statistically significant differences.

Example 3

Summary

As described above, RLRs serve to recognize and bind to viral product RNA to identify nonself for immune response induction. RIG-I is best understood in this capacity. In the case of hepatitis C virus (HCV) infection, RIG-I recognizes and binds to HCV genome RNA through recognition of free 5' triphosphate (5'-ppp) and the poly-uridine/cytosine (poly-U/UC) present in the viral RNA 3' nontranslated region (NTR) (collectively known as the poly-U/UC PAMP). The poly-U/UC PAMP is immunostimulatory when transfected into cells or injected in mice in vivo, and thus represents a therapeutic agent for treatment of viral infection. It is demonstrated in Examples 1 and 2 that poly-U/UC PAMPs with a poly-U core over 8 nucleotides in length can have an innate immunostimulatory effect and can confer anti-viral effect in vitro and in vivo.

This Example describes additional assays to determine the utility and efficacy for various poly-U/UC RNA constructs to induce innate responses in vivo. It was determined from in vivo assays that the poly-U/UC RNA constructs induce innate immune responses through MAVS/RLR-mediated signaling and protect mice from lethal West Nile virus challenge.

Results and Discussion

As described in Examples 1 and 2, a polyU/UC region from the hepatitis C virus (HCV) RNA genome was discovered as a PAMP that specifically engages and triggers RIG-I-dependent signaling of innate antiviral immunity. The present study demonstrates the selective triggering of RIG-I/MAVS signaling using the HCV-derived poly-U/UC PAMP RNA constructs protects mice from virus challenge. Mice injected with the HCV PAMP express various interferon stimulated genes (ISG) in tissues including the liver as compared to mice injected with either PBS alone or the antagonistic X region RNA from the HCV genome (FIGS. 1A and 1B). Specifically, FIG. 9A illustrates an imunohistological stain of liver tissue from wt MAVS mice or mice with a double negative mutant for MAVS. The figure demonstrates the detection of ISG54 expression only in the wt MAVS mice that were administered 200 μg poly-U/UC RNA (as described above in Example 2). FIG. 9B is an immunoblot that demonstrates the expression of ISG54, ISG56, and ISG15 only in liver cells from wt MAVS mice that had been administered the poly-U/UC RNA. Mice injected with the HCV poly-U/UC RNA PAMP further exhibit elevated levels of type I interferon in their serum (FIG. 9C and data not shown). This signaling is strictly dependent on MAVS as mice lacking MAVS express little or no ISG in the liver and only background levels of type I interferon is detectable in the serum.

In view of the above, it was hypothesized that the HCV PAMP RNA and other RLR agonists that can specifically trigger RLR signaling might be useful as adjuvants or antiviral therapies. To test this hypothesis, the effect on administration of HCV PAMP RNA constructs on in vivo viral burden was assayed. SCID/beige-Alb/uPA chimeric mice were transplanted with human primary hepatocytes. After confirming expression of human albumin, mice received 100 mL HCV-positive patient serum, and were administered thereafter at days 11, 13, and 15 post-infection with PBS alone or 150 mg polyU/UC (PAMP) RNA or control xRNA by hydrodynamic IV injections via the tail vein. Mice were bled at 7 days post-infection and at 14 days post-infection to establish viremia levels for qPCR studies to establish pre-treatment viremia and viremia during the course of treatment. FIG. 10 illustrates the log scale difference in HCV viremia levels between days 14 and 7, indicating that administration of the polyU/UC PAMP RNA construct resulted in a significant reduction in viral burden in vivo. A similar assay was performed, but wherein the mice were bled at day 10 post-infection (to establish a pre-treatment viremia baseline) and at days 14 and 15 post-infection (to establish viremia levels during and post treatment). FIGS. 11A and 11B illustrate similar patterns as in FIG. 10, wherein administration of the polyU/UC PAMP RNA construct resulted in significant reduction of viral burden in vivo.

Further investigations were conducted to determine whether administration of the polyU/UC PAMP RNA construct could confer protection in vivo to other viruses. In a first assay, C57Bl6 mice were infected with West Nile virus (WNV), and thereafter at days 1.5, 3, and 5, mice were given 100 mg polyU/UC RNA or control XRNA by IP, and monitored daily for body weight and clinical scores. FIG. 12 is a survivorship plot of the mice that demonstrates that the poly-U/UC PAMP RNA construct, but not the XRNA construct, protected the mice against disease and/or disease severity of WNV infection. In a second assay, wildtype and double negative MAVS mutant mice were challenged with West Nile virus. The mice were provided the HCV polyU/UC PAMP RNA PAMP construct, the antagonistic HCV RNA of equivalent length (XRNA) or PBS alone. The wildtype mice that were provided the HCV PAMP RNA demonstrate reduced virus burden in the spleen and fewer succumb to West Nile virus infection as compared to mice injected with PBS alone or mice injected with XRNA (FIGS. 13A and 13D). Mice that survive the virus challenge also exhibit less severe weight loss and clinical scores when provided the HCV PAMP RNA, suggesting that HCV PAMP RNA has a protective function against WNV challenge (FIGS. 13E and 13F). In contrast, MAVS deficient mice remain highly susceptible to West Nile virus challenge regardless of whether they are provided the HCV PAMP RNA, suggesting that the HCV PAMP RNA provided no protection to the mice. The data thus demonstrates that the HCV PAMP RNA is capable of triggering innate immune response, thereby conferring protection against infections of various viruses. The data also emphasizes the important nature of MAVS in signaling innate antiviral immunity and protection from virus infection.

Numerous studies have shown that MAVS is essential for the control of virus infection and immunity in vivo. In this study, it is demonstrated that the HCV polyU/UC RNA PAMP construct can selectively trigger MAVS-dependent signaling as a RIG-I-specific agonist. Not only did the administration of the polyU/UC PAMP RNA construct increase the average survival rate of mice, it also reduced weight loss and severity of clinical symptoms that is associated with WNV infections as compared to administration of PBS or an antagonist RNA. This data confirms previous suggestions that agents that the polyU/UC PAMP RNA can drive RIG-I/MAVS-dependent signaling and suggest that the constructs are good therapeutic platform for the development of novel antiviral treatments or adjuvants to enhance vaccine immunity.

Methods and Materials

Cell Culture and Viruses

Huh7, HEK293 and the replicon cells Huh7-HCV K2040 and Huh7-HCV A7, which harbor self-replicating subgenomic HCV genotype 1b RNA, were cultured according to standard techniques. To create non-targeting vector control (NTV) and MAVS knockdown cells, Huh7 were transduced with a lentivirus expressing non-specific control shRNA (previously verified not to target any known human or mouse sequences) or a lentivirus expressing shRNA that specifically targets MAVS according to manufacturer's recommendations. Stable cells were selected and propagated in complete media supplemented with hygromycin. Lentivirus stocks were acquired from the Sigma-Aldrich Mission shRNA collection. The shRNA sequences were encoded by the lentivirus (MAVS knockdown). Stocks of Cantell strain Sendai virus were acquired from Charles River Laboratory. Cell culture adapted JFH1 genotype 2A HCV and WNV-Tx were propagated and infectivity measured as described elsewhere (Fredericksen, B. L., et al. "The host response to West Nile Virus infection limits viral spread through the activation of the interferon regulatory factor 3 pathway," *J. Virol.* 78(14): 7737-7747 (2004); Loo, Y. M., et al. "Viral and therapeutic control of IFN-beta promoter stimulator 1 during hepatitis C virus infection," *Proc. Nat'l Acad. Sci. U.S.A.* 103(15): 6001-6006 (2006)).

Plasmids and Transfections

The following plasmids used in this study have been described elsewhere: pEFTak MAVS and C508Y mutant, pcDNA3.1 Myc MAVS, HA-NEMO, reporter plasmids (pIFNb-Luc, PRDii-Luc, F3-Luc, *Renilla*-Luc), IRF3-5D, and pEFTak N-RIG (Foy, E., et al. "Regulation of interferon regulatory factor-3 by the hepatitis C virus serine protease," *Science* 300(5622):1145-1148 (2003); Sumpter, R., Jr., et al. "Regulating intracellular antiviral defense and permissiveness to hepatitis C virus RNA replication through a cellular RNA helicase, RIG-I," *J. Virol.* 79(5):2689-2699 (2005); Loo, Y. M., et al. 2006). DNA transfections were performed using FuGene 6 (Roche) or Lipofectamine 2000 (Invitrogen) as recommended by the manufacturer. Promoter luciferase reporter assays were conducted as described (Foy, Li et al. 2003). HCV XRNA and polyU/UC PAMP RNA ("pU/UC C67U" in Table 1) were generated using the MegaScript in vitro transcription kit (Ambion) as described below, above in Examples 1 and 2, and elsewhere (Saito, T., et al., "Innate immunity induced by composition-dependent RIG-I recognition of hepatitis C virus RNA," *Nature* 454(7203): 523-527 (2008)).

RNA Methods

All in vitro transcribed RNAs contain a 5'-triphosphate (5'-ppp) and three guanine nucleotides at the 5' end to enhance T7 polymerase transcription. HCV X-region 5'-ppp RNA was synthesized from a T7 promoter-linked PCR product generated from the pX-region c4 plasmid using the primers X-regionF and X-regionR, described above in Example 1 and set forth herein as SEQ ID NOS:80 and 81, respectively. The amplified PCR product was purified by agarose gel extraction using the QIAquick kit (Qiagen) as per the manufacturer's protocol. Full-length HCV RNA was produced from the pJFH-1 plasmid (genotype 2a) as previously described (Saito et al., 2008). All other 5'-ppp RNA products were generated using synthetic DNA oligonucleotide templates (Integrated DNA Technologies) and the T7 RNA polymerase (as described by Saito et al., 2008) using the T7 MEGAshortscript kit (Ambion) as per the manufacturer's instructions. Following in vitro transcription, DNA templates were removed with DNAse treatment and unincorporated nucleotides were removed from the reaction using Illustra MicroSpin G-25 columns (gel filtration column chromatography, GE Healthcare). RNA was then precipitated using ethanol and ammonium acetate as described by the manufacturer, then resuspended in nuclease-free water. RNA concentration was determined by absorbance using a Nanodrop spectrophotometer. RNA quality was assessed on denaturing 8M urea polyacrylamide gels for short RNA transcripts (50-150 bp). Full-length HCV RNA quality was assessed on a denaturing formaldehyde-agarose gel.

Luciferase Reporter Assay

Huh7 or Huh7.5 cells were plated on 10 cm dishes, and 24 hours later cells were transfected with 5.76 µg pIFN-β-luc (firefly luciferase) and 0.24 µg pCMV-*Renilla*-luc (*Renilla luciferase*) plasmids using the FuGENE 6 transfection reagent and protocol (Roche). Transfected Huh7 or Huh7.5 cells were incubated at 37° C. for 18 hours, then split into 48-well plates and incubated for an additional 12 hours prior to RNA transfection. RNA transfection was conducted in a 48-well plate format using the TransIT-mRNA Transfection kit (Mirus) as per the manufacturer's instructions. RNA transfection was conducted using either equal numbers of moles of each RNA or 350 ng RNA, depending on the experiment. Following RNA transfection, cells were incubated an additional 18 hours and luciferase activity was measured using the Dual-Luciferase reporter assay system (Promega). All conditions and experiments were conducted in triplicate.

Antibodies

The following antibodies were used in this study: anti-Flag M2 (Sigma-Aldrich), anti-Myc 9E10 (AbCam), anti-Myc (AbCam), anti-Cardif (for MAVS; Axxora), anti-ISG54 and ISG56 (G. Sen), anti-IRF-3 (M. David), anti-IRF-3 phospho (Cell Signaling), anti-ISG15 (A. Haas), anti-HA (Sigma), anti-IKKe (Santa Cruz), anti-TANK (Santa Cruz), anti-TBK1 (Santa Cruz), anti-TRAF6 (Sigma), anti-NEMO (Sigma), anti-COX-IV (Molecular Probes), anti-actin (Sigma), anti-tubulin (Sigma), and polyclonal human anti-HCV (hyperimmune sera from an HCV-infected patient). Mitotracker and DAPI were acquired from Molecular probes.

MAVS Knockout Mice

MAVS knockout mice in the C57Bl/6 background were created using conventional methods at inGenious Targeting Laboratory, Inc. using C57Bl/6 ES cells by replacing exons 2-3 of MAVS (containing the ATG start codon) with a neomycin cassette. Deletion of exons 2-3 was verified by Southern blot (not shown). Northern blot and qPCR analyses confirm that cells from knockout mice do not express MAVS mRNA. Mice are genotyped using primers 5'-ATGGGATCGGCCATTGAACAAGATC-3' (set forth as SEQ ID NO:82), 5'-CACCCAGCCACCAGAGTC-CCCAG-3' (set forth as SEQ ID NO:83), and 5'-CCCTGC-CTCCTGTCTAAGGAAGG-3'(set forth as SEQ ID NO:84) for detection of both the wildtype and mutant alleles.

Poly-U/UC PAMP RNA Transfection and Virus Challenge In Vivo

C57Bl/6 mice of matching age and gender were used as wildtype controls in all experiments. PBS, HCV XRNA or HCV polyU/UC PAMP RNA mixed in lipid-based In Vivo transfection reagent (Altogen Biosystems) was injected by the intraperitoneal route as recommended by the manufacturer. Mice were euthanized at indicated time points to collect blood and tissues. For liver immunohistochemistry, perfused livers were fixed in 4% paraformaldehyde and imbedded in paraffin. 5 nm sections were affixed to charged slides, and processed for immunohistochemistry at the UW Core facility. Serum cytokine levels were measured using the Verikine Interferon-β ELISA kit (PBL). For infection experiments, mice were injected in one footpad with $1 \times 10^5$ PFU WNV-TX. Mice were provided 200 µg of either HCV XRNA or polyU/UC PAMP RNA by IP at days 1, 3, 5, and 7 post-infection. Mice were weighed daily and monitored for changes in clinical scores as described previously (Suthar, M. S., et al., "MAVS is essential for the control of West Nile virus infection and immunity," *PLoS Pathogens* 6(2):e1000757 (2010)). All mouse breeding and experiments were conducted in specific pathogens-free facilities in strict accordance to protocols approved by the University of Washington IACUC.

Immunoprecipitations

HEK293 cells were co-transfected with a Flag-tagged bait construct and either a Myc- or HA-tagged target construct using FuGene 6 (Roche). Cell pellets were collected 24 hrs after transfection and the immunoprecipitations performed using Flag antibody-coated agarose beads (Sigma-Aldrich) in RIPA buffer (50 mM Tris-HCl pH 7.4, 100 mM NaCl, 1% Triton-x100, 0.5% sodium deoxycholate). Precipitates were analyzed by SDS-PAGE and immunoblotting using standard techniques.

RNA Analysis

Total RNA was extracted from cultured cells using the RNeasy kit (Qiagen). HCV copy number was measured from triplicate reactions by real time-quantitative PCR (qPCR) as previously described using an Applied Biosystems 7300.

Example 4

Summary

As described above, the HCV-derived poly-U/UC PAMP RNA can drive RIG-I/MAVS-dependent signaling and mediate an innate immune response. Furthermore, it was demonstrated above that administration of the HCV-derived poly-U/UC PAMP RNA construct conferred protection against different viral infections in mice. The present Example addresses the utility of using a HCV-derived poly-U/UC PAMP RNA, as described above, as an adjuvant to enhance the efficacy vaccine components in protecting against viral disease.

Introduction

West Nile virus (WNV) is a neurotropic flavivirus that constitutes the leading cause of mosquito-borne and epidemic encephalitis in humans in the United States. WNV is a member of the family Flaviviridae and carries a single-stranded positive-sense RNA genome of approximately 11 kb in length consisting of a single open reading frame that is translated as a polyprotein to generate ten viral proteins.

Lineage 1 WNV strains represent emerging viruses that associate with outbreaks of encephalitis and meningitis in Europe, the Middle East, and now in North America, whereas lineage 2 strains are typically nonpathogenic, non-emergent and geographically confined to the African sub-continent and Madagascar. More recently, lineage 1 WNV associated infections have shifted from causing disease in young children, elderly, and the immunocompromised to afflicting healthy young adults, indicating that virulence occurs independently of immune senescence or immune deficiencies associated with aging. Pathogenic lineage 2 WNV variants have recently emerged in Europe, causing significant WNV-induced disease in humans. The increase in virulence of lineage 1 and 2 strains, coupled with a lack of a vaccine or therapeutic agents continues to present WNV as a significant public health threat.

The host innate immune response is the first line of defense during virus infection and is responsible for deterring virus replication and spread within the host. Lineage 1 WNV-TX, but not lineage 2 WNV-MAD, has been shown to inhibit type I IFN-induced phosphorylation of STAT1 and STAT2 by blocking the activity of the IFN receptor-associated kinase, Tyk2. It was found that WNV-TX also blocks an IKKε-dependent phosphorylation event on STAT1, resulting in a temporal regulation of STAT1 phosphorylation and subsequent expression of interferon-stimulated genes that are essential for controlling WNV infection. However, studies to identify specific viral determinants that regulate WNV inhibition of IFN-mediated signaling have been hindered by the lack of appropriate reagents.

Results and Discussion

As described previously in Suthar, M. S., et al., "Infectious Clones of Novel Lineage 1 and Lineage 2 West Nile Virus Strains WNV-TX02 and MNV-Madagascar," *J. Virol.* 86(14):7704-7709 (2012), incorporated herein by reference in its entirety, to facilitate viral genetic studies of WNV/host interactions that control infection and immunity, a novel infectious clone (i.c.) of WNV-TX (strain TX 2002-HC) and a clone of WNV-MAD (strain Madagascar-AgMg798) were generated. The design of each infectious clone is based on a two-plasmid reverse genetics system. In this system, the structural and nonstructural genes are broken into two plasmids (pAB and pCG, respectively). This system allows for overcoming limitations imposed by genetic instability during plasmid propagation in bacterial hosts, problems due to difficult low-yield plasmid preparations, as well as limitations due to a lack of restriction sites for cDNA insertion in single-plasmid cloning schemes. To generate the infectious clones, the coding sequences of NY99 strain 382-99 were replaced with either WNV-TX or WNV-MAD in the respective plasmids. The sequence of the viral RNA 5' UTR is conserved among WNV-NY99, WNV-TX, and WNV-MAD. The 3' UTR sequence of the viral RNA is conserved between WNV-NY99 and WNV-TX, but not WNV-MAD (73.4% sequence similarity). For generating the WNV-TX infectious clone, three amino acid coding changes within the sequence of WNV-NY99 (strain 382-99) were replaced with WNV-TX. The WNV-MAD infectious clone was synthesized (Genscript, Piscataway, N.J.) with nucleotides (nt) 1-2500 (encoding the structural genes) inserted in a pUC19 vector (Genscript) and nt 2494-10396 (with the 3'UTR (nt 10397-11031) from WNV-TX) in a pCCI vector (Genscript). To allow for full-length clone assembly, a unique NgoMIV restriction site was engineered (nt A2496C, A2498G) that did not alter the NS1 amino acid coding sequence. Infectious WNV-TX and WNV-MAD RNA was successfully prepared from their respective two-plasmid infectious clones, introduced in BHK-21 cells by electroporation, and viral supernatants recovered and aliquoted as the primary working stocks for phenotypic analysis. The two novel strains were characterized to confirm that they retained characteristics of their parental strains. The resulting WNV-TX and WNV-MAD infectious clones, which differ in their abilities to inhibit type I IFN signaling, provide a platform for identification of novel viral determinants in regulating type I IFN signaling and responses.

The novel avirulent WNV-MAD infectious clone can serve as a live-attenuated vaccine strain and permit the present study to address the capacity of the poly-U/UC PAMP RNA constructs to enhance host responses against infections pathogens when administered in association with vaccine components.

FIG. 14A illustrates the vaccination schedule performed in the present study. At 21 days prior to C57Bl6 mice (5-6 weeks old) were vaccinated with 100 mg polyU/UC PAMP RNA alone, 0.25 mg UV-inactivated WNV (MAD clone) +PBS, or 0.25 mg UV-inactivated WNV mixed with 100 mg polyU/UC PAMP RNA or xRNA control. At "Day 0" the mice were challenged with 1000 pfu WNV (TX-02 clone) administered via subcutaneous injection of the left footpad. Mice were monitored daily for body weight and clinical scores. FIG. 14B illustrates the survival patterns for the groups of mice after challenge with the pathogenic WNZ (Tx) strain. Differences shown between WNZ (MAD clone) vaccine +poly-U/UC PAMP RNA and other treatment groups were significant (P<0.03), with all individuals surviving to the end of the observation period. This demonstrates that poly-U/UC RNA is an effective vaccine adjuvant for enhancement of protection by virus vaccines.

Methods and Materials

Preparation attenuated and pathogenic virus strains for the challenge studies are described in Suthar, M. S., et al., "Infectious Clones of Novel Lineage 1 and Lineage 2 West Nile Virus Strains WNV-TX02 and MNV-Madagascar," *J. Virol.* 86(14):7704-7709 (2012), incorporated herein by reference in its entirety.

UV-inactivated stocks of WNV-MAD were prepared by irradiating the virus using a Spectrolinker XL-1000 at 120 mJ/cm$^2$ for 30 minutes. Infectivity of virus stocks was verified by plaque assay on VERO cells, and protein concentration of the stocks quantified by BCA assay (Thermo Scientific Pierce) using a BSA standard according to manufacturer's instructions.

In Vivo Vaccine-Challenge Studies 5-6 week old C57Bl/6 mice were vaccinated subcutaneously with 100 ug polyU/UC RNA alone, 0.25 ug UV-inactivated WNV-MAD+PBS or 0.25 ug UV-inactivated WNV-MAD mixed with 100 ug of polyU/UC RNA or xRNA control. 21 days after vaccination, mice were challenged with 1000 pfu WNV (Tx-02) administered via subcutaneous injection of the left footpad. Mice were monitored daily for body weight and clinical scores. Mice that exhibit 20% or greater weight loss or clinical symptoms greater than 5 (moribund) were euthanized according to UW IACUC approved protocols. Clinical symptoms were determined according to the following scoring system:

0: Healthy mouse
1: Ruffled fur, lethargy, hunched posture, no paresis
2: Very mild to mild paresis affecting one or both hind limbs
3: Frank paresis involving one hind limb or mild paresis in both hind limbs, conjunctivitis
4: Severe paresis involving both hind limbs but mouse retains feeling and is possibly limbic
5: True paresis
6: Moribund
7: Euthanized mouse

Example 5

Summary

This Example describes characterization of Hepatitis C 3' poly-U/UC regions from isolates obtained from human subjects. The data confirms the variability of the length of poly-U core among wild isolates and indicates that short poly-U core lengths are likely to contribute to RIG-I signaling.

Results and Discussion

Hepatitis C RNA was sequenced from biological samples obtained from human patients. The 3' poly-U/UC region for the isolates are presented below in Table 3. Several isolates contained poly-U core sequences under 20 nucleotides in length, indicating that such PAMPs exist in nature. Additional studies can be performed on such PAMPs to determine their capacities to bind RIG-I and stimulate subsequent innate immune responses through RIG-I/MAVS-dependent signaling. PAMP sequences with various length and short U-core regions have the ability to "tune" the innate immune response to specific applications. For example, a robust response might be required to induce protective immunity against a specific pathogen while a reduced response might be required to trigger lower level innate immunity against specific microbial agents where microbial-induced inflammation has been triggered during infection.

TABLE 3

Sequence of 3' poly-U/UC regions for HCV isolates from human subjects.

| Plasmid # | Founder | Genotype | 5' arm | U-Core | 3' arm | SEQ ID NO: |
|---|---|---|---|---|---|---|
| PAMP | HCV Con1 | 1b | GGCCAUCCUG(U7)CCC(U11)C | U34 | CUCC(U9)CCUC(U7)CCUUUUCUUUCCUUU | 85 |
| 1716 | 9055TF.UC1 | 3a | CCAUUUUUC | U13 | GUUUG(U16)CUUUCCUUCUUUCCUGACUUUUAAUUUUCCUUCUUA | 86 |
| 1717 | 9055TF.UC2 | 3a | CCAUUUUUC | U49 | GUUUG(U17)CUUUCCUUCUUUCCUGACUUUUAAUUUUCCUUCUUA | 87 |
| 1713 | 10021TF.UC1 | 1a | GGCCAUUUCCUG | U33 | ACCCUUUUUUCUC(U12)CCUUCUUCUUUAAU | 88 |
| 1714 | 10021TF.UC2 | 1a | GGCCAUUUCCUG | U18 | ACCCUUUUUUCUC(U17)CCUUCUUCUUUAAU | 89 |
| 1720 | 10025TF.UC1 | 1a | GGCCAUUUUCUG | U14 | AUUUUCUUUAAU | 90 |
| 1721 | 10025TF.UC2 | 1a | GGCCAUUUUC(U10)CUC | U18 | AUUUUCUUUAAU | 91 |
| 1722 | 10025TF.UC3 | 1a | GGCCAUUUUCUG | U20 | CC(U12)CCUC(U20)AUUUUCUUUAAU | 92 |
| 1723 | 10025TF.UC4 | 1a | GGCCAUUUUCUG(U12)C | U17 | CCUUUUUUUUUCUC(U14)AUUUUCUUUAAU | 93 |
| 1715 | 10051TF.UC1 | 1b | GGCCAUCCUG | U24 | G(U17)CUUUUUCC(U13)AUUUUCUUCUUU | 94 |
| 1725 | 105431TF.UC1 | 4a | GGUCCUAAG | U13 | CUUCCUUCCUUCUUUCCUUUUCUAAUUUUCCUUCUUU | 95 |
| 1726 | 105431TF2.UC1 | 4a | GGUCCUAAGUUG | U15 | CCUUCCUUCUUUCCCUUUUCUAAUUUUCCUUCUUU | 96 |
| 1727 | 105431TF2.UC2 | 4a | GGUCCUAAGUUG | U23 | CCUUUCCUUCCUUCUUUCCUUUUCUAAUUUUCCUUCUUU | 97 |
| 1718 | 110069TF1.UC1 | 1a | GGCCAUUUCUG | U41 | GUUUCCUUCUUUUUCCUUUUC(U11)CUCCCUUUAAU | 98 |
| 1719 | 11069TF.1UC2 | 1a | GGCCAUUUCUG | U14 | GUUUCCUUCUUUUUCCUUUUC(U13)CUCCCUUUAAU | 99 |

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of inducing RLR signaling in a subject, comprising administering to the subject an effective amount of a pharmaceutical composition comprising a synthetic nucleic acid pathogen-associated molecular pattern (PAMP), wherein the synthetic PAMP comprises:
   a 5'-arm region comprising a terminal triphosphate;
   a poly-uracil core comprising at least 8 contiguous uracil residues; and
   a 3'-arm region comprising at least 8 nucleic acid residues, wherein the 5'-most nucleic acid residue of the 3'-arm region is not a uracil and wherein the 3'-arm region is at least 80% uracil residues.

2. The method of claim 1, further comprising administering a viral antigen, a bacterial antigen, a protozoal antigen, a fungal antigen, and/or a helminth antigen, or an attenuated, inactivated, or killed virus, bacterium, protozoan, fungus, and/or helminth.

3. The method of claim 2, wherein the virus is a member of, or is derived from, the Flaviviridae, Paramyxoviridae, Hepaciviridae, Orthomyxoviridae, Bunyaviridae, Arenaviridae, Reoviridae, Retroviridae, Enteroviruses, Picornaviridae, Coronaviridae, or Noroviridae families, or the viral antigen is derived from a virus of the Flaviviridae, Paramyxoviridae, Hepaciviridae, Orthomyxoviridae, Bunyaviridae, Arenaviridae, Reoviridae, Retroviridae, Enteroviruses, Picornaviridae, Coronaviridae, or Noroviridae families.

4. The method of claim 3, wherein the virus is a West Nile virus, dengue virus, Japanese encephalitis virus, vesicular stomatitis virus, hepatitis C virus, respiratory syncytial virus, yellow fever virus, influenza A virus, Lassa fever virus, Hantavirus, lymphocytic choriomenengitis virus, polio virus, parainfluenza virus, rotavirus, human immunodeficiency virus (HIV), human T-lymphotropic virus (HTLV), enterovirus 21 and strains thereof, severe acute respiratory syndrome (SARS) virus, Middle East respiratory syndrome (MERS) virus, corona virus, or norovirus, or is derived therefrom.

5. The method of claim 4, wherein the virus is an attenuated West Nile virus.

6. The method of claim 5, wherein the attenuated West Nile virus is a recombinant clone derived from a lineage 2 Madagascar strain of West Nile virus.

7. The method of claim 1, wherein the administration step does not induce septic shock in the subject.

8. The method of claim 1, wherein induction of RLR signaling is manifested by an increase in IFN-β levels, an increase in ISG54 levels, or an increase in IRF3 phosphorylation.

9. The method of claim 8, wherein the RLR is RIG-I.

10. The method of claim 1, wherein the condition is a viral, bacterial, protozoal, fungal, and/or helminth infection in the subject.

11. The method of claim 1, wherein the poly-uracil core consists of between 8 and 30 uracil residues.

12. The method of claim 1, wherein the 5'-most nucleic acid residue of the 3'-arm region is a cytosine residue or a guanine residue.

13. The method of claim 1, wherein the 3'-arm region is at least 90% uracil residues.

14. The method of claim 1, wherein the 3'-arm region comprises at least 7 contiguous uracil residues.

15. The method of claim 1, wherein the 5'-arm region further comprises one or more nucleic acid residues disposed between the terminal triphosphate and the poly-uracil core.

16. The method of claim 15, wherein the terminal triphosphate, the one or more nucleic acid residues of the 5'-arm region, and the poly-uracil core do not naturally occur together in a Hepatitis C virus.

17. The method of claim 1, wherein the synthetic PAMP is capable of inducing retinoic acid-inducible gene I (RIG-I)-like receptor (RLR) activation.

18. The method of claim 17, wherein the RLR is RIG-I.

19. The method of claim 1, further comprising administering an anti-viral therapeutic, an anti-bacterial therapeutic, an anti-protozoal therapeutic, an anti-fungal therapeutic, an anti-helminth therapeutic, and/or an adjuvant.

20. The method of claim 1, wherein the 5'-arm region consists of the terminal triphosphate, and wherein the terminal triphosphate is linked directly to the 5'-end of the poly-uracil core.

* * * * *

SEQUENCE LISTING

```
<160> NUMBER OF SEQ ID NOS: 99

<210> SEQ ID NO 1
<211> LENGTH: 105
<212> TYPE: RNA
<213> ORGANISM: Artificial Sequence
<220> FEATURE:
```

<223> OTHER INFORMATION: Synthetic RNA

<400> SEQUENCE: 1

| ggccauccug uuuuuucccc uuuuuuuuuu ucuuuuuuuu uuuuuuuuuu uuuuuuuuuu | 60 |
| uuuuuucucc uuuuuuuuuc cucuuuuuuu ccuuucuuu ccuuu | 105 |

<210> SEQ ID NO 2
<211> LENGTH: 107
<212> TYPE: RNA
<213> ORGANISM: Artificial Sequence
<220> FEATURE:
<223> OTHER INFORMATION: Synthetic RNA

<400> SEQUENCE: 2

| acuguuccuu uuuuuuuuuu uuuuuuuuuu uuuuuuuuuu uuuuuuuuuu ucuuuuuuuu | 60 |
| uuuuuucccu cuuucuuccc uucucaucuu auucuacuuu cuuucuu | 107 |

<210> SEQ ID NO 3
<211> LENGTH: 131
<212> TYPE: RNA
<213> ORGANISM: Artificial Sequence
<220> FEATURE:
<223> OTHER INFORMATION: Synthetic RNA

<400> SEQUENCE: 3

| ggccauccug uuuuuucccc uuuuuuuuuu ucuuuuuuuu uuuuuuuuuu uuuuuuuuuu | 60 |
| uuuuuucucc uuuuuuuuuc cucuuuuuuu ccuuucuuu ccuuucccc cccccccccc | 120 |
| cccccccccc c | 131 |

<210> SEQ ID NO 4
<211> LENGTH: 105
<212> TYPE: RNA
<213> ORGANISM: Artificial Sequence
<220> FEATURE:
<223> OTHER INFORMATION: Synthetic RNA

<400> SEQUENCE: 4

| ggccauccug uuuuuucccc uuuuuuuuuu ucuuuuuuuu uuuuuuuuuu uuuuuuuuuu | 60 |
| uuuuuucucc uuuuuuuuuc cccccccccc cccccccccc ccccc | 105 |

<210> SEQ ID NO 5
<211> LENGTH: 105
<212> TYPE: RNA
<213> ORGANISM: Artificial Sequence
<220> FEATURE:
<223> OTHER INFORMATION: Synthetic RNA

<400> SEQUENCE: 5

| ggccauccug uuuuuucccc uuuuuuuuuu ucuuuuuuuu uuuuuuuuuu uuuuuuuuuu | 60 |
| uuuuuuuucc uuuuuuuuuc cucuuuuuuu ccuuucuuu ccuuu | 105 |

<210> SEQ ID NO 6
<211> LENGTH: 105
<212> TYPE: RNA
<213> ORGANISM: Artificial Sequence
<220> FEATURE:
<223> OTHER INFORMATION: Synthetic RNA

<400> SEQUENCE: 6

| uuuuuuuuuu uuuuuuuuuu uuuuuuuuuu uuuuuuuuuu uuuuuuuuuu uuuuuuuuuu | 60 |
| uuuuuuuuuu uuuuuuuuuu uuuuuuuuuu uuuuuuuuuu uuuuu | 105 |

<210> SEQ ID NO 7
<211> LENGTH: 71
<212> TYPE: RNA
<213> ORGANISM: Artificial Sequence
<220> FEATURE:
<223> OTHER INFORMATION: Synthetic RNA

<400> SEQUENCE: 7
ggccauccug uuuuuuccc uuuuuuuuuu uccuccuuuu uuuuuccucu uuuuuuccuu    60
uucuuuccuu u                                                       71

<210> SEQ ID NO 8
<211> LENGTH: 105
<212> TYPE: RNA
<213> ORGANISM: Artificial Sequence
<220> FEATURE:
<223> OTHER INFORMATION: Synthetic RNA

<400> SEQUENCE: 8
ggccauccug uuuuuuccc uuuuuuuuuu ucuuuuuuuu cuccuuuuuu uuuccucuuu    60
uuuuccuuuu cuuccuuuc cccccccccc cccccccccc ccccc                   105

<210> SEQ ID NO 9
<211> LENGTH: 105
<212> TYPE: RNA
<213> ORGANISM: Artificial Sequence
<220> FEATURE:
<223> OTHER INFORMATION: Synthetic RNA

<400> SEQUENCE: 9
ggccauccug uuuuuuccc uuuuuuuuuu ucuuuuuuuu uuuuuuuuuc uccuuuuuuu    60
uuccucuuuu uuuccuuuuc uuuccuuucc cccccccccc ccccc                  105

<210> SEQ ID NO 10
<211> LENGTH: 62
<212> TYPE: RNA
<213> ORGANISM: Artificial Sequence
<220> FEATURE:
<223> OTHER INFORMATION: Synthetic RNA

<400> SEQUENCE: 10
ggccauccug uuuuuuuuuu uuuuuuuuuu uuuuuuuuuu uuuucuccuu uuuuuuuccu    60
cu                                                                 62

<210> SEQ ID NO 11
<211> LENGTH: 62
<212> TYPE: RNA
<213> ORGANISM: Artificial Sequence
<220> FEATURE:
<223> OTHER INFORMATION: Synthetic RNA

<400> SEQUENCE: 11
cccccccccc uuuuuuuuuu uuuuuuuuuu uuuuuuuuuu uuuucuccuu uuuuuuuccu    60
cu                                                                 62

<210> SEQ ID NO 12
<211> LENGTH: 62
<212> TYPE: RNA
<213> ORGANISM: Artificial Sequence
<220> FEATURE:
<223> OTHER INFORMATION: Synthetic RNA -continued

```
<400> SEQUENCE: 12
ggccauccug uuuuuuuuuu uuuuuuuuuu uuuuuuuuuu uuuucccccc cccccccccc    60
cc                                                                   62

<210> SEQ ID NO 13
<211> LENGTH: 62
<212> TYPE: RNA
<213> ORGANISM: Artificial Sequence
<220> FEATURE:
<223> OTHER INFORMATION: Synthetic RNA

<400> SEQUENCE: 13
uuuuuuuuuu uuuuuuuuuu uuuuuuuuuu uuuuuuuuuu uuuuuuuuuu uuuuuuuuuu    60
uu                                                                   62

<210> SEQ ID NO 14
<211> LENGTH: 62
<212> TYPE: RNA
<213> ORGANISM: Artificial Sequence
<220> FEATURE:
<223> OTHER INFORMATION: Synthetic RNA

<400> SEQUENCE: 14
uuuuuuuuuu uuuuuuuuuu uuuuuuuuuu uuuuuuuuuu uuuucuuuuu uuuuuuuuuu    60
uu                                                                   62

<210> SEQ ID NO 15
<211> LENGTH: 62
<212> TYPE: RNA
<213> ORGANISM: Artificial Sequence
<220> FEATURE:
<223> OTHER INFORMATION: Synthetic RNA

<400> SEQUENCE: 15
uuccuuccuu uuuuuuuuuu uuuuuuuuuu uuuuuuuuuu uuuucuccuu uuuuuuuccu    60
cu                                                                   62

<210> SEQ ID NO 16
<211> LENGTH: 62
<212> TYPE: RNA
<213> ORGANISM: Artificial Sequence
<220> FEATURE:
<223> OTHER INFORMATION: Synthetic RNA

<400> SEQUENCE: 16
uuuuuuuuug uuuuuuuuuu uuuuuuuuuu uuuuuuuuuu uuuucuccuu uuuuuuuccu    60
cu                                                                   62

<210> SEQ ID NO 17
<211> LENGTH: 62
<212> TYPE: RNA
<213> ORGANISM: Artificial Sequence
<220> FEATURE:
<223> OTHER INFORMATION: Synthetic RNA

<400> SEQUENCE: 17
uuuuuuuuug uuuuuuuuuu uuuuuuuuuu uuuuuuuuuu uuuucuccuu uuuuuuuccu    60
cu                                                                   62

<210> SEQ ID NO 18
<211> LENGTH: 62
```

<212> TYPE: RNA
<213> ORGANISM: Artificial Sequence
<220> FEATURE:
<223> OTHER INFORMATION: Synthetic RNA

<400> SEQUENCE: 18
gguuuuccuu uuuuuuuuuu uuuuuuuuuu uuuuuuuuuu uuuucuuuuu uuuuuuuuuu    60
uu                                                                   62

<210> SEQ ID NO 19
<211> LENGTH: 62
<212> TYPE: RNA
<213> ORGANISM: Artificial Sequence
<220> FEATURE:
<223> OTHER INFORMATION: Synthetic RNA

<400> SEQUENCE: 19
ggccauccug uuuuuuuuuu cuuuuuuuuu ucuuuuuuuu uucucuccuu uuuuuuuccu    60
cu                                                                   62

<210> SEQ ID NO 20
<211> LENGTH: 62
<212> TYPE: RNA
<213> ORGANISM: Artificial Sequence
<220> FEATURE:
<223> OTHER INFORMATION: Synthetic RNA

<400> SEQUENCE: 20
ggccauccug uuuuuuuuuu uuuucuuuu uuuuuuuuuu ucuucuccuu uuuuuuuccu    60
cu                                                                   62

<210> SEQ ID NO 21
<211> LENGTH: 62
<212> TYPE: RNA
<213> ORGANISM: Artificial Sequence
<220> FEATURE:
<223> OTHER INFORMATION: Synthetic RNA

<400> SEQUENCE: 21
ggccauccug uuuuuuuuuu cccuuuuuuu uuuccccuuuu uuuucuccuu uuuuuuuccu    60
cu                                                                   62

<210> SEQ ID NO 22
<211> LENGTH: 62
<212> TYPE: RNA
<213> ORGANISM: Artificial Sequence
<220> FEATURE:
<223> OTHER INFORMATION: Synthetic RNA

<400> SEQUENCE: 22
ggccauccug uuuuuuuuuu uuuuuuuucc cccuuuuuuu uuuucuccuu uuuuuuuccu    60
cu                                                                   62

<210> SEQ ID NO 23
<211> LENGTH: 98
<212> TYPE: RNA
<213> ORGANISM: Artificial Sequence
<220> FEATURE:
<223> OTHER INFORMATION: Synthetic RNA

<400> SEQUENCE: 23
gguggcucca ucuuagcccu agucacggcu agcugugaaa gguccgugag ccgcuugacu    60

```
gcagagagug cugauacugg ccucucugca gaucaagu                                  98

<210> SEQ ID NO 24
<211> LENGTH: 133
<212> TYPE: RNA
<213> ORGANISM: Artificial Sequence
<220> FEATURE:
<223> OTHER INFORMATION: Synthetic RNA

<400> SEQUENCE: 24
ggguggcucc aucuuagccc uagucacggc uagcugugaa agguccguga gcuuuuuuuu          60
uuuuuuuuuu uuuuuuuuuu uuuuuucgcu ugacugcaga gagugcugau acuggccucu         120
cugcagauca agu                                                            133

<210> SEQ ID NO 25
<211> LENGTH: 105
<212> TYPE: RNA
<213> ORGANISM: Artificial Sequence
<220> FEATURE:
<223> OTHER INFORMATION: Synthetic RNA

<400> SEQUENCE: 25
ggccauccug uuuuuucccc uuuuuuuuuu ucuuuuuuuu uuuuuuuuuu uuuuuuuuuu          60 uuuuucucc uuuuuuuuuc cucuuuuuuu ccuuucuuu ccuuu                           105

<210> SEQ ID NO 26
<211> LENGTH: 35
<212> TYPE: RNA
<213> ORGANISM: Artificial Sequence
<220> FEATURE:
<223> OTHER INFORMATION: Synthetic RNA

<400> SEQUENCE: 26
ggccauucuu uuuuuuuuuu uuucuuucu ucuuu                                      35

<210> SEQ ID NO 27
<211> LENGTH: 28
<212> TYPE: RNA
<213> ORGANISM: Artificial Sequence
<220> FEATURE:
<223> OTHER INFORMATION: Synthetic RNA

<400> SEQUENCE: 27
ggccguccug uuuuuuuuuu uuuuuuuu                                             28

<210> SEQ ID NO 28
<211> LENGTH: 116
<212> TYPE: RNA
<213> ORGANISM: Artificial Sequence
<220> FEATURE:
<223> OTHER INFORMATION: Synthetic RNA

<400> SEQUENCE: 28
ggccauuccc uuuuuuuuuu uuuuuuuuuu uuuuuuuuuu uuuuuuuuuu uuuuuuuuuu          60
uuuuuuuuuu uuuuuuuuuu uuuuuuuuuu ucucuucuuu ucuuuauucc uucuuu            116

<210> SEQ ID NO 29
<211> LENGTH: 101
<212> TYPE: RNA
<213> ORGANISM: Artificial Sequence
<220> FEATURE:
<223> OTHER INFORMATION: Synthetic RNA

<400> SEQUENCE: 29
```

```
ggccguuccu uuuuuuuuuu uuuuuuuuuu uuuuuuuuuu uuuuuuuuuu uuuuuuuuuu    60
uuuuuuuuuu uuucuuuucc ccuuuuuuau uuuucuuucu u                        101
```

<210> SEQ ID NO 30
<211> LENGTH: 105
<212> TYPE: RNA
<213> ORGANISM: Artificial Sequence
<220> FEATURE:
<223> OTHER INFORMATION: Synthetic RNA

<400> SEQUENCE: 30

```
ggccauccug uuuuuuuguu uuucuuuuu uuuuuuuuuu uuuuuuuuuu uuuuuuuuuu     60
uuuuuuuucu uuuuuuccu uuuuuuuauu uuauuucuu uuggu                      105
```

<210> SEQ ID NO 31
<211> LENGTH: 131
<212> TYPE: RNA
<213> ORGANISM: Artificial Sequence
<220> FEATURE:
<223> OTHER INFORMATION: Synthetic RNA

<400> SEQUENCE: 31

```
ggccauccccc cuuuuuuuuu uuuuuuuuuu uuuuuuuuuu uuuuuuuuuu uuuuuuuuuu   60
uuuuuuuuuu uuuuuuuuuu uuuuuuuuuu uuuuuuuuuu uuuuuuuccu cuuuuuuucc    120
uuuucuucuu u                                                         131
```

<210> SEQ ID NO 32
<211> LENGTH: 116
<212> TYPE: RNA
<213> ORGANISM: Artificial Sequence
<220> FEATURE:
<223> OTHER INFORMATION: Synthetic RNA

<400> SEQUENCE: 32

```
ggccguucug uuuuuuuuuu uuuuuuuuuu uuuuuuuuuu uuuuuuuuuu uuuuuuuuuu    60
uuuuuuuuuu uuuuuuuuuu uuuuuuuuuu uuuuccuuu uuuuuauucc ucuucu         116
```

<210> SEQ ID NO 33
<211> LENGTH: 123
<212> TYPE: RNA
<213> ORGANISM: Artificial Sequence
<220> FEATURE:
<223> OTHER INFORMATION: Synthetic RNA

<400> SEQUENCE: 33

```
ggccauccccc uuuguuuuu uuuuuuuuuu uuuuuuuuuu uuuuuuuuuu uuuuuuuuuu    60
uuuuuuuuuu uuuuuuuuuu uuuuuuuuuu uuuuuuuuuu uuuuuuuuau uucuccuucu    120
uuu                                                                  123
```

<210> SEQ ID NO 34
<211> LENGTH: 87
<212> TYPE: RNA
<213> ORGANISM: Artificial Sequence
<220> FEATURE:
<223> OTHER INFORMATION: Synthetic RNA

<400> SEQUENCE: 34

```
ggccauuccu uuuuuuuuuu uuuuuuuuuu uuucuuuuu uuuccuuuu uuuuuuuuuu      60 uuuuuuuuuu ccuuuucuuu cuucuuu                                        87
```

<210> SEQ ID NO 35
<211> LENGTH: 87
<212> TYPE: RNA
<213> ORGANISM: Artificial Sequence
<220> FEATURE:
<223> OTHER INFORMATION: Synthetic RNA

<400> SEQUENCE: 35

```
ggccauuccu uuuuuuuuuu uuuuuuuuuu uuucuuuuu uuuccuuuu uuuuuuuuuu      60 uuuuuuuuuu ccuuuucuuu cuucuuu                                        87
```

<210> SEQ ID NO 36
<211> LENGTH: 96
<212> TYPE: RNA
<213> ORGANISM: Artificial Sequence
<220> FEATURE:
<223> OTHER INFORMATION: Synthetic RNA

<400> SEQUENCE: 36

```
agccauuucc uguuuuuuuu uuuuuuuuuu uuuuuuuuuu cuuuuuuuuu uucuuuccuu    60
uccuucuuuu uuuccuuucu uuuucccuuc uuuaau                              96
```

<210> SEQ ID NO 37
<211> LENGTH: 101
<212> TYPE: RNA
<213> ORGANISM: Artificial Sequence
<220> FEATURE:
<223> OTHER INFORMATION: Synthetic RNA

<400> SEQUENCE: 37

```
ggccauuucc uguuuuuuuu uuuuuuggu uuuuuuuuuu uuuuuuuuuu uuuuuuuuuu     60
uuuuuuuucc uuuccuucuu uuuuuuuuuu ucccucuuua u                       101
```

<210> SEQ ID NO 38
<211> LENGTH: 87
<212> TYPE: RNA
<213> ORGANISM: Artificial Sequence
<220> FEATURE:
<223> OTHER INFORMATION: Synthetic RNA

<400> SEQUENCE: 38

```
ggccauuucc uguuuuuuuu uuuuuuuuuu uuuuuuuuuu uuuuucuuu uccuucuuuu     60 ucccuuuuuc uuucuuccuu cuuuaau                                        87
```

<210> SEQ ID NO 39
<211> LENGTH: 100
<212> TYPE: RNA
<213> ORGANISM: Artificial Sequence
<220> FEATURE:
<223> OTHER INFORMATION: Synthetic RNA

<400> SEQUENCE: 39

```
ggccauccug uguuuuuuuu uuuuuuuuuu uuuuuuuuuu uuuuuuuuuu uuuuuuuuuu    60
uuuuuuuuuu uuuuuuuuuu uuuuuuuauu uccuuuucuu                         100
```

<210> SEQ ID NO 40
<211> LENGTH: 109
<212> TYPE: RNA
<213> ORGANISM: Artificial Sequence
<220> FEATURE:
<223> OTHER INFORMATION: Synthetic RNA

<400> SEQUENCE: 40

```
ggccaaccug uuuuuuuuu uuuuuuuuuu uuuuuuccuu uuuuuuuuuu uuuuuuuuuu        60
uuuuuuuuuu uuccuuuuuu ucuuuuuuuu uuuuuuuuuc cuuccuuuu                   109

<210> SEQ ID NO 41
<211> LENGTH: 34
<212> TYPE: RNA
<213> ORGANISM: Artificial Sequence
<220> FEATURE:
<223> OTHER INFORMATION: Synthetic RNA

<400> SEQUENCE: 41
ggccauccug uuuuuuuuuu uuuuuucuuu cuuu                                   34

<210> SEQ ID NO 42
<211> LENGTH: 74
<212> TYPE: RNA
<213> ORGANISM: Artificial Sequence
<220> FEATURE:
<223> OTHER INFORMATION: Synthetic RNA

<400> SEQUENCE: 42
ggccauuuuu ccuuuuuuuu uuuuuuuuuu uuuuucuuuu uuuuuccuu uuuuucuuuu        60 uuuuucuuuu cuuu                                                         74

<210> SEQ ID NO 43
<211> LENGTH: 81
<212> TYPE: RNA
<213> ORGANISM: Artificial Sequence
<220> FEATURE:
<223> OTHER INFORMATION: Synthetic RNA

<400> SEQUENCE: 43
ggccauucuu uuuuuuuuu uuuuuuuuuu uuuuuuuuuu uuucguuucu uuuucuucuu        60
uuuguuuucu cuucuccuuu u                                                 81

<210> SEQ ID NO 44
<211> LENGTH: 107
<212> TYPE: RNA
<213> ORGANISM: Artificial Sequence
<220> FEATURE:
<223> OTHER INFORMATION: Synthetic RNA

<400> SEQUENCE: 44
ggccauuccc cuuuuuuuuu uuuuuccgcu uuuuuuuuuu uuuuuuuuuu uuuuuuuuuu        60
uucuuuuuuu uuccuuuuuu uuuuuuuuuu uuuuuuuuuu ucuuuuu                     107

<210> SEQ ID NO 45
<211> LENGTH: 109
<212> TYPE: RNA
<213> ORGANISM: Artificial Sequence
<220> FEATURE:
<223> OTHER INFORMATION: Synthetic RNA

<400> SEQUENCE: 45
ggccaucccc cuuuuuuuuu uuuuccgcuu uuuuuuuuuu uuuuuuuuuc uuuuuuuuuu        60
ucuuuuuuuu uuccuuuuuu uuuuuuuuuu uuuuuuucu uuucuuuuu                    109

<210> SEQ ID NO 46
<211> LENGTH: 35
<212> TYPE: RNA
<213> ORGANISM: Artificial Sequence
<220> FEATURE:
```

<223> OTHER INFORMATION: Synthetic RNA

<400> SEQUENCE: 46
ggccauucuu uuuuuuuuu uuuucuuucu ucuuu                                35

<210> SEQ ID NO 47
<211> LENGTH: 48
<212> TYPE: RNA
<213> ORGANISM: Artificial Sequence
<220> FEATURE:
<223> OTHER INFORMATION: Synthetic RNA

<400> SEQUENCE: 47
ggccaucccc uucuuuuuuu uuuuuuuuuu uuuuuccuuu ucuucuuu                 48

<210> SEQ ID NO 48
<211> LENGTH: 100
<212> TYPE: RNA
<213> ORGANISM: Artificial Sequence
<220> FEATURE:
<223> OTHER INFORMATION: Synthetic RNA

<400> SEQUENCE: 48
ggccauccug uuuuuuuccc uuuuuuuuuu ucuuuuuuuu uuuuuuuuuu uuuuuuuuuu    60
ucuccuuuuu uuuuccucuu uuuuuccuuu ucuuccuuu                          100

<210> SEQ ID NO 49
<211> LENGTH: 112
<212> TYPE: RNA
<213> ORGANISM: Artificial Sequence
<220> FEATURE:
<223> OTHER INFORMATION: Synthetic RNA

<400> SEQUENCE: 49
ggccguccug uuuuuuuuuu uuuuuuuuuc uuuuuuuuuu uuuuuuuuuu uuuuuuuuuu    60
uuuuuuuuuu uuuuuuuuuu uuuuuuuuuu uuuuuuuucu ucuuucuuuc uu          112

<210> SEQ ID NO 50
<211> LENGTH: 145
<212> TYPE: RNA
<213> ORGANISM: Artificial Sequence
<220> FEATURE:
<223> OTHER INFORMATION: Synthetic RNA

<400> SEQUENCE: 50
ggccauuucc uguuuuuuuu uuuuuuuuuu uuuuuuuuuu uuuuuuuuuu uuuuuuuuuu    60
uuuuucuuuu uuuuuuuuuu uuuccuuuuu uuuuuuuuuu uuuuucuuuc cuucuuuuuu   120 ccuucuuuu ccuuccuucu uuaau                                         145

<210> SEQ ID NO 51
<211> LENGTH: 95
<212> TYPE: RNA
<213> ORGANISM: Artificial Sequence
<220> FEATURE:
<223> OTHER INFORMATION: Synthetic RNA

<400> SEQUENCE: 51
ggccauuccu guuuuuuuuu uuuuucuu uuguuuuuuu uguuuuuuuu uuuuuuuuc       60 cuuucuuuuu uuuuuuuuuu ccuucuucu uuaau                               95

<210> SEQ ID NO 52
<211> LENGTH: 72

<212> TYPE: RNA
<213> ORGANISM: Artificial Sequence
<220> FEATURE:
<223> OTHER INFORMATION: Synthetic RNA

<400> SEQUENCE: 52
ggccauuucc uguuuuuuuu uuuuuuuuuu uucuuccuu cuuuuuccu uucuuuuccu    60 uccuucuuua au                                                     72

<210> SEQ ID NO 53
<211> LENGTH: 87
<212> TYPE: RNA
<213> ORGANISM: Artificial Sequence
<220> FEATURE:
<223> OTHER INFORMATION: Synthetic RNA

<400> SEQUENCE: 53
ggccauuucc uguuuuuuuu uuuuuuuuuu uuuuuuuuuu uuuuucuuu uccuucuuuu   60 ucccuuuuuc uuucuuccuu cuuuaau                                     87

<210> SEQ ID NO 54
<211> LENGTH: 143
<212> TYPE: RNA
<213> ORGANISM: Artificial Sequence
<220> FEATURE:
<223> OTHER INFORMATION: Synthetic RNA

<400> SEQUENCE: 54
ggccauuucc uguuuuuuuu uuuuuuuuuu uuuuuuuuuu uuuuuuuuuu uuuuuuuuuu   60
uuucuuuuuu uuuuuuuuuu uccuuuuuuu uuuuuuuuuu uuucuuuccu ucuuuuuucc  120
uuucuuuucc uuccuucuuu aau                                         143

<210> SEQ ID NO 55
<211> LENGTH: 108
<212> TYPE: RNA
<213> ORGANISM: Artificial Sequence
<220> FEATURE:
<223> OTHER INFORMATION: Synthetic RNA

<400> SEQUENCE: 55
ggccauuucc uguuuuuuuu uuuuucccu uuuuuuuuuu uuuuuuuuuu uuuuuuuuuu    60 uuuuucuuu ccuucuuuuu uuuccuuucu uuuccuuccu ucuuuaau               108

<210> SEQ ID NO 56
<211> LENGTH: 82
<212> TYPE: RNA
<213> ORGANISM: Artificial Sequence
<220> FEATURE:
<223> OTHER INFORMATION: Synthetic RNA

<400> SEQUENCE: 56
ggcauccugu uuuuuuuuuu uuuuuuuuuu uuuuuuuuuu uuuuuuuuuu uuuuuuuuuu   60
uuuuuuuuuu uuucuuuucu uu                                          82

<210> SEQ ID NO 57
<211> LENGTH: 130
<212> TYPE: RNA
<213> ORGANISM: Artificial Sequence
<220> FEATURE:
<223> OTHER INFORMATION: Synthetic RNA

<400> SEQUENCE: 57

```
acacuccauu ucuuuuuug uuuuuuuuuu uuuuuuuuuu uuuuuuuuuu uuuuuuuuuu    60
uuuuuuuuuu uuuuuuuuuu uuuuuucuu uucuuuccu ucuuuucug acuucuaauu    120 uuccuucuua                                                        130

<210> SEQ ID NO 58
<211> LENGTH: 129
<212> TYPE: RNA
<213> ORGANISM: Artificial Sequence
<220> FEATURE:
<223> OTHER INFORMATION: Synthetic RNA

<400> SEQUENCE: 58
guccuucugu uuuuuuuuu uuuuuuuuuu uuuuuuuuuu uuuuuuuuuu uuuuuuuuuu    60
uuuuuuuuuu uuuuuuuuuu uuuuuuuccu uacccuuucc ucuuuucuu ccuuuuuuu    120 ccuuacuuu                                                         129

<210> SEQ ID NO 59
<211> LENGTH: 57
<212> TYPE: RNA
<213> ORGANISM: Artificial Sequence
<220> FEATURE:
<223> OTHER INFORMATION: Synthetic RNA

<400> SEQUENCE: 59
ggguccccuu guuuuuuuu uucuuuccu ucuuuccuuu ccuaaucuuu cuuucuu       57

<210> SEQ ID NO 60
<211> LENGTH: 96
<212> TYPE: RNA
<213> ORGANISM: Artificial Sequence
<220> FEATURE:
<223> OTHER INFORMATION: Synthetic RNA

<400> SEQUENCE: 60
agccauuucc uguuuuuuuu uuuuuuuuuu uuuuuuuuuu cuuuuuuuuu uucuuuccuu   60
uccuucuuuu uuuccuuucu uuuucccuuc uuuaau                            96

<210> SEQ ID NO 61
<211> LENGTH: 115
<212> TYPE: RNA
<213> ORGANISM: Artificial Sequence
<220> FEATURE:
<223> OTHER INFORMATION: Synthetic RNA

<400> SEQUENCE: 61
ggccauuucc uguuuuuuuu uuuuuuguu uuuuuuuuuu uuuuuuuuuu uuuuuuuuuu    60
uuuuuuuuuu uuuuuuuuuu uuuccuuucc uuuuuuuuuu uuuuucccuu uuuau        115

<210> SEQ ID NO 62
<211> LENGTH: 107
<212> TYPE: RNA
<213> ORGANISM: Artificial Sequence
<220> FEATURE:
<223> OTHER INFORMATION: Synthetic RNA

<400> SEQUENCE: 62
ggccauccug uuuuuuuuu uuuuuuuuuu uucuuuuuuu uuuuuuuuuu cuuuuuuuuu    60
cuucuuuuuc uuuccuuuuu uuuuuuuuuu uuuuuuuuc uucuuuc                 107

<210> SEQ ID NO 63
<211> LENGTH: 96
```

```
<212> TYPE: RNA
<213> ORGANISM: Artificial Sequence
<220> FEATURE:
<223> OTHER INFORMATION: Synthetic RNA

<400> SEQUENCE: 63
ggccauuucc uguuuuuuuu uuuuuuuuuu uuuuuuuuuu uuuuuuuuuu uuuuuuuucu    60
uuuucccucu uuucuucuc uuuuccuuc uuuaau                                96

<210> SEQ ID NO 64
<211> LENGTH: 111
<212> TYPE: RNA
<213> ORGANISM: Artificial Sequence
<220> FEATURE:
<223> OTHER INFORMATION: Synthetic RNA

<400> SEQUENCE: 64
gcuaacuguu ccuuuuuuuu uuuuuuuuuu uuuuuuuuuu uuuuuuuuuu uuuuucuuuu    60
uuuuuuuuuu cccucuuucu ucccuucuca ucuuauucua cuucuuucu u              111

<210> SEQ ID NO 65
<211> LENGTH: 107
<212> TYPE: RNA
<213> ORGANISM: Artificial Sequence
<220> FEATURE:
<223> OTHER INFORMATION: Synthetic RNA

<400> SEQUENCE: 65
gcuaacuguu ccuuuuuuuu uuuuuuuuuu uuuuuuuuuu uuuuuuuuuu cuuuuuuuu     60 uuuuuucccu cuuucuuccc uucucaucuu auucuacuuu cuuucuu                  107

<210> SEQ ID NO 66
<211> LENGTH: 92
<212> TYPE: RNA
<213> ORGANISM: Artificial Sequence
<220> FEATURE:
<223> OTHER INFORMATION: Synthetic RNA

<400> SEQUENCE: 66
gcuaacuguu ccuuuuuuuu uuucuuuuuu uuuuuuuuuu uuuuuuuuuu uccuucuuc     60 uuucuuucuu accuuacuuu acuuucuuuu cu                                  92

<210> SEQ ID NO 67
<211> LENGTH: 111
<212> TYPE: RNA
<213> ORGANISM: Artificial Sequence
<220> FEATURE:
<223> OTHER INFORMATION: Synthetic RNA

<400> SEQUENCE: 67
gcuaacaguu ucucuuuuuu uuuuuuuccu uuuuuauuuu uauuuuuuuu uuuuuuuuu     60 uuuuuuuauu uucuuuuccu uucuuucuca ccuuacauua cuucuuucu u              111

<210> SEQ ID NO 68
<211> LENGTH: 77
<212> TYPE: RNA
<213> ORGANISM: Artificial Sequence
<220> FEATURE:
<223> OTHER INFORMATION: Synthetic RNA

<400> SEQUENCE: 68
gcuaauuucc uuauguuuuu uuuuuuuuuu uuuucuuuc cauuccuuc cuucuuacuu      60
```

-continued cacuuuaccu ucuuucu    77

<210> SEQ ID NO 69
<211> LENGTH: 124
<212> TYPE: RNA
<213> ORGANISM: Artificial Sequence
<220> FEATURE:
<223> OTHER INFORMATION: Synthetic RNA

<400> SEQUENCE: 69
gcuaacuguu uuuuuuuuu uuuuuuuuuu uuuuuuuuuu uuuuuuuuuu uuuuuuuuuu    60
uuuuuuuuuu uuuuuuuuuu uuuuccuuu ccuucuuuc uuaccuuacu uuacauucuu    120
uucu    124

<210> SEQ ID NO 70
<211> LENGTH: 119
<212> TYPE: RNA
<213> ORGANISM: Artificial Sequence
<220> FEATURE:
<223> OTHER INFORMATION: Synthetic RNA

<400> SEQUENCE: 70
gcuaacuguu ccuuuuuuuu uuuuuuuuuu uuuuuuuuuu uuuuuuuuuu uuuuuuuuuu    60
uuuuuuuuuu uuuuuuuuuu uucuuuccuu ccuuucucac cuucuuuuac uucuuuccu    119

<210> SEQ ID NO 71
<211> LENGTH: 93
<212> TYPE: RNA
<213> ORGANISM: Artificial Sequence
<220> FEATURE:
<223> OTHER INFORMATION: Synthetic RNA

<400> SEQUENCE: 71
gcuaacuguu uuuuuuuuu uuuuuuuuuu uuuuuuuuuu uuuuuuuuuu uucuuuucu    60 uuccuuuccu ucuuacucua cuuuacuuuu ucu    93

<210> SEQ ID NO 72
<211> LENGTH: 129
<212> TYPE: RNA
<213> ORGANISM: Artificial Sequence
<220> FEATURE:
<223> OTHER INFORMATION: Synthetic RNA

<400> SEQUENCE: 72
gcuaacuguu cuuuuuuuu uuuuuuuuuu uuuuuuuuuu uuuuuuuuuu uuuuuuuuuu    60
uuuuuuuuuu uuuuuuuuuu uuuuuuuuuc uuuuccuucu cuuucuuac cuuauuuucc    120 uucuuucuu    129

<210> SEQ ID NO 73
<211> LENGTH: 86
<212> TYPE: RNA
<213> ORGANISM: Artificial Sequence
<220> FEATURE:
<223> OTHER INFORMATION: Synthetic RNA

<400> SEQUENCE: 73
gcuaacuguu uuuuuuuuu uuuuuuuuuu uuuuuuuucu uuuuuuuucu uucuuuccu    60 ucuuaccuua cuuuacuuuc uuuucu    86

<210> SEQ ID NO 74
<211> LENGTH: 133

<212> TYPE: RNA
<213> ORGANISM: Artificial Sequence
<220> FEATURE:
<223> OTHER INFORMATION: Synthetic RNA

<400> SEQUENCE: 74
gcuaacuguu uuuuuuuuu uuuuuuuuu uuuuuuuuu uuuuuuuuu uuuuuuuuu    60
uuuuuuuuu uuuuuuuuu uuuuuuuuc cuuuuccuu uuccuucucu uuuuaccuua  120
cuuuacuuuu cuu                                                  133

<210> SEQ ID NO 75
<211> LENGTH: 144
<212> TYPE: RNA
<213> ORGANISM: Artificial Sequence
<220> FEATURE:
<223> OTHER INFORMATION: Synthetic RNA

<400> SEQUENCE: 75
gcuaacuguc ccuuuuuuuu uuuuuuuuu uuuuuuuuu uuuuuuuuu uuuuuuuuu    60
uuuuuuuuu uuuuuuuuu uuuuuuuuu uuuuucuuu uuuucucuuu uccuucuuuc  120
uuaccuuauu uuacuuucuu uccu                                      144

<210> SEQ ID NO 76
<211> LENGTH: 119
<212> TYPE: RNA
<213> ORGANISM: Artificial Sequence
<220> FEATURE:
<223> OTHER INFORMATION: Synthetic RNA

<400> SEQUENCE: 76
gcuaacuguc ccuuuuuuuu uguuuuuuuu uuuuuuuuu uuuuuuuuu uucuuuuuuu    60
uuuuuuuuu uguuucuuuu ccuucucauu uccuucuuau cuuaauuacu uccuuccu   119

<210> SEQ ID NO 77
<211> LENGTH: 88
<212> TYPE: RNA
<213> ORGANISM: Artificial Sequence
<220> FEATURE:
<223> OTHER INFORMATION: Synthetic RNA

<400> SEQUENCE: 77
gcuaacuguu uuuuuuuuu uuuuuuuuu uuuuuuuuu uuuuuuccu ucuuccuuuc    60
cuucuuaccu uacuuuauuu ucuuuccu                                   88

<210> SEQ ID NO 78
<211> LENGTH: 101
<212> TYPE: RNA
<213> ORGANISM: Artificial Sequence
<220> FEATURE:
<223> OTHER INFORMATION: Synthetic RNA

<400> SEQUENCE: 78
gcuaacuguu uuuuuuuuu uuuuuuuuu uuuuuuuuu uuuuuuuuu uuuuuuuuu    60
uucuuucuuu ucuuuucuca ccuuacuuua cuuccuuucu u                  101

<210> SEQ ID NO 79
<211> LENGTH: 86
<212> TYPE: RNA
<213> ORGANISM: Artificial Sequence
<220> FEATURE:
<223> OTHER INFORMATION: Synthetic RNA

<400> SEQUENCE: 79
gcuaguuuuc uuuuuuuuuu uuuuuuuuuu uuugguuuuu uuuuuuuuuc cucuuuuucc    60
guauuuuuuu uuuuuccucu uuucuu                                          86

<210> SEQ ID NO 80
<211> LENGTH: 38
<212> TYPE: DNA
<213> ORGANISM: Artificial Sequence
<220> FEATURE:
<223> OTHER INFORMATION: Synthetic DNA

<400> SEQUENCE: 80
taatacgact cactataggt ggctccatct tagcccta                              38

<210> SEQ ID NO 81
<211> LENGTH: 27
<212> TYPE: DNA
<213> ORGANISM: Artificial Sequence
<220> FEATURE:
<223> OTHER INFORMATION: Synthetic DNA

<400> SEQUENCE: 81
acttgatctg cagagaggcc agtatca                                         27

<210> SEQ ID NO 82
<211> LENGTH: 25
<212> TYPE: DNA
<213> ORGANISM: Artificial Sequence
<220> FEATURE:
<223> OTHER INFORMATION: Synthetic DNA

<400> SEQUENCE: 82
atgggatcgg ccattgaaca agatc                                           25

<210> SEQ ID NO 83
<211> LENGTH: 23
<212> TYPE: DNA
<213> ORGANISM: Artificial Sequence
<220> FEATURE:
<223> OTHER INFORMATION: Synthetic DNA

<400> SEQUENCE: 83
cacccagcca ccagagtccc cag                                             23

<210> SEQ ID NO 84
<211> LENGTH: 23
<212> TYPE: DNA
<213> ORGANISM: Artificial Sequence
<220> FEATURE:
<223> OTHER INFORMATION: Synthetic DNA

<400> SEQUENCE: 84
ccctgcctcc tgtctaagga agg                                             23

<210> SEQ ID NO 85
<211> LENGTH: 105
<212> TYPE: RNA
<213> ORGANISM: Artificial Sequence
<220> FEATURE:
<223> OTHER INFORMATION: Synthetic RNA

<400> SEQUENCE: 85
ggccauccug uuuuuuuccc uuuuuuuuuu ucuuuuuuuu uuuuuuuuuu uuuuuuuuuu    60
uuuuuucucc uuuuuuuuuc cucuuuuuuu ccuuuucuuu ccuuu                     105

<210> SEQ ID NO 86
<211> LENGTH: 79
<212> TYPE: RNA
<213> ORGANISM: Artificial Sequence
<220> FEATURE:
<223> OTHER INFORMATION: Synthetic RNA

<400> SEQUENCE: 86 ccauuuucu uuuuuuuuu uuguuuguuu uuuuuuuuuu uuucuuccu ucuuccuga    60 cuuuuaauuu uccuucuua                                            79

<210> SEQ ID NO 87
<211> LENGTH: 116
<212> TYPE: RNA
<213> ORGANISM: Artificial Sequence
<220> FEATURE:
<223> OTHER INFORMATION: Synthetic RNA

<400> SEQUENCE: 87 ccauuuucu uuuuuuuuu uuuuuuuuuu uuuuuuuuuu uuuuuuuuuu uuuuuuugu    60 uuguuuuuu uuuuuuuuuu cuuuccuucu uuccugacuu uuaauuuucc uucuua     116

<210> SEQ ID NO 88
<211> LENGTH: 84
<212> TYPE: RNA
<213> ORGANISM: Artificial Sequence
<220> FEATURE:
<223> OTHER INFORMATION: Synthetic RNA

<400> SEQUENCE: 88
ggccauuucc uguuuuuuu uuuuuuuuuu uuuuuuuuuu uuuuuacccu uuuuucucuu    60
uuuuuuuuuu ccuucuucuu uaau                                         84

<210> SEQ ID NO 89
<211> LENGTH: 74
<212> TYPE: RNA
<213> ORGANISM: Artificial Sequence
<220> FEATURE:
<223> OTHER INFORMATION: Synthetic RNA

<400> SEQUENCE: 89
ggccauuucc uguuuuuuuu uuuuuuuuuu acccuuuuuu cucuuuuuuu uuuuuuuuuu    60
ccuucuucuu uaau                                                     74

<210> SEQ ID NO 90
<211> LENGTH: 38
<212> TYPE: RNA
<213> ORGANISM: Artificial Sequence
<220> FEATURE:
<223> OTHER INFORMATION: Synthetic RNA

<400> SEQUENCE: 90 ggccauuuc uguuuuuuuu uuuuuauuu ucuuuaau                            38

<210> SEQ ID NO 91
<211> LENGTH: 53
<212> TYPE: RNA
<213> ORGANISM: Artificial Sequence
<220> FEATURE:
<223> OTHER INFORMATION: Synthetic RNA

<400> SEQUENCE: 91

```
ggccauuuuc uuuuuuuuuu cucuuuuuuu uuuuuuuuuu uauuucuuu aau        53
```

<210> SEQ ID NO 92
<211> LENGTH: 82
<212> TYPE: RNA
<213> ORGANISM: Artificial Sequence
<220> FEATURE:
<223> OTHER INFORMATION: Synthetic RNA

<400> SEQUENCE: 92

```
ggccauuuuc uguuuuuuuu uuuuuuuuuu uuccuuuuuu uuuuuccuc uuuuuuuuuu    60 uuuuuuuuuu auuuucuuua au                                            82
```

<210> SEQ ID NO 93
<211> LENGTH: 82
<212> TYPE: RNA
<213> ORGANISM: Artificial Sequence
<220> FEATURE:
<223> OTHER INFORMATION: Synthetic RNA

<400> SEQUENCE: 93

```
ggccauuuuc uguuuuuuuu uuucuuuuuu uuuuuuuuuu uuccuuuuuu uuucucuuuu    60
uuuuuuuuuu auuuucuuua au                                            82
```

<210> SEQ ID NO 94
<211> LENGTH: 85
<212> TYPE: RNA
<213> ORGANISM: Artificial Sequence
<220> FEATURE:
<223> OTHER INFORMATION: Synthetic RNA

<400> SEQUENCE: 94

```
ggccauccug uuuuuuuuuu uuuuuuuuuu uuuuguuuu uuuuuuuuuu uucuuuuucc    60
uuuuuuuuuu uuuauuuucu ucuuu                                         85
```

<210> SEQ ID NO 95
<211> LENGTH: 59
<212> TYPE: RNA
<213> ORGANISM: Artificial Sequence
<220> FEATURE:
<223> OTHER INFORMATION: Synthetic RNA

<400> SEQUENCE: 95

```
gguccuaagu uuuuuuuuuu uucuuccuuc cuucuuuccu uuucuaauuu uccuucuuu    59
```

<210> SEQ ID NO 96
<211> LENGTH: 62
<212> TYPE: RNA
<213> ORGANISM: Artificial Sequence
<220> FEATURE:
<223> OTHER INFORMATION: Synthetic RNA

<400> SEQUENCE: 96

```
gguccuaagu uguuuuuuuu uuuuuuuccu uccuucuuuc ccuuuucuaa uuuuccuucu    60
uu                                                                  62
```

<210> SEQ ID NO 97
<211> LENGTH: 74
<212> TYPE: RNA
<213> ORGANISM: Artificial Sequence
<220> FEATURE:
<223> OTHER INFORMATION: Synthetic RNA

<400> SEQUENCE: 97

```
gguccuaagu uguuuuuuu uuuuuuuuu uuuuccuuu ccuuccuucu uuccuuuucu      60 aauuuccuu cuuu                                                      74

<210> SEQ ID NO 98
<211> LENGTH: 95
<212> TYPE: RNA
<213> ORGANISM: Artificial Sequence
<220> FEATURE:
<223> OTHER INFORMATION: Synthetic RNA

<400> SEQUENCE: 98
ggccauuucu guuuuuuuu uuuuuuuuu uuuuuuuuu uuuuuuuuu uuguuccuu        60 cuuuuccuu uucuuuuuu uuucucccu uuaau                                 95

<210> SEQ ID NO 99
<211> LENGTH: 70
<212> TYPE: RNA
<213> ORGANISM: Artificial Sequence
<220> FEATURE:
<223> OTHER INFORMATION: Synthetic RNA

<400> SEQUENCE: 99
ggccauuucu guuuuuuuu uuuuuguuuc cuucuuuuuc cuuucuuuu uuuuuuuuc      60 ucccuuuaau                                                          70
```